(12) United States Patent
Marczyk et al.

(10) Patent No.: US 8,475,453 B2
(45) Date of Patent: Jul. 2, 2013

(54) ENDOSCOPIC VESSEL SEALER AND DIVIDER HAVING A FLEXIBLE ARTICULATING SHAFT

(75) Inventors: Stanislaw Marczyk, Stratford, CT (US); Russell Pribanic, New Milford, CT (US); David Farascioni, Bethel, CT (US); Eric J. Taylor, East Hampton, CT (US); Peter Hathaway, Lebanon, CT (US)

(73) Assignee: Covidien LP, Mansfield, MA (US)

( * ) Notice: Subject to any disclaimer, the term of this patent is extended or adjusted under 35 U.S.C. 154(b) by 516 days.

(21) Appl. No.: 12/718,143

(22) Filed: Mar. 5, 2010

(65) Prior Publication Data

US 2010/0179540 A1 Jul. 15, 2010

Related U.S. Application Data

(63) Continuation-in-part of application No. 12/443,087, filed as application No. PCT/US2007/021440 on Oct. 5, 2007.

(60) Provisional application No. 60/850,214, filed on Oct. 6, 2006, provisional application No. 61/157,722, filed on Mar. 5, 2009, provisional application No. 61/249,054, filed on Oct. 6, 2009.

(51) Int. Cl.
*A61B 18/04* (2006.01)

(52) U.S. Cl.
USPC .................................................. 606/51

(58) Field of Classification Search
USPC ............................ 606/27, 34, 41, 51, 52
See application file for complete search history.

(56) References Cited

U.S. PATENT DOCUMENTS

| 1,822,330 | A | 9/1931 | Ainslie |
| 2,327,353 | A | 8/1943 | Karle |
| 3,073,311 | A | 1/1963 | Tibbs et al. |
| 4,236,470 | A | 12/1980 | Stenson |
| D263,020 | S | 2/1982 | Rau, III |
| D295,893 | S | 5/1988 | Sharkany et al. |

(Continued)

FOREIGN PATENT DOCUMENTS

| DE | 2415263 | 10/1975 |
| DE | 2514501 | 10/1976 |

(Continued)

OTHER PUBLICATIONS

U.S. Appl. No. 09/387,883, filed Sep. 1, 1999.

(Continued)

*Primary Examiner* — Michael Peffley
*Assistant Examiner* — Daniel Fowler

(57) ABSTRACT

An electrosurgical instrument for treating tissue includes a housing having a shaft extending therefrom having an axis A-A defined therethrough. The shaft is at least partially flexible and includes first and second jaw members attached at a distal end thereof. Each jaw member includes an electrically conductive tissue contacting surface adapted to connect to a source of electrosurgical energy such that the electrically conductive tissue contacting surfaces are capable of conducting electrosurgical energy through tissue held therebetween. A drive assembly is disposed in the housing and has a first actuator operably coupled to a drive rod for reciprocation thereof to move the jaw members from a first position in spaced relation to one another to a second position closer to one another for engaging tissue. A second actuator is disposed on the housing and is actuatable to articulate the shaft.

24 Claims, 67 Drawing Sheets

U.S. PATENT DOCUMENTS

| | | | |
|---|---|---|---|
| D295,894 S | 5/1988 | Sharkany et al. |
| 4,829,313 A | 5/1989 | Taggart |
| 5,037,433 A | 8/1991 | Wilk et al. |
| 5,042,707 A | 8/1991 | Taheri |
| 5,100,430 A | 3/1992 | Avellanet et al. |
| 5,209,747 A | 5/1993 | Knoepfler |
| 5,300,082 A | 4/1994 | Sharpe et al. |
| 5,308,353 A | 5/1994 | Beurrier |
| 5,314,445 A | 5/1994 | Heidmueller née Degwitz et al. |
| D348,930 S | 7/1994 | Olson |
| 5,330,502 A | 7/1994 | Hassler et al. |
| 5,350,391 A | 9/1994 | Iacovelli |
| 5,374,277 A | 12/1994 | Hassler |
| 5,389,103 A | 2/1995 | Melzer et al. |
| 5,403,342 A | 4/1995 | Tovey et al. |
| 5,439,478 A | 8/1995 | Palmer |
| 5,454,823 A | 10/1995 | Richardson et al. |
| 5,454,827 A | 10/1995 | Aust et al. |
| 5,456,401 A | 10/1995 | Green et al. |
| 5,480,406 A | 1/1996 | Nolan et al. |
| 5,540,706 A | 7/1996 | Aust et al. |
| 5,549,637 A | 8/1996 | Crainich |
| 5,564,615 A | 10/1996 | Bishop et al. |
| 5,575,799 A | 11/1996 | Bolanos et al. |
| 5,582,617 A | 12/1996 | Klieman et al. |
| 5,591,181 A | 1/1997 | Stone et al. |
| 5,601,224 A | 2/1997 | Bishop et al. |
| 5,620,415 A | 4/1997 | Lucey et al. |
| 5,643,294 A | 7/1997 | Tovey et al. |
| D384,413 S | 9/1997 | Zlock et al. |
| 5,662,662 A | 9/1997 | Bishop et al. |
| 5,674,229 A | 10/1997 | Tovey et al. |
| 5,690,652 A | 11/1997 | Wurster et al. |
| 5,690,653 A | 11/1997 | Richardson et al. |
| 5,752,973 A | 5/1998 | Kieturakis |
| 5,759,188 A | 6/1998 | Yoon |
| 5,766,196 A | 6/1998 | Griffiths |
| 5,779,646 A | 7/1998 | Koblish et al. |
| 5,792,165 A | 8/1998 | Klieman et al. |
| 5,797,537 A | 8/1998 | Oberlin et al. |
| 5,797,927 A | 8/1998 | Yoon |
| 5,814,054 A | 9/1998 | Kortenbach et al. |
| 5,817,119 A | 10/1998 | Klieman et al. |
| 5,827,323 A | 10/1998 | Klieman et al. |
| 5,876,412 A | 3/1999 | Piraka |
| 5,897,563 A | 4/1999 | Yoon et al. |
| 5,906,630 A | 5/1999 | Anderhub et al. |
| 5,928,136 A | 7/1999 | Barry |
| 5,954,731 A | 9/1999 | Yoon |
| 5,954,733 A | 9/1999 | Yoon |
| 5,957,937 A | 9/1999 | Yoon |
| 5,984,932 A | 11/1999 | Yoon |
| 5,984,939 A | 11/1999 | Yoon |
| 5,993,466 A | 11/1999 | Yoon |
| 5,993,467 A | 11/1999 | Yoon |
| 5,997,565 A | 12/1999 | Inoue |
| 6,004,332 A | 12/1999 | Yoon et al. |
| 6,017,358 A | 1/2000 | Yoon et al. |
| 6,027,522 A | 2/2000 | Palmer |
| D424,694 S | 5/2000 | Tetzlaff et al. |
| D425,201 S | 5/2000 | Tetzlaff et al. |
| 6,077,287 A | 6/2000 | Taylor et al. |
| 6,080,180 A | 6/2000 | Yoon |
| 6,086,601 A | 7/2000 | Yoon |
| 6,126,665 A | 10/2000 | Yoon |
| 6,139,563 A | 10/2000 | Cosgrove, III et al. |
| 6,143,005 A | 11/2000 | Yoon et al. |
| 6,171,316 B1 | 1/2001 | Kovac et al. |
| 6,206,893 B1 | 3/2001 | Klein et al. |
| 6,214,028 B1 | 4/2001 | Yoon et al. |
| 6,223,100 B1 | 4/2001 | Green |
| 6,224,614 B1 | 5/2001 | Yoon |
| 6,261,307 B1 | 7/2001 | Yoon et al. |
| D449,886 S | 10/2001 | Tetzlaff et al. |
| 6,319,262 B1 | 11/2001 | Bates et al. |
| 6,358,259 B1 | 3/2002 | Swain et al. |
| D457,958 S | 5/2002 | Dycus et al. |
| D457,959 S | 5/2002 | Tetzlaff et al. |
| 6,494,888 B1 | 12/2002 | Laufer et al. |
| 6,506,196 B1 | 1/2003 | Laufer |
| 6,517,539 B1 | 2/2003 | Smith et al. |
| 6,569,105 B1 | 5/2003 | Kortenbach et al. |
| 6,582,450 B2 | 6/2003 | Ouchi |
| 6,638,287 B2 | 10/2003 | Danitz et al. |
| 6,663,639 B1 | 12/2003 | Laufer et al. |
| 6,663,641 B1 | 12/2003 | Kovac et al. |
| 6,666,854 B1 | 12/2003 | Lange |
| 6,676,676 B2 | 1/2004 | Danitz et al. |
| 6,743,239 B1 | 6/2004 | Kuehn et al. |
| 6,743,240 B2 | 6/2004 | Smith et al. |
| 6,755,843 B2 | 6/2004 | Chung et al. |
| D493,888 S | 8/2004 | Reschke |
| 6,773,441 B1 | 8/2004 | Laufer et al. |
| D496,997 S | 10/2004 | Dycus et al. |
| D499,181 S | 11/2004 | Dycus et al. |
| 6,821,285 B2 | 11/2004 | Laufer et al. |
| 6,835,200 B2 | 12/2004 | Laufer et al. |
| 6,889,116 B2 | 5/2005 | Jinno |
| 6,936,061 B2 | 8/2005 | Sasaki |
| D509,297 S | 9/2005 | Wells |
| 6,964,662 B2 | 11/2005 | Kidooka |
| 6,972,017 B2 | 12/2005 | Smith et al. |
| 6,981,628 B2 | 1/2006 | Wales |
| 6,997,931 B2 | 2/2006 | Sauer et al. |
| 7,048,684 B2 | 5/2006 | Parasher et al. |
| 7,052,489 B2 | 5/2006 | Griego et al. |
| 7,063,715 B2 | 6/2006 | Onuki et al. |
| D525,361 S | 7/2006 | Hushka |
| 7,090,683 B2 | 8/2006 | Brock et al. |
| 7,107,124 B2 | 9/2006 | Green |
| D531,311 S | 10/2006 | Guerra et al. |
| D533,942 S | 12/2006 | Kerr et al. |
| 7,153,314 B2 | 12/2006 | Laufer et al. |
| D535,027 S | 1/2007 | James et al. |
| D541,418 S | 4/2007 | Schechter et al. |
| D541,938 S | 5/2007 | Kerr et al |
| 7,248,944 B2 | 7/2007 | Green |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| 7,540,872 B2 | 6/2009 | Schechter et al. |
| 7,703,653 B2 | 4/2010 | Shah et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 2001/0018591 A1 | 8/2001 | Brock et al. |
| 2002/0188294 A1 | 12/2002 | Couture et al. |
| 2004/0116924 A1 | 6/2004 | Dycus et al. |
| 2006/0074407 A1 | 4/2006 | Padget et al. |
| 2006/0253126 A1 | 11/2006 | Bjerken et al. |
| 2006/0282093 A1 | 12/2006 | Shelton, IV et al. |
| 2008/0082100 A1 | 4/2008 | Orton et al. |
| 2008/0083809 A1 | 4/2008 | Scirica |
| 2009/0054734 A1 | 2/2009 | DeSantis et al. |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 19506363 | 8/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 10 2004 026 179 | 12/2005 |
| DE | 20 2007 009 317 | 10/2007 |
| DE | 19738457 | 1/2009 |
| EP | 1159926 | 12/2001 |
| JP | 61-501068 | 9/1984 |

| | | |
|---|---|---|
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 8 224241 A | 9/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 00/36986 | 6/2000 |
| WO | WO 01/54604 | 8/2001 |
| WO | WO 2005/110264 | 11/2005 |
| WO | WO 2008/045348 | 4/2008 |
| WO | WO2008/045348 A2 | 4/2008 |

OTHER PUBLICATIONS

U.S. Appl. No. 09/591,328, filed Jun. 9, 2000.
U.S. Appl. No. 10/246,087, filed Sep. 17, 2002.
U.S. Appl. No. 12/336,970, filed Dec. 17, 2008.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/437,254, filed May 7, 2009.
U.S. Appl. No. 12/503,256, filed Jul. 15, 2009.
U.S. Appl. No. 12/535,869, filed Aug. 5, 2009.
U.S. Appl. No. 12/543,831, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 9, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/568,838, filed Sep. 29, 2009.
U.S. Appl. No. 12/569,395, filed Sep. 29, 2009.
U.S. Appl. No. 12/569,710, filed Sep. 29, 2009.
U.S. Appl. No. 12/574,001, filed Oct. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
U.S. Appl. No. 12/619,100, filed Nov. 16, 2009.
U.S. Appl. No. 12/665,081, filed Dec. 17, 2009.
U.S. Appl. No. 12/692,414, filed Jan. 22, 2010.
U.S. Appl. No. 12/696,592, filed Jan. 29, 2010.
U.S. Appl. No. 12/696,857, filed Jan. 29, 2010.
U.S. Appl. No. 12/700,856, filed Feb. 5, 2010.
U.S. Appl. No. 12/719,407, filed Mar. 8, 2010.
U.S. Appl. No. 12/728,994, filed Mar. 22, 2010.
U.S. Appl. No. 12/748,028, filed Mar. 26, 2010.
U.S. Appl. No. 12/757,340, filed Apr. 9, 2010.
U.S. Appl. No. 12/758,524, filed Apr. 12, 2010.
U.S. Appl. No. 12/759,551, filed Apr. 13, 2010.
U.S. Appl. No. 12/762,482, filed Apr. 19, 2010.
U.S. Appl. No. 12/766,476, filed Apr. 23, 2010.
U.S. Appl. No. 12/769,444, filed Apr. 28, 2010.
U.S. Appl. No. 12/770,369, filed Apr. 29, 2010.
U.S. Appl. No. 12/770,380, filed Apr. 29, 2010.
U.S. Appl. No. 12/770,387, filed Apr. 29, 2010.
U.S. Appl. No. 12/773,526, filed May 4, 2010.
U.S. Appl. No. 12/773,644, filed May 4, 2010.
U.S. Appl. No. 12/775,553, filed May 7, 2010.
U.S. Appl. No. 12/786,589, filed May 25, 2010.
U.S. Appl. No. 12/791,112, filed Jun. 1, 2010.
U.S. Appl. No. 12/792,001, filed Jun. 2, 2010.
U.S. Appl. No. 12/792,008, filed Jun. 2, 2010.
U.S. Appl. No. 12/792,019, filed Jun. 2, 2010.
U.S. Appl. No. 12/792,038, filed Jun. 2, 2010.
U.S. Appl. No. 12/792,051, filed Jun. 2, 2010.
U.S. Appl. No. 12/792,068, filed Jun. 2, 2010.
U.S. Appl. No. 12/792,097, filed Jun. 2, 2010.
U.S. Appl. No. 12/792,262, filed Jun. 2, 2010.
U.S. Appl. No. 12/792,299, filed Jun. 2, 2010.
U.S. Appl. No. 12/792,330, filed Jun. 2, 2010.
U.S. Appl. No. 12/820,024, filed Jun. 23, 2010.
U.S. Appl. No. 12/821,253, filed Jun. 23, 2010.
U.S. Appl. No. 12/832,772, filed Jul. 8, 2010.
Michael Choti, "Abdominoperineal Resection with the LigaSure Vessel Sealing System and LigaSure Atlas 20 cm Open Instrument" ; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Tinkcler L.F., "Combined Diathermy and Suction Forceps" , Feb. 6, 1967 (Feb. 6, 1965), British Medical Journal Feb. 6, 1976, vol. 1, nr. 5431 p. 361, ISSN: 0007-1447.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98957773 dated Aug. 1, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013894 dated Feb. 3, 2006.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020532 dated Jan. 10, 2006.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 016911 dated May 28, 2010.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 08 020807.7 dated Apr. 24, 2009.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.

Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/08146 dated Aug. 8, 2003.
Int'l Search Report PCT/US03/18676 dated Sep. 19, 2003.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/52460 dated Apr. 24, 2008.
Int'l Search Report PCT/US08/61498 dated Sep. 22, 2008.
Int'l Search Report PCT/US09/032690 dated Jun. 16, 2009.
Int'l Search Report PCT/US2010/026314 dated May 19, 2010.
International Search Report for PCT/US07/021440 date of completion is Jan. 28, 2008 (2 pages).
International Search Report for PCT/US2010/026314 date of completion is Apr. 19, 2010 (2 pages).
European Search Report EP 07 83 9310 completed Dec. 11, 2012.

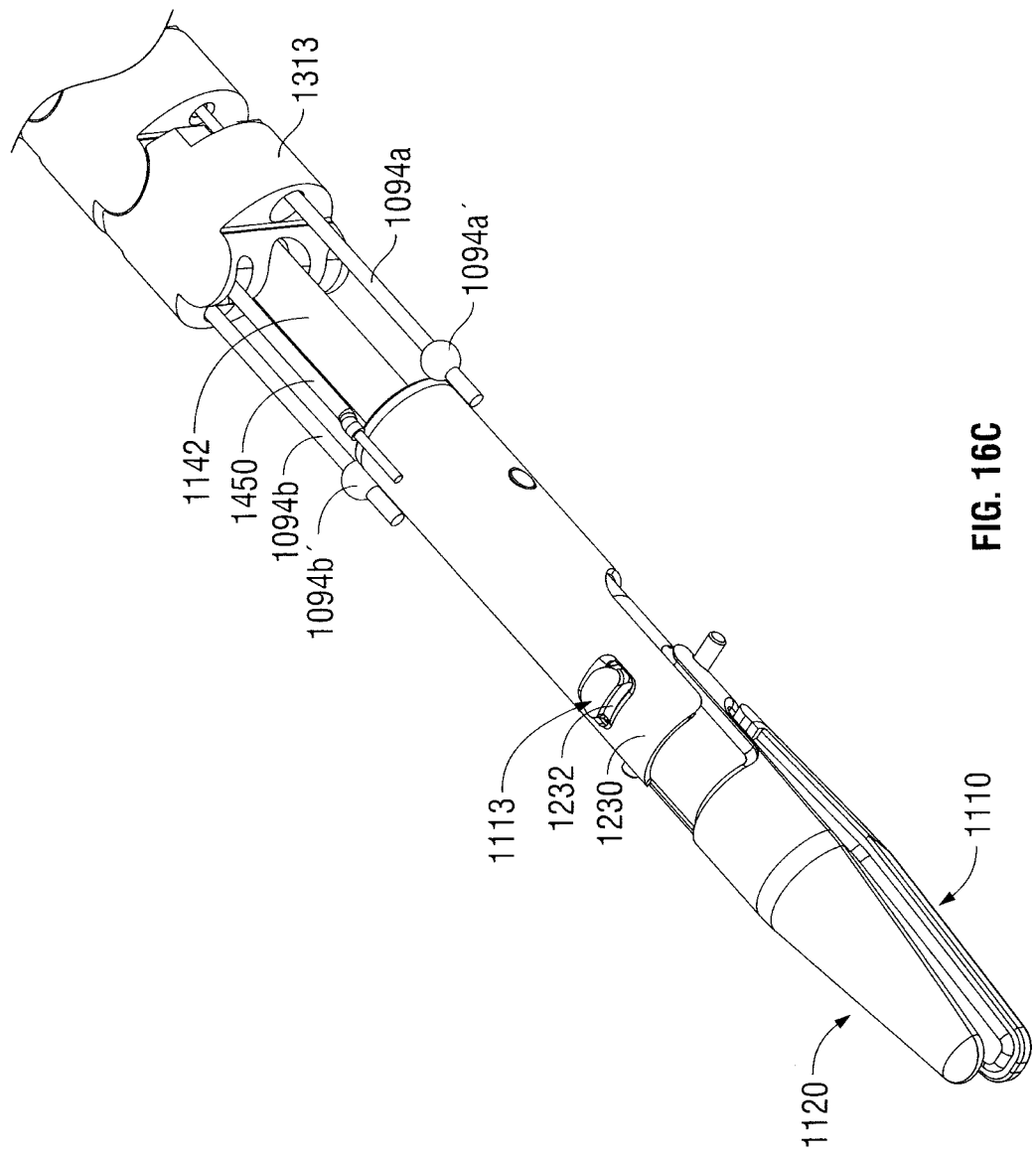

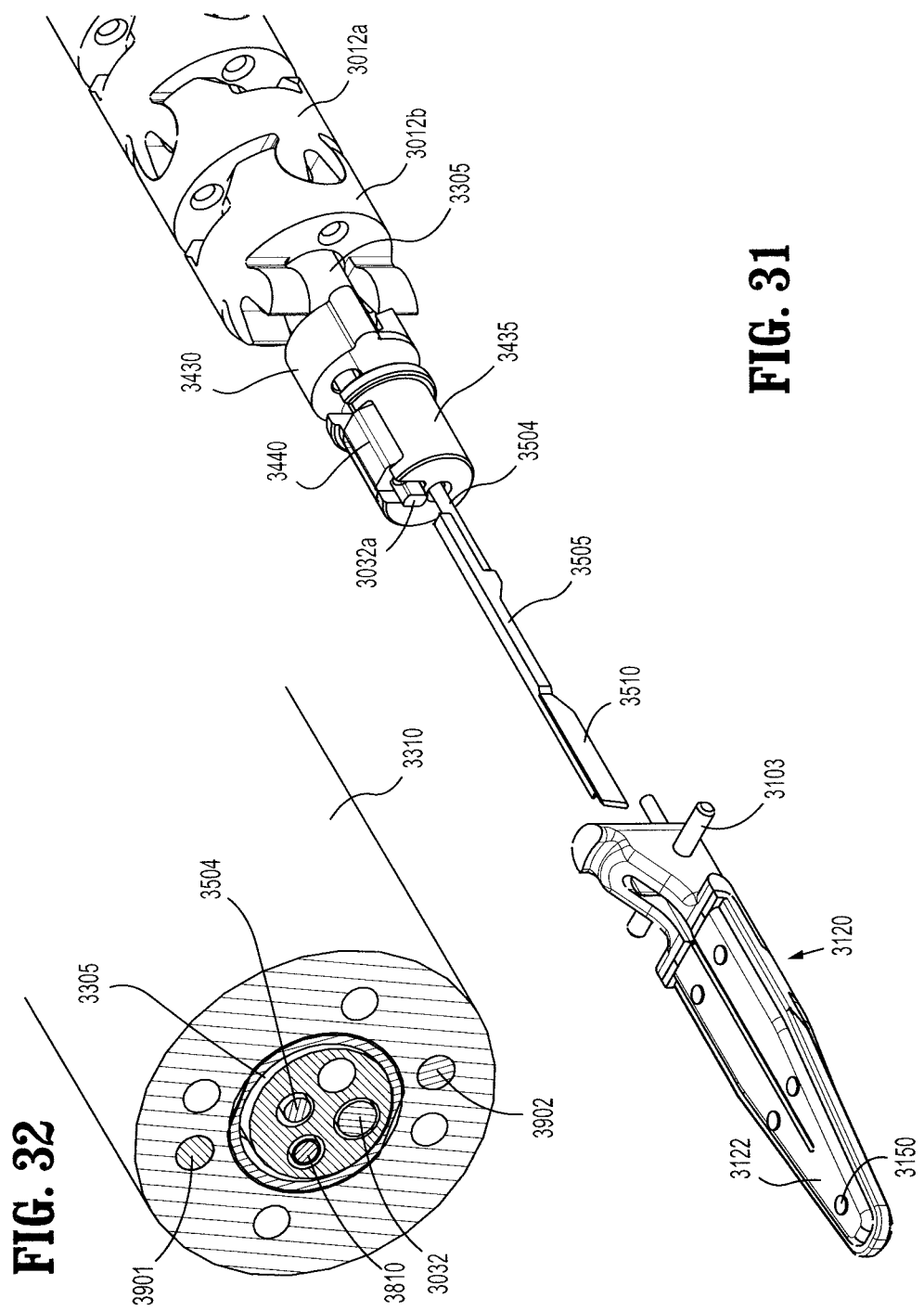

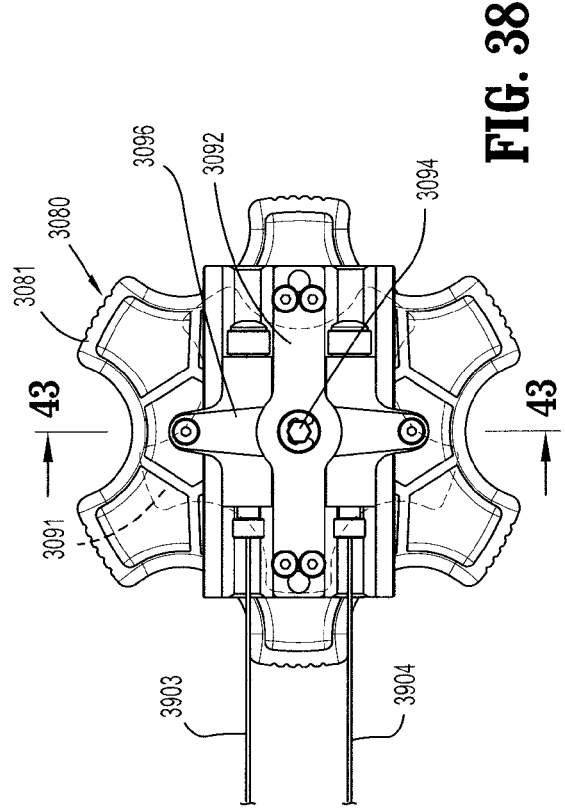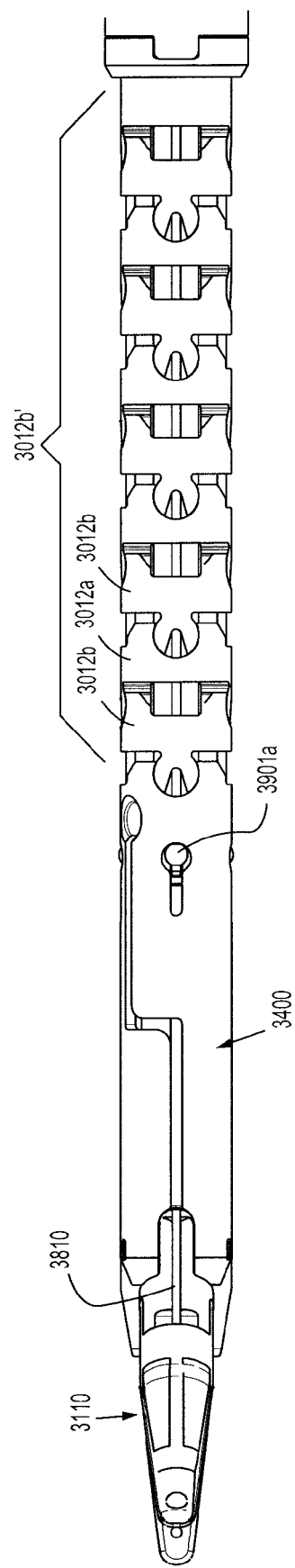

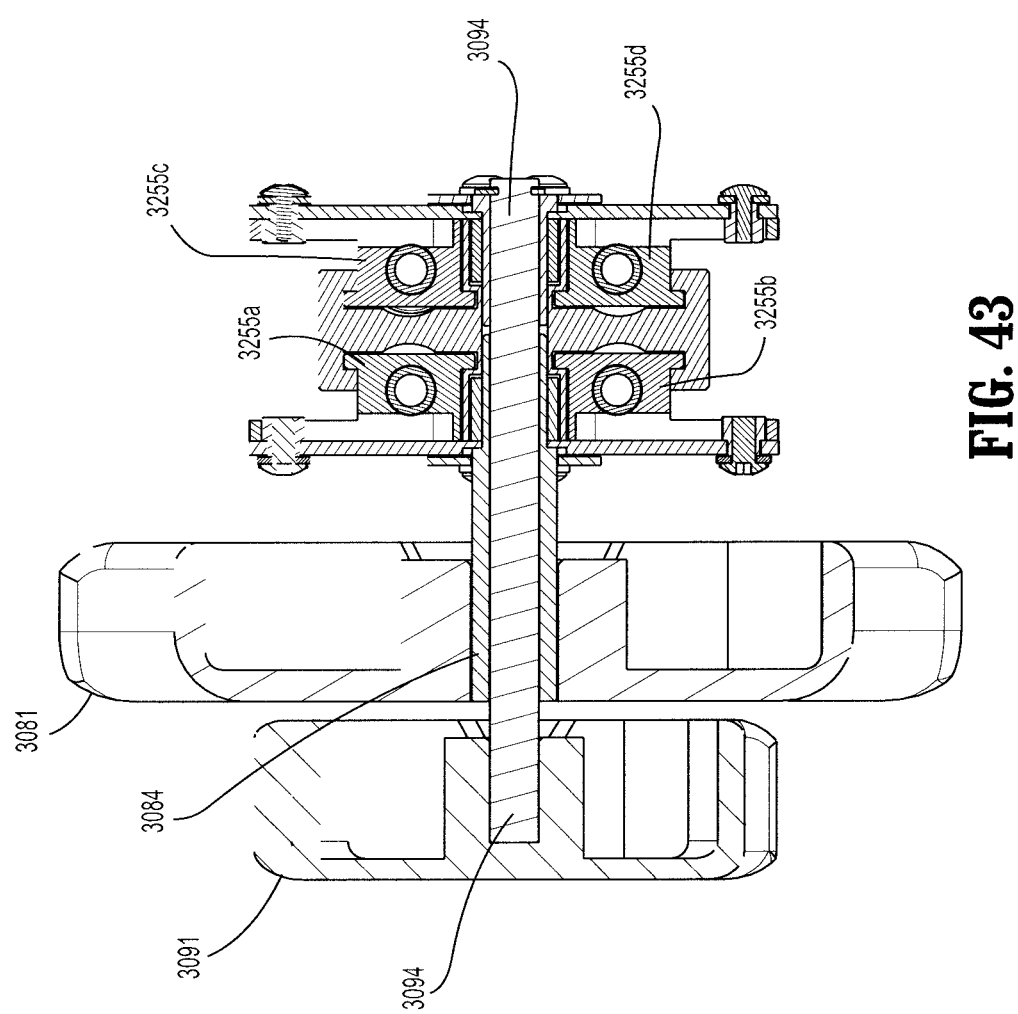

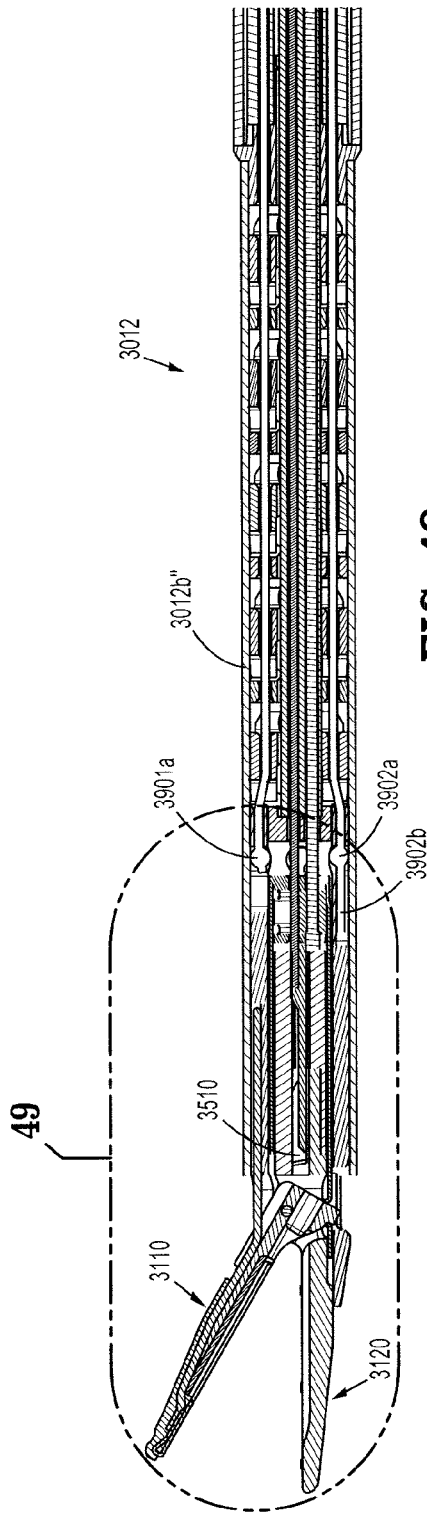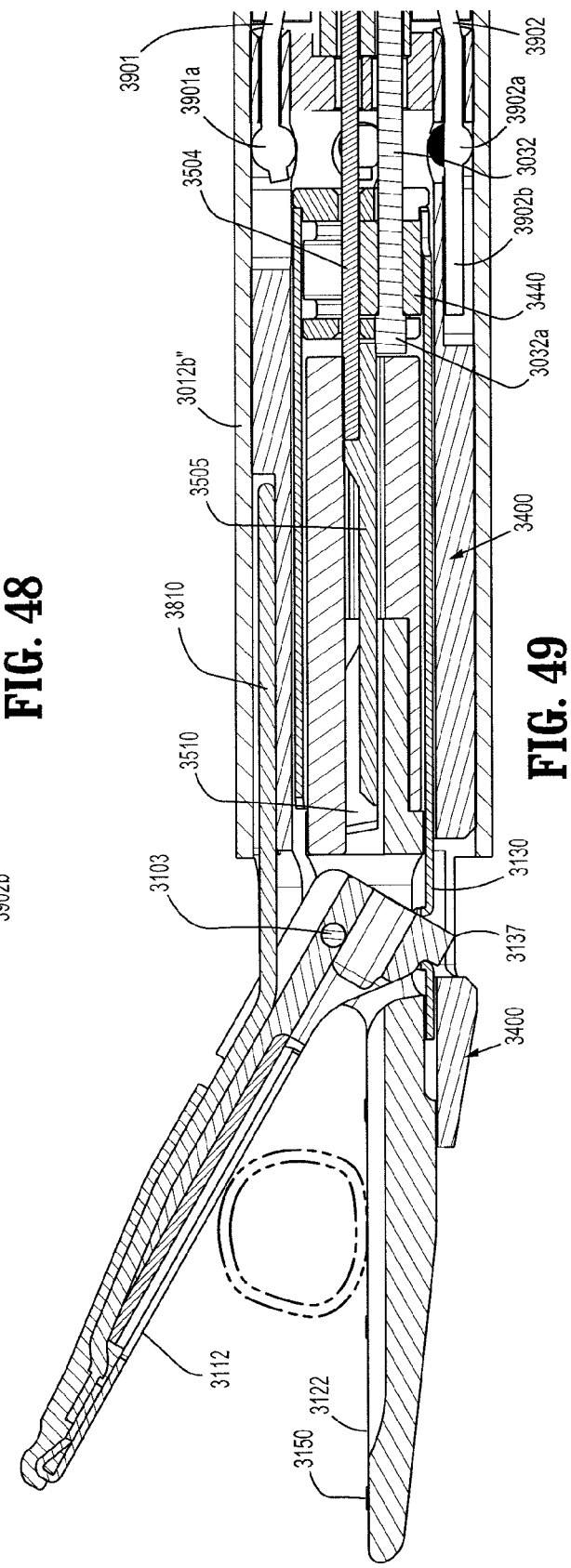
FIG. 48
FIG. 49

ENDOSCOPIC VESSEL SEALER AND DIVIDER HAVING A FLEXIBLE ARTICULATING SHAFT

CROSS REFERENCE TO RELATED APPLICATIONS

The present application is a Continuation-in-part Application claiming the benefit of and priority to U.S. application Ser. No. 12/443,087 filed on Mar. 26, 2009, which is a National Phase Application filed under 35 U.S.C. §371 of International Application Serial No. PCT/US2007/021440, filed Oct. 5, 2007, which claims the benefit of and priority to U.S. Provisional Application Ser. No. 60/850,214 filed on Oct. 6, 2006. The present Application also claims the benefit of and priority to U.S. Provisional Application Ser. No. 61/157,722 filed on Mar. 5, 2009. The present Application also claims the benefit of and priority to U.S. Provisional Application Ser. No. 61/249,054 filed on Oct. 6, 2009. The entire content of each of these Applications is incorporated herein by reference.

BACKGROUND

The present disclosure relates to an electrosurgical forceps and more particularly, the present disclosure relates to an endoscopic electrosurgical forceps for sealing and/or cutting tissue utilizing an elongated, generally flexible and articulating shaft.

TECHNICAL FIELD

Electrosurgical forceps utilize both mechanical clamping action and electrical energy to effect hemostasis by heating the tissue and blood vessels to coagulate, cauterize and/or seal tissue. As an alternative to open forceps for use with open surgical procedures, many modern surgeons use endoscopes and endoscopic instruments for remotely accessing organs through smaller, puncture-like incisions. As a direct result thereof, patients tend to benefit from less scarring and reduced healing time.

Generally, endoscopic surgery involves incising through body walls for example, viewing and/or operating on the ovaries, uterus, gall bladder, bowels, kidneys, appendix, etc. There are many common endoscopic surgical procedures, including arthroscopy, laparoscopy (pelviscopy), gastroentroscopy and laryngobronchoscopy, just to name a few. Typically, trocars are utilized for creating the incisions through which the endoscopic surgery is performed.

Trocar tubes or cannula devices are extended into and left in place in the abdominal wall to provide access for endoscopic surgical tools. A camera or endoscope is inserted through a relatively large diameter trocar tube which is generally located at the naval incision, and permits the visual inspection and magnification of the body cavity. The surgeon can then perform diagnostic and therapeutic procedures at the surgical site with the aid of specialized instrumentation, such as, forceps, cutters, applicators, and the like which are designed to fit through additional cannulas. Thus, instead of a large incision (typically 12 inches or larger) that cuts through major muscles, patients undergoing endoscopic surgery receive more cosmetically appealing incisions, between 5 and 10 millimeters in size. Recovery is, therefore, much quicker and patients require less anesthesia than traditional surgery. In addition, because the surgical field is greatly magnified, surgeons are better able to dissect blood vessels and control blood loss.

In continuing efforts to reduce the trauma of surgery, interest has recently developed in the possibilities of performing procedures to diagnose and surgically treat a medical condition without any incision in the abdominal wall by using a natural orifice (e.g., the mouth or anus) to access the target tissue. Such procedures are sometimes referred to as endoluminal procedures, transluminal procedures, or natural orifice transluminal endoscopic surgery ("NOTES"). Although many such endoluminal procedures are still being developed, they generally utilize a flexible endoscope instrument or flexible catheter to provide access to the tissue target tissue. Endoluminal procedures have been used to treat conditions within the lumen including for example, treatment of gastroesophageal reflux disease in the esophagus and removal of polyps from the colon. In some instances, physicians have gone beyond the luminal confines of the gastrointestinal tract to perform intra-abdominal procedures. For example, using flexible endoscopic instrumentation, the wall of the stomach can be punctured and an endoscope advanced into the peritoneal cavity to perform various procedures.

Using such endoluminal techniques, diagnostic exploration, liver biopsy, cholecystectomy, splenectomy, and tubal ligation have reportedly been performed in animal models. After the intra-abdominal intervention is completed, the endoscopic instrumentation is retracted into the stomach and the puncture closed. Other natural orifices, such as the anus or vagina, may also allow access to the peritoneal cavity.

As mentioned above, many endoscopic and endoluminal surgical procedures typically require cutting or ligating blood vessels or vascular tissue. However, this ultimately presents a design challenge to instrument manufacturers who must attempt to find ways to make endoscopic instruments that fit through the smaller cannulas. Due to the inherent spatial considerations of the surgical cavity, surgeons often have difficulty suturing vessels or performing other traditional methods of controlling bleeding, e.g., clamping and/or tying-off transected blood vessels. By utilizing an endoscopic electrosurgical forceps, a surgeon can either cauterize, coagulate/desiccate and/or simply reduce or slow bleeding simply by controlling the intensity, frequency and duration of the electrosurgical energy applied through the jaw members to the tissue. Most small blood vessels, i.e., in the range below two millimeters in diameter, can often be closed using standard electrosurgical instruments and techniques. However, if a larger vessel is ligated, it may be necessary for the surgeon to convert the endoscopic procedure into an open-surgical procedure and thereby abandon the benefits of endoscopic surgery. Alternatively, the surgeon can seal the larger vessel or tissue utilizing specialized vessel sealing instruments.

It is thought that the process of coagulating vessels is fundamentally different than electrosurgical vessel sealing. For the purposes herein, "coagulation" is defined as a process of desiccating tissue wherein the tissue cells are ruptured and dried. "Vessel sealing" or "tissue sealing" is defined as the process of liquefying the collagen in the tissue so that it reforms into a fused mass. Coagulation of small vessels is sufficient to permanently close them, while larger vessels need to be sealed to assure permanent closure. Moreover, coagulation of large tissue or vessels results in a notoriously weak proximal thrombus having a low burst strength whereas tissue seals have a relatively high burst strength and may be effectively severed along the tissue sealing plane.

More particularly, in order to effectively seal larger vessels (or tissue) two predominant mechanical parameters are accurately controlled—the pressure applied to the vessel (tissue) and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.006 inches. Below this range, the seal may shred or tear and above this range the lumens may not be properly or effectively sealed.

With respect to smaller vessels, the pressure applied to the tissue tends to become less relevant whereas the gap distance between the electrically conductive surfaces becomes more significant for effective sealing. In other words, the chances of the two electrically conductive surfaces touching during activation increases as vessels become smaller.

It has been found that the pressure range for assuring a consistent and effective seal is between about 3 kg/cm$^2$ to about 16 kg/cm$^2$ and, desirably, within a working range of 7 kg/cm$^2$ to 13 kg/cm$^2$. Manufacturing an instrument which is capable of providing a closure pressure within this working range has been shown to be effective for sealing arteries, tissues and other vascular bundles.

Various force-actuating assemblies have been developed in the past for providing the appropriate closure forces to effect vessel sealing. For example, commonly-owned U.S. patent application Ser. Nos. 10/460,926 and 11/513,979 disclose two different envisioned actuating assemblies developed by Covidien-Energy-based Devices of Boulder, Colo., for use with Covidien's vessel sealing and dividing instruments commonly sold under the trademark LIGASURE®. The contents of both of these applications are hereby incorporated by reference herein.

During use, one noted challenge for surgeons has been the inability to manipulate the end effector assembly of the vessel sealer to grasp tissue in multiple planes, i.e., off-axis, while generating the above-noted required forces to effect a reliable vessel seal. It would therefore be desirable to develop an endoscopic or endoluminal vessel sealing instrument which includes an end effector assembly capable of being manipulated along multiple axes to enable the surgeon to grasp and seal vessels lying along different planes within a surgical cavity.

Endoluminal procedures often require accessing tissue deep in tortuous anatomy of a natural lumen using a flexible catheter or endoscope. Conventional vessel sealing devices may not be appropriate for use in some endoluminal procedures because of a rigid shaft that can not easily negotiate the tortuous anatomy of a natural lumen It would therefore be desirable to develop an endoscopic or endoluminal vessel sealing instrument having a flexible shaft capable of insertion in a flexible endoscope or catheter.

SUMMARY

The present disclosure relates to an electrosurgical instrument for treating tissue which includes a housing having a flexible shaft extending therefrom with an axis A-A defined therethrough. The shaft includes first and second jaw members attached at a distal end thereof each including an electrically conductive tissue contacting surface adapted to connect to a source of electrosurgical energy. Upon electrical activation, the electrically conductive tissue contacting surfaces conduct electrosurgical energy through tissue held between the jaw members. A drive assembly is encased in the housing and includes a first actuator operably coupled to a drive rod for reciprocation thereof and a second actuator operably coupled to the drive rod for rotation thereof. A knife is included and operably coupled to a distal end of the drive rod. Actuation of the first actuator moves the jaw members from a first position in spaced relation to one another to a second position closer to one another for engaging tissue. Actuation of the second actuator rotates the drive rod about the axis A-A to translate the knife to cut tissue disposed between the jaw members.

According to another embodiment of the present disclosure, an endoscopic forceps includes a housing with a shaft affixed to a distal end thereof. The shaft includes a flexible portion having an end effector assembly at a distal end thereof that supports a pair of jaw members adapted to connect to a source of electrosurgical energy. One or both of the jaw members are moveable relative to the other from a first, spaced apart position to a second position wherein the jaw members are closer to one another for manipulating tissue. A drive assembly including an actuating handle is disposed within the housing and is configured to move the jaws for manipulating tissue.

An articulation assembly includes one or more steering cable operably coupled to the flexible portion of the shaft. The steering cables are configured to articulate the flexible portion of the shaft upon movement thereof. The articulation assembly includes one or more articulating wheels disposed atop the housing that operably couple to the one or more steering cables connected to the flexible portion of the shaft such that articulation of one or more of the articulation wheels moves the steering cable to articulate the flexible portion of the shaft relative the longitudinal axis.

In another embodiment, the articulation assembly includes a plurality of steering cables that are movable to articulate the flexible portion of the shaft in multiple planes relative to the longitudinal axis. In still another embodiment, the articulation assembly includes one or more sliders coupled to the steering cables. The sliders cooperate with the articulating wheels to move the steering cables longitudinally in response to rotational movement of the articulating wheels. A spindle may be included that operably connects to the slider(s) and to an indexing wheel that allows the articulating wheel to move in discreet increments thereby permitting discreet articulation of the flexible portion of the shaft.

In another embodiment, the spindle is operably coupled to a slider by a cam member configured to rotate along with the spindle. The cam member includes an eccentric arcuate surface thereon having a center dissimilar from a center of rotation of the cam member. The slider is operatively coupled to the eccentric arcuate surface such that rotation of the cam member induces longitudinal motion of the slider In one embodiment, the articulation assembly includes two articulating wheels that are configured to move the flexible portion of the shaft; a first articulating wheel configured to move the flexible portion of the shaft substantially along a first plane and a second articulating wheel configured to move the flexible portion of the shaft substantially along a second plane. Movement of the two articulating wheels sequentially or simultaneously induces a corresponding sequential or simultaneous motion of the flexible portion of the shaft in the first and second planes. The first articulation wheel is selectively movable independent of the second articulation wheel and vice versa.

In one embodiment, the flexible portion of the shaft includes a plurality of joints that are nestingly arranged to facilitate articulation of the flexible portion of the shaft relative to the longitudinal axis. Each joint of the plurality of joints may include one or a pair of distal knuckles and one or a pair of proximal clevises that nestingly engage one another to form the flexible portion of the shaft. Each pair of opposing distal knuckles and pair of opposing proximal clevises may be configured in an offset manner (offset ninety degrees (90°)) relative to one another. Each adjacent joint of the plurality of flexible joints may be offset ninety degrees (90°) relative to one another to facilitate movement of the joints. In yet another embodiment, one or more of the steering cables may be adapted to provide a return path to the electrosurgical energy source.

The drive assembly of the endoscopic forceps may include a drive rod extending at least partially through the flexible portion of the shaft. The drive rod may be operably coupled to the movable jaw member such that longitudinal reciprocation of the drive rod induces movement of the movable jaw member between the first and second positions. The drive assembly may also include a four bar mechanical linkage operably coupled to the drive rod to induce reciprocation of the drive rod. The four bar mechanical linkage may be operable from the housing. The drive rod may be substantially flexible.

According to another embodiment, an endoscopic surgical instrument for sealing tissue is provided. The instrument includes an end effector having a pair of jaw members adapted to connect to a source of electrosurgical energy. At least one of the jaw members is movable relative to the other to move the end effector between an open configuration wherein the jaw members are substantially spaced for receiving tissue and a closed configuration wherein the jaw members are closer together for contacting the tissue. A handle is manually movable to selectively induce motion in the end effector between the open configuration and the closed configuration. An elongated shaft defines a longitudinal axis and includes distal and proximal ends. The distal end is coupled to the end effector and the proximal end is coupled to the handle. The elongated shaft includes an articulating portion that is movable between an aligned configuration and an articulated configuration with respect to the longitudinal axis. An articulation assembly is operable to move the articulating portion of the elongated shaft between the aligned configuration and articulated configuration. The articulation assembly includes an actuator positioned on the instrument for manipulation by an operator during a surgical procedure. A cam member is coupled to the actuator such that the actuator is operable to rotate the cam member about a center of rotation. The cam member includes an eccentric arcuate surface that has a center dissimilar from the center of rotation of the cam member. A pair of cables is coupled to the arcuate surface such that rotation of the cam member induces differential longitudinal motion in the cables. The cables are coupled to the distal end of the elongated shaft such that the differential longitudinal motion in the pair of cables moves the articulating portion of the elongated shaft between the aligned configuration and the articulated configuration in a first plane of articulation.

The articulation assembly may include a second actuator positioned on the instrument for manipulation by an operator during a surgical procedure. The second actuator may be operable to induce motion of the articulating portion of the elongated shaft between aligned and articulated configurations in a second plane of articulation. The second actuator may be operable to rotate a second cam member about a center of rotation, and the second cam member may be coupled to a second pair of cables being coupled to the distal end of the elongated shaft.

The first actuator may include a rotatable wheel and the first cam member may include a cam wheel coupled to the rotatable wheel such that a given angular displacement of the rotatable wheel induces an equivalent angular displacement of the cam wheel. The arcuate surface may define a cam slot in the cam wheel extending between a radially inward and a radially outward positions on the cam wheel. The cam slot may be tapered such that angular displacement of the cam wheel induces greater differential longitudinal motion in the first pair of cables when the cam wheel is closer to a home position where the articulating portion is in the aligned configuration than when the cam wheel is further from the home position.

The instrument may also include an indexing mechanism for maintaining the articulation assembly in a plurality of relatively stable configurations to facilitate orienting the end effector in one of a plurality of discrete orientations. The indexing mechanism may include an indexing slide for engaging a plurality of teeth disposed on an outer circumferential surface of the first cam member.

The articulating portion may include a plurality of links arranged sequentially such that each of the links may pivot relative to a neighboring link to move the articulating portion between the aligned and articulated configurations. A first pivoting axis defined by one of the links may be radially offset from a second pivoting axis defined by another of the plurality of links by about 90° such that a second plane of articulation is substantially orthogonal to the first plane of articulation.

According to another aspect of the disclosure, an endoscopic surgical instrument for sealing tissue includes an end effector having a pair of jaw members adapted to connect to a source of electrosurgical energy. One or both jaw members is movable relative to the other to move the end effector between an open configuration wherein the jaw members are substantially spaced for receiving tissue and a closed configuration wherein the jaw members are closer together for contacting tissue. A handle is manually movable to selectively induce motion in the end effector between the open configuration and the closed configuration. An elongated shaft defines a longitudinal axis and includes distal and proximal ends. The distal end is coupled to the end effector and the proximal end is coupled to the handle. The elongated shaft includes an articulating portion to permit the end effector to articulate with respect to the longitudinal axis. A pair of steering cables extending between the distal and proximal ends of the elongated shaft is coupled to the distal end of the elongated shaft such that differential longitudinal motion in the steering cables induces articulation of the end effector. An actuator is coupled to the pair of steering cables by a cam member. The actuator is movable through a range of motion to impart rotational motion to the cam member. The cam member is configured to impart longitudinal motion to the steering cables as a function of a distance the actuator is moved through the range of motion.

BRIEF DESCRIPTION OF THE DRAWINGS

Various embodiments of the subject instrument are described herein with reference to the drawings wherein:

FIG. 16C is a bottom perspective of the partially flexible shaft of FIG. 13 with end effector assembly shown in partially open configuration;

FIG. 31 is an enlarged, front perspective view showing the various internal components of a knife assembly for cutting tissue disposed between the jaw members;

FIG. 32 is a greatly-enlarged, front perspective view of an outer tube configured to guide the steering cables therethrough and an internal tube or sleeve configured to guide the knife rod, drive rod and electrical lead therethrough;

FIG. 38 is an enlarged, bottom view of the articulating assembly showing the orientation of two steering cables of the plurality of steering cables in a "home" position;

FIG. 39 is an enlarged, top view of the flexible shaft in a non-articulated orientation;

FIG. 43 is an enlarged, cross sectional view of the articulation assembly;

FIG. 48 is an enlarged view of the area of detail of FIG. 27;

FIG. 49 is an enlarged view of the area of detail of FIG. 28;

DETAILED DESCRIPTION

The present disclosure relates to an electrosurgical forceps and more particularly, the present disclosure relates to an endoscopic electrosurgical forceps for sealing and/or cutting tissue utilizing an elongated, generally flexible and articulating shaft. In one embodiment, for example, such a device comprises a handle, handle assembly or other suitable actuating mechanism (e.g., robot, etc.) connected to a proximal end of a flexible, elongated body portion or shaft. A distal portion of the flexible shaft includes an articulating portion comprised of one or more joints to allow articulation of an end effector away from the longitudinal axis in response to actuation of articulation cables. An end effector is operatively supported on a distal end of the flexible shaft. The end effector includes a pair of jaws that can be actuated between a closed position and an open position. The jaws are adapted to supply electrical energy to tissue grasped between the jaws. The end effector also includes a knife assembly that can be actuated to cut tissue grasped within the jaws.

The functions of opening and closing the jaws; operating the knife assembly; and articulating the end effector can be performed remotely from the handle by actuation of various mechanisms in the handle. Mechanical motion may be transmitted from the handle through the flexible shaft to the end effector by flexible cables or rods within the flexible shaft. For example, in one embodiment two cables are used to provide articulation; one push-pull style cable opens and closes the jaws; and a second push-pull style cable actuates the knife assembly. The device is adapted to be placed in a lumen of a flexible endoscope and then inserted into a natural orifice of a patient and transited endoluminally through the anatomy of the natural lumen to a treatment site within or outside the natural lumen.

Figure 1:
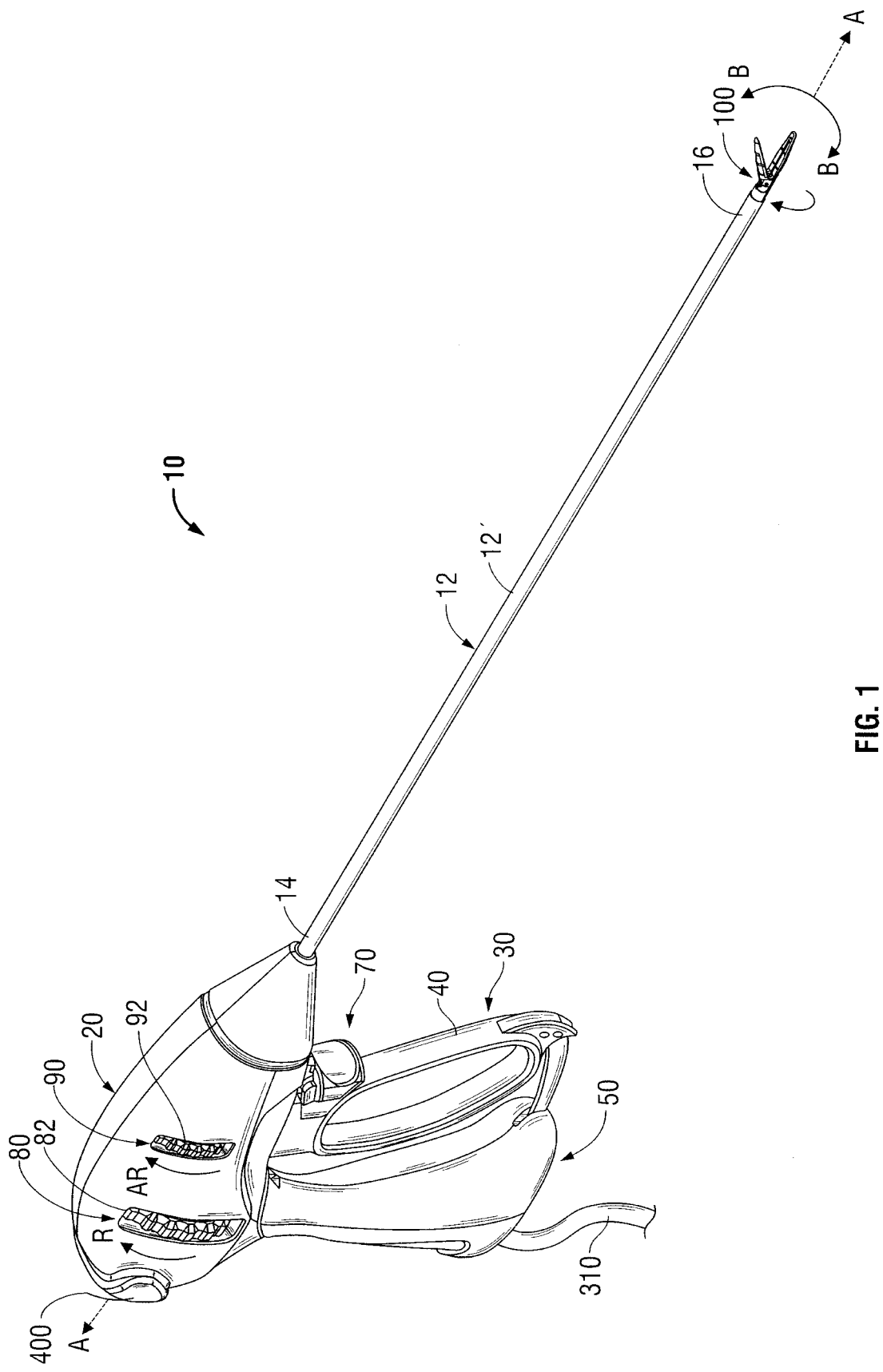
FIG. 1 is a perspective view of an endoscopic forceps showing a housing, a flexible shaft and an end effector assembly according to an embodiment the present disclosure.
Figure 2:
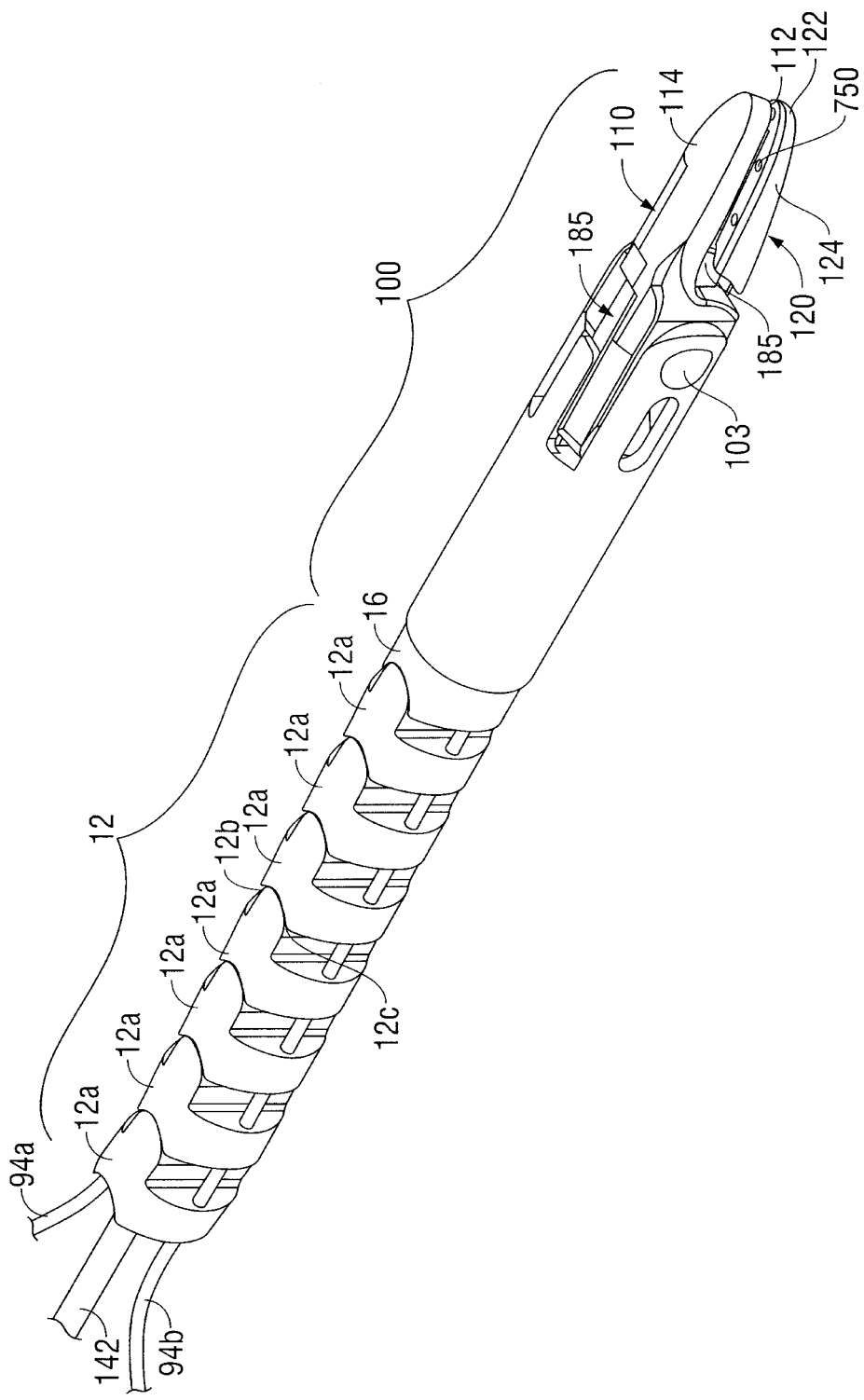
FIG. 2 is an enlarged front, perspective view of the flexible shaft (without an outer casing) and the end effector assembly of FIG. 1.
Figure 3:
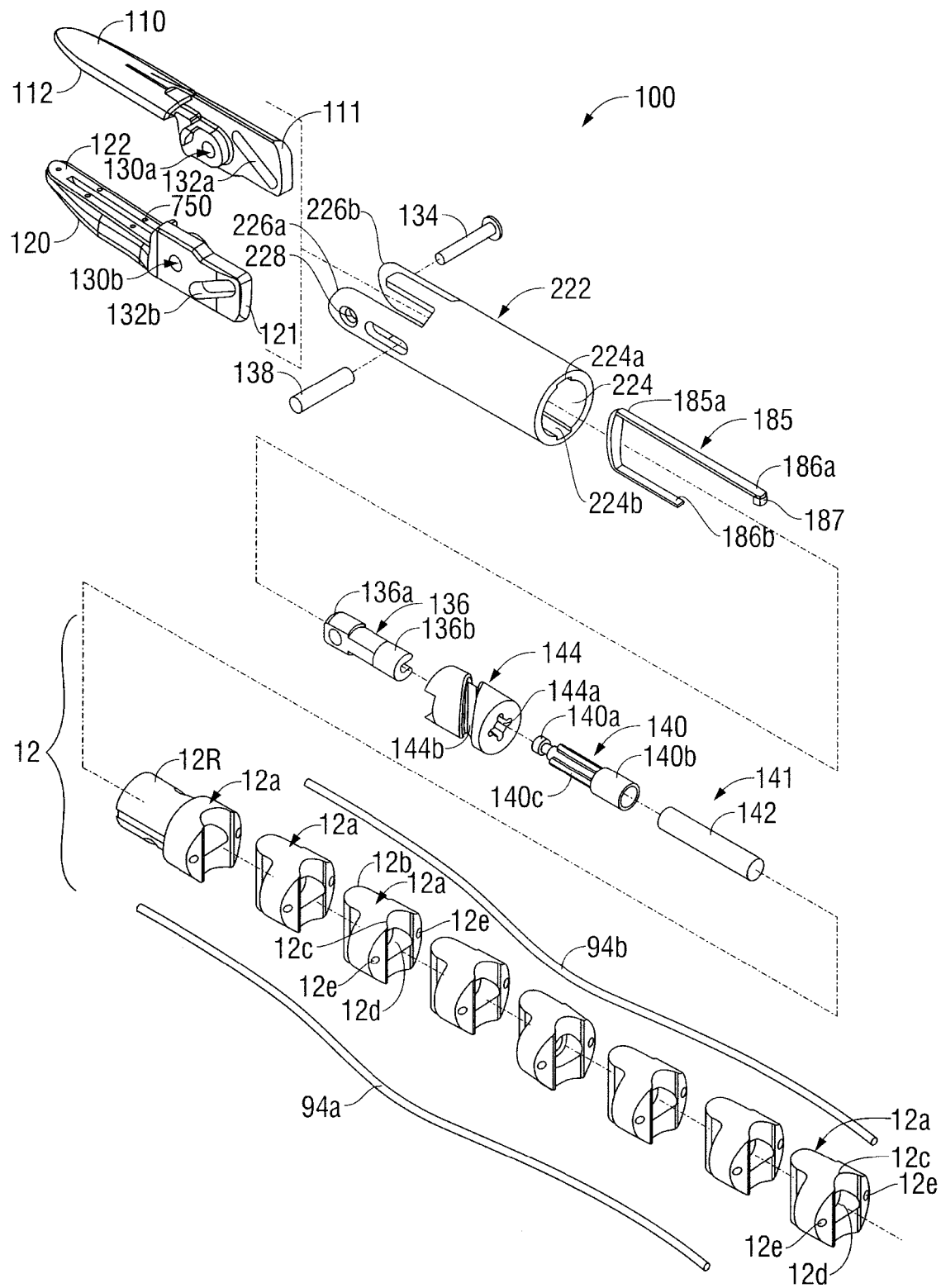
FIG. 3 is an enlarged rear, perspective view of the flexible shaft and end effector assembly with parts separated.

Turning now to FIGS. 1-3, one embodiment of an endoscopic vessel sealing forceps 10 is shown for use with various surgical procedures and generally includes a housing 20, a handle assembly 30, a rotating assembly 80, an articulation assembly 90, a trigger assembly 70 and an end effector assembly 100 which mutually cooperate to rotate, articulate, grasp, seal and divide tubular vessels and vascular tissue. Although the majority of the figures depict a bipolar sealing forceps 10 for use in connection with endoscopic surgical procedures, the present disclosure may be used for monopolar surgical procedures which employ a remote patient pad for completing the current loop.

Forceps 10 includes a generally flexible shaft 12 which has a distal end 16 dimensioned to mechanically engage the end effector assembly 100 and a proximal end 14 which mechanically engages the housing 20. In one embodiment, the shaft 12 has at least two portions, a proximal portion and a distal portion. The proximal portion of the shaft may be formed of a flexible tubing (e.g., plastic) and may incorporate a tube of braided steel to provide axial (e.g., compressional) and rotational strength. The distal portion of shaft 12 may be also be flexible, but may incorporate one or more moving joints. A casing 12' may be employed to protect a plurality of internal moving joints 12a of the flexible shaft 12.

In one embodiment, the proximal portion of the shaft is flexible and non-articulating while the distal portion of shaft 12 is capable of articulating in response to movement of articulation cables or wires. Details of how the shaft 12 flexes are described in more detail below with respect to FIGS. 8 and 9. The proximal end 14 of shaft 12 is received within the housing 20 and connected to the rotating assembly 80, articulating assembly 90 and drive assembly 150. In the drawings and in the descriptions which follow, the term "proximal," as is traditional, will refer to the end of the forceps 10 which is closer to the user, while the term "distal" will refer to the end which is farther from the user.

As best seen in FIG. 1, forceps 10 also includes an electrosurgical cable 310 which connects the forceps 10 to a source of electrosurgical energy, e.g., a generator (not shown). It is contemplated that generators such as those sold by Covidien-Energy-based Devices, located in Boulder, Colo. may be used as a source of electrosurgical energy, e.g., Covidien's LIGA-SURE™ Vessel Sealing Generator and Covidien's Force Triad™ Generator.

The generator may include various safety and performance features including isolated output, independent activation of accessories and/or so-called "Instant Response™" software which is a proprietary technology owned by Covidien. Instant Response™ is an advanced feedback system which senses changes in tissue 200 times per second and adjusts voltage and current to maintain appropriate power. The Instant Response™ technology is believed to provide one or more of the following benefits to vessel sealing: consistent clinical effect through all tissue types; reduced thermal spread and risk of collateral tissue damage; less need to "turn up the generator"; and designed for the minimally invasive environment.

Cable 310 is internally divided into cable lead 310a, 310b and 310c which each transmit electrosurgical energy through their respective feed paths through the forceps 10 to the end effector assembly 100 as explained in more detail below with respect to FIGS. 10 and 11.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 may be integrally associated with the housing 20 and is rotatable via rotating wheel 82 approximately 180 degrees in either direction about a longitudinal axis "A-A" defined through shaft 12. One envisioned rotating assembly 80 is disclosed in commonly-owned U.S. patent application Ser. No. 10/460,926, which has been incorporated by reference above. Another envisioned rotating assembly is disclosed in commonly-owned U.S. patent application Ser. No. 11/519,586, the entire content of which is incorporated by reference herein.

Articulation assembly 90 may also be integrally associated with housing 20 and operable via wheel 92 to move the end effector assembly 100 in the direction of arrows "B-B" relative to axis "A-A". Wheel 92 may be provided in alternative arrangements such as disposed on the side of housing. Also, wheel 92 may be replaced by other mechanisms to actuate the articulation assembly 90 such as a levers, trackballs, joysticks, or the like. Details relating to the articulation assembly 90 are explained in more detail below with reference to FIGS. 8 and 9.

As mentioned above, end effector assembly 100 is attached at the distal end 16 of shaft 12 and includes a pair of opposing jaw members 110 and 120. Movable handle 40 of handle assembly 30 is ultimately connected to a drive assembly 150 which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Turning now to the more detailed features of the present forceps housing 20, shaft 12 and end effector assembly 100, movable handle 40 is selectively movable about a pivot pin 29 from a first position relative to fixed handle 50 to a second position in closer proximity to the fixed handle 50 which, as explained below, imparts movement of the jaw members 110 and 120 relative to one another. The movable handle include a clevis 45 which forms a pair of upper flanges each having an aperture at an upper end thereof for receiving the pivot pin 29 therethrough. In turn, pin 29 mounts to opposing sides of the housing 20.

Clevis 45 also includes a force-actuating flange or drive flange (not shown) which aligns along longitudinal axis "A-A" and which abuts the drive assembly 150 such that pivotal movement of the handle 40 forces actuating flange against the drive assembly 150 which, in turn, closes the jaw members 110 and 120. A lower end of the movable handle 40 includes a flange 91 which is mounted to the movable handle 40 and which includes a t-shaped distal end 95 that rides within a predefined channel 51 disposed within fixed handle 50 to lock the movable handle 40 relative to the fixed handle 50.

The end effector assembly 100 includes opposing jaw members 110 and 120 which cooperate to effectively grasp tissue for sealing purposes. The end effector assembly 100 may be designed as a unilateral assembly, i.e., jaw member 120 is fixed relative to the shaft 12 and jaw member 110 pivots about a pivot pin 103 to grasp tissue or a bilateral assembly, i.e., both jaw members 110 and 120 move relative to axis "A-A". A drive rod 142 or drive sleeve is operably coupled to the drive assembly 150 and is selectively reciprocable via movement of handle 40 relative to handle 50 to actuate, i.e., pivot, the jaw members 110 and 120 relative to one another. In an embodiment of the device, drive rod 142 is flexible, and may be, for example, a cable.

In one particular embodiment according to the present disclosure and as best illustrated in FIGS. 1-3, a knife channel 115a and 115b may be defined in the upper and/or lower jaw member 110 and 120, respectively. The knife channel 115a and 115b is dimensioned to run through the center of the jaw members 110 and 120, respectively, such that a blade 185 may be selectively reciprocated to cut the tissue grasped between the jaw members 110 and 120 when the jaw members 110 and 120 are in a closed position. Blade 185 may be configured (or the blade 185 in combination with the end effector assembly 100 or drive assembly 150) such that the blade 185 may only be advanced through tissue when the jaw members 110 and 120 are closed thus preventing accidental or premature activation of the blade 185 through the tissue.

As best shown in FIGS. 2 and 3, jaw member 110 includes an insulative jaw housing 114 and an electrically conducive surface 112. Insulator 114 is dimensioned to securely engage the electrically conductive sealing surface 112 by stamping, by overmolding, by overmolding a stamped electrically conductive sealing plate and/or by overmolding a metal injection molded seal plate. All of these manufacturing techniques produce jaw member 110 having an electrically conductive surface 112 which is substantially surrounded by an insulative jaw housing 114. Jaw member 110 may also include one or more wire guides or channels (not shown) which are designed to guide cable lead 311 into electrical continuity with sealing surface 112.

Electrically conductive surface 112 and insulative jaw housing 114, when assembled, form a longitudinally-oriented slot 115a defined therethrough for reciprocation of the knife blade 185. It is envisioned that the knife channel 115a cooperates with a corresponding knife channel 115b defined in jaw member 120 to facilitate longitudinal extension of the knife blade 185 along a preferred cutting plane to effectively and accurately separate the tissue along the formed tissue seal.

Jaw member 120 includes similar elements to jaw member 110 such as an insulative jaw housing 124 and an electrically conductive sealing surface 122 which is dimensioned to securely engage the insulative jaw housing 124. Likewise, the electrically conductive surface 122 and the insulative jaw housing 124, when assembled, include a longitudinally-oriented channel 115a defined therethrough for reciprocation of the knife blade 185. As mentioned above, when the jaw members 110 and 120 are closed about tissue, knife channels 115a and 115b allow longitudinal extension of the knife 185 in a distal fashion to sever tissue along the tissue seal. A single knife channel, e.g., 115b, may be completely disposed in one of the two jaw members, e.g., jaw member 120, depending upon a particular purpose. Jaw member 120 may be assembled in a similar manner as described above with respect to jaw member 110.

Figure 7:
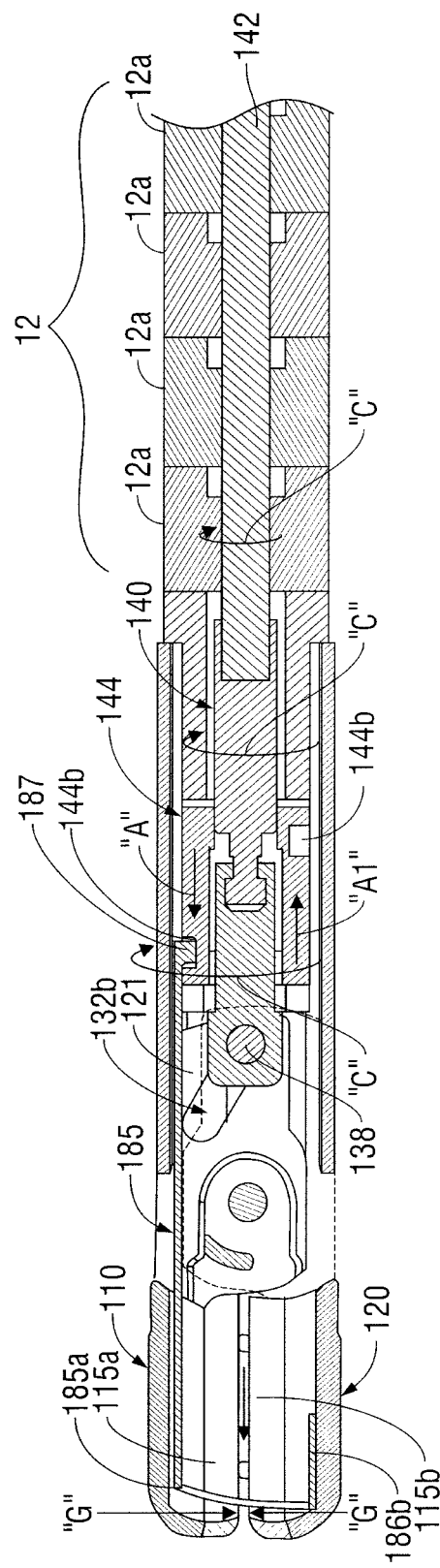
FIG. 7 is a side cross section of the flexible shaft and end effector of FIG. 2 showing distal translational movement of a cutting mechanism configured to cut tissue disposed within jaw members of the end effector assembly.

Jaw member 120 includes a series of stop members 750 disposed on the inner facing surfaces of the electrically conductive sealing surface 122 to facilitate gripping and manipulation of tissue and to define a gap "G" (see FIG. 7) between opposing jaw members 110 and 120 during sealing and cutting of tissue. The preferred gap "G" between the conductive sealing surfaces 112 and 122 to effectively and reliably seal tissue is between about 0.001 and about 0.006 inches. Stop members 750 may be employed on one or both jaw members 110 and 120 depending upon a particular purpose or to achieve a desired result. Stop members 750 may be thermally sprayed atop the electrically conductive sealing plate 122 or deposited or affixed in any other known fashion in the art. Moreover, the stop members 750 may be disposed in any configuration along the electrically conductive jaw surfaces 112 and 122 depending upon a particular jaw configuration or desired surgical result.

In one embodiment, jaw members 110 and 120 are engaged to the end of shaft 12 (or a sleeve (not shown) surrounding shaft 12) and are operable (via rotating assembly 80) to rotate about pivot 103 of the end effector assembly 100. Lead 311 carries a first electrical potential to jaw member 110 and a second electrical potential is transferred through drive rod 142 (or, alternatively, the above mentioned sleeve) to jaw member 120. Upon activation, the two electrical potentials transmit electrical energy through tissue held between conductive seal plates 112 and 122. Details relating to one envisioned electrical configuration of the lead 311 through forces 10 are discussed with reference to FIGS. 10 and 11 below.

Proximal movement of the drive rod 142 pivots the jaw members 110 and 120 to a closed position. More particularly, once actuated, handle 40 moves in a generally arcuate fashion towards fixed handle 50 about pivot pin 29 which forces clevis 45 to pull reciprocating drive rod 142 in a generally proximal direction to close the jaw members 110 and 120. Moreover, proximal rotation of the handle 40 causes the locking flange 71 to release, i.e., "unlock", the trigger assembly 70 for selective actuation of the knife 185.

The operating features and relative movements of the internal working components of one envisioned forceps 10, i.e., drive assembly 150, trigger assembly 70 and rotational assembly 80 are all described in commonly-owned U.S. patent application Ser. No. 10/460,926, the entire contents of which are incorporated by reference above.

Figure 4:
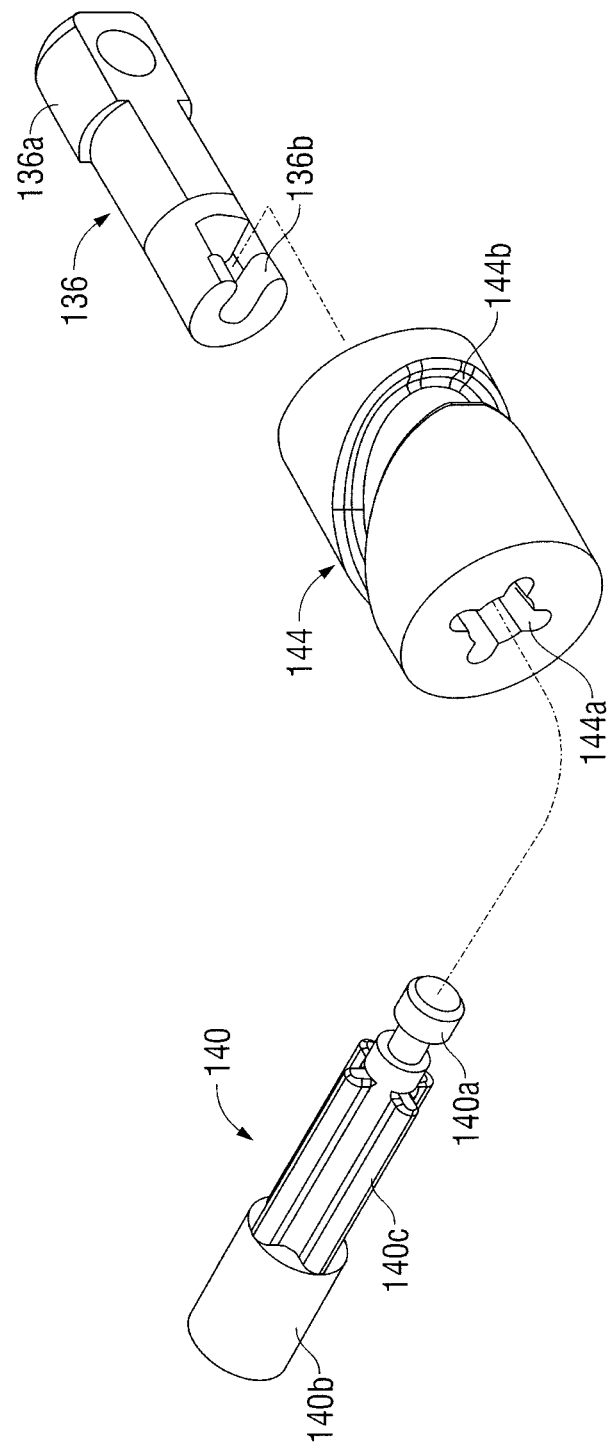
FIG. 4 is a greatly-enlarged perspective view of a cam mechanism of the end effector assembly.

As mentioned above, the jaw members 110 and 120 may be opened, closed, rotated and articulated to manipulate and grasp tissue until sealing is desired. This enables the user to position and re-position the forceps 10 prior to activation and sealing. As illustrated in FIG. 4, the end effector assembly 100 is rotatable about longitudinal axis "A-A" through rotation of the rotating knob 82 of rotating assembly 80. The end effector assembly 100 may also be articulated in either direction in the direction of arrows "B-B" as explained in more detail below with reference to FIGS. 8 and 9. Once the tissue is grasped (within the required pressure range of about 3 kg/cm$^2$ to about 16 kg/cm$^2$), the user then selectively applies electrosurgical energy to effectively seal tissue. Once sealed, the user then selectively advances the knife 185 by actuating the trigger assembly 70 to cut the tissue along the tissue seal.

The operating features and relative movements of one envisioned trigger assembly 70 are described in the above-mentioned commonly-owned U.S. patent application Ser. No. 10/460,926. In one embodiment, for example, actuation of the trigger assembly 70 causes a cable extending through shaft 12 and operatively coupled to knife 185 to move distally to thereby cut tissue along the tissue seal. In another embodiment, trigger assembly includes gearing that translates actuation of the trigger assembly to rotational motion of a cable extending through shaft 12.

One envisioned drive assembly 150 is also disclosed in U.S. patent application Ser. No. 10/460,926 which involves the selective reciprocation of a sleeve to open and close the jaw members 110 and 120. Another envisioned embodiment is described in U.S. application Ser. No. 11/519,586 wherein the drive assembly pulls a drive rod to open and close the jaw members 110 and 120.

With particular respect to FIGS. 2 and 3, the forceps 10 includes a plurality of joints 12a which are nestingly arranged in series to form flexible shaft 12. The distal end 16 of shaft 12 mechanically engages the end effector assembly 100 and the proximal end 14 of the shaft 12 mechanically engages the housing 20. Each of the plurality of joints 12a of the flexible shaft 12 includes a distal knuckle 12b and a proximal clevis 12c formed therewith. Each knuckle 12b operatively engages a clevis 12c of an adjacent joint 12a. Each joint 12a defines a central lumen 12d formed therein and a pair of opposed lumens 12e formed on either side of central lumen 12d. A pair of articulation cables 94a and 94b slideably extend through respective lumens 12e of joints 12. The operation of cables 94a and 94b is explained in further detail below with respect to FIGS. 8 and 9.

As seen in FIG. 3, end effector assembly 100 includes a jaw support member 222 which is configured to pivotably support jaw members 110 and 120. Jaw support member 222 defines a lumen 224 in a proximal end thereof and a pair of spaced apart arms 226a and 226b in a distal end thereof. Lumen 224 is configured and dimensioned to receive a stem 12f extending from a distal-most joint 12a of flexible shaft 12. Lumen 224 defines a pair of opposed channels 224a, 224b in a surface thereof which are configured to slidingly receive the knife blade 185 for reciprocation therein.

Jaws 110 and 120 are pivotably mounted on support member 222 by a jaw pivot pin 234 which extends through apertures 228 formed in arms 226a and 226b of support member 222 and respective pivot slots 132a, 132b formed in jaw members 110 and 120. To move jaws 110 and 120 between an open position and a closed position, an axially or longitudinally movable center rod 136 having a camming pin 138 is mounted within jaw support 222 at the center rod's 136 distal end 136a thereof. Camming pin 138 rides in and engages angled camming slots 132a and 132b formed in respective jaw members 110 and 120 such that axial or longitudinal movement of the center rod 136 via drive rod 142 causes jaws 110 and 120 to cam between open and closed positions.

End effector assembly 100 also includes a keyed rod 140 having a distal end 140a rotatably connected to a proximal end 136b of center rod 136. Keyed rod 140 includes a proximal end 140b fixedly connected to a distal end of drive rod 142, and a body portion 140c, disposed between distal end 140a and proximal end 140b, having a non-circular cross-sectional profile.

End effector assembly 100 further includes a camming assembly 141 including a camming hub 144 having a lumen 144a defined therethrough configured and adapted to slidably receive body portion 140c of keyed rod 140 therein. Camming hub 144 includes a mating mechanical interface defined therein which cooperates with the outer peripheral configuration of body portion 140c of keyed rod 140 to allow positive engagement of the two component halves for rotational purposes as explained in more detail below. The camming hub 144 also includes a helical or spiral groove 144b defined in an outer surface thereof which is configured to mechanically engage a detent 187 of the knife 185 the purpose of which is also explained in more detail below. Camming hub 144 is configured for rotatable disposition within lumen 124 of support member 222. In an alternative embodiment, camming hub 144 may be replaced by other mechanisms to translate rotational motion to linear motion (e.g., a lead screw, one or more gears, and the like).

Figure 5:
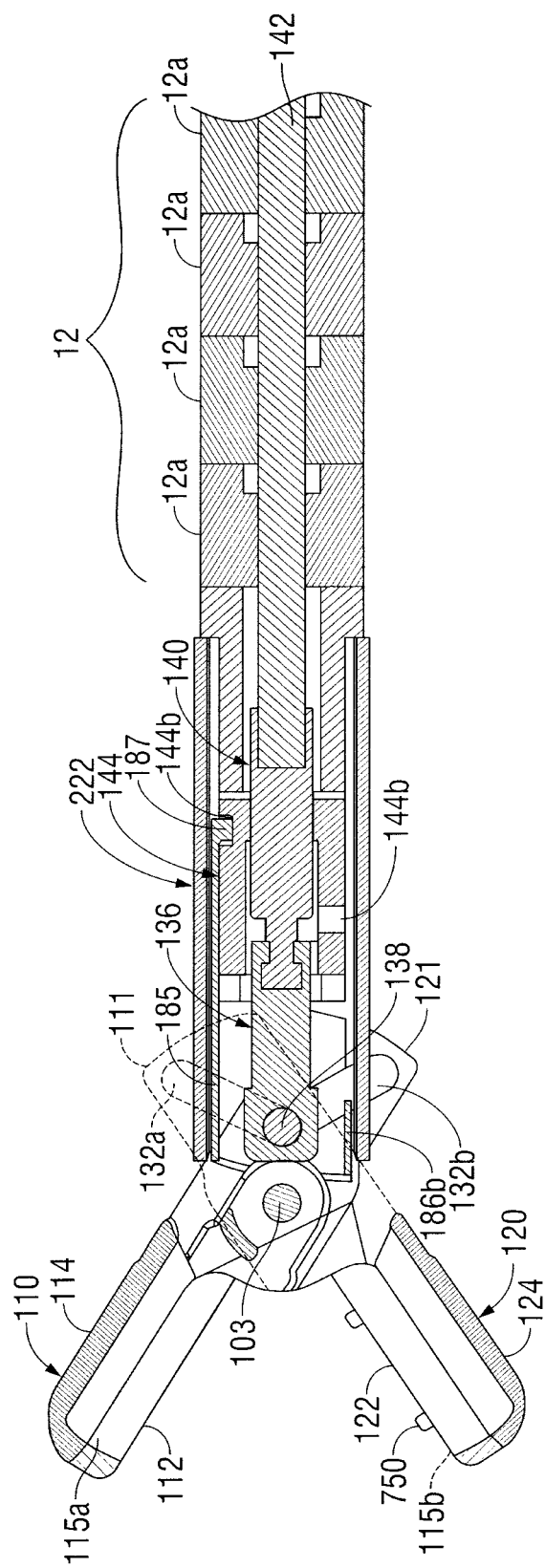
FIG. 5 is a side cross section of the flexible shaft and end effector assembly of FIG. 2 shown in an open configuration.
Figure 6:
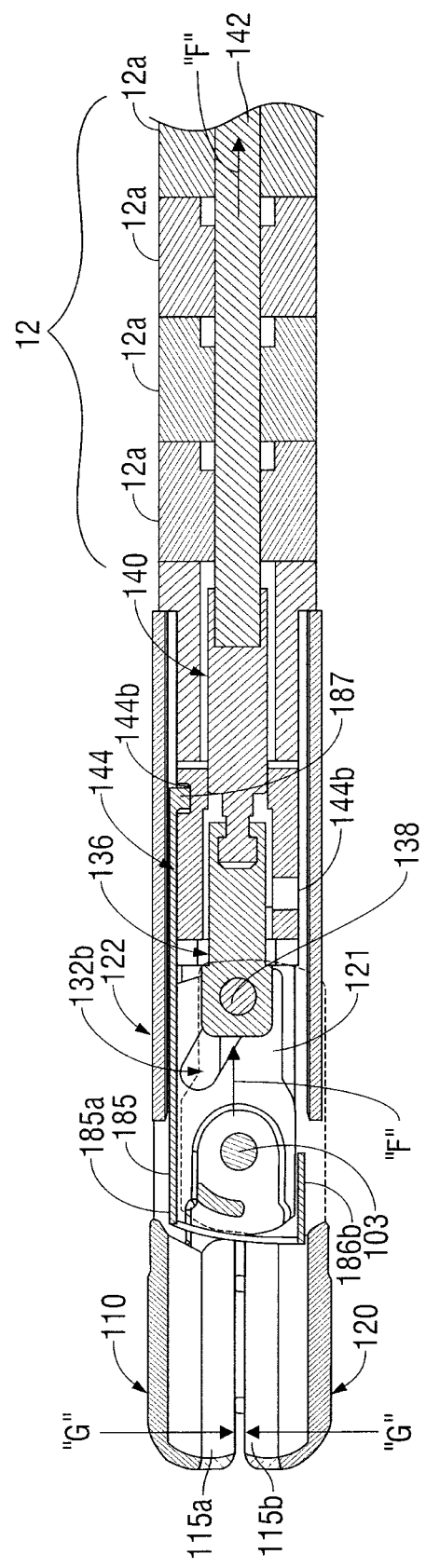
FIG. 6 is a side cross section of the flexible shaft and end effector assembly of FIG. 2 shown in a closed configuration.

In operation, the drive rod 142 is configured to provide two distinct and separate functions: axial displacement thereof actuates the jaw members 110 and 120 between the open to closed positions and rotational movement thereof advances the knife 185 through tissue. More particularly, axial displacement of drive rod 142 imparts axial displacement to keyed rod 140 which, in turn, imparts axial displacement to center rod 136. However, since camming hub 144 is axially slidably supported on keyed rod 140, no axial displacement is imparted thereto. As best shown in FIGS. 5 and 6, proximal translation of the drive rod 142 in the direction of arrow "F" forces camming pin 138 proximally within camming slots 132a and 132b to close the jaw members 110 and 120 about tissue with the requisite closure pressure and within the requisite gap "G" range. In an alternative embodiment (not shown), the functions actuated by drive rod 142 may be reversed with axial displacement advancing the knife 185 and rotational motion opening and closing jaw members 110 and 120. The electrically conductive sealing plates 112 and 122 are then energized to transmit electrical energy through tissue held between the jaw members 110 and 120.

One or more safety features may be employed either mechanically within the forceps 10 or electrically within the generator (not shown) to assure that tissue is effectively grasped between the jaw members 110 and 120 before energy is supplied.

Once a proper tissue seal is formed, the tissue may be severed along the tissue seal. Again, one or more safety features may be employed to assure that a proper seal has been formed prior to severing tissue. For example, the generator may include a safety lockout which electrically prevents or electro-mechanically prevents actuation of the knife 185 unless a proper and effective seal has been formed. As mentioned above, it is also important to note that vessel or tissue sealing is more than simply coagulating tissue and requires precise control of pressure, energy and gap "G" to effectively seal tissue.

The present disclosure incorporates a knife 185 which, when activated via the trigger assembly 70, progressively and selectively divides the tissue along an ideal tissue plane in precise manner to effectively and reliably divide the tissue into two sealed halves. The knife 185 allows the user to quickly separate the tissue immediately after sealing without substituting a cutting instrument through a cannula or trocar port. As can be appreciated, accurate sealing and dividing of tissue is accomplished with the same forceps 10.

It is envisioned that knife blade 185 may also be coupled to the same or an alternative electrosurgical energy source to facilitate separation of the tissue along the tissue seal. Moreover, it is envisioned that the angle of the knife blade tip 185a may be dimensioned to provide more or less aggressive cutting angles depending upon a particular purpose. For example, the knife blade 185 may be positioned at an angle which reduces "tissue wisps" associated with cutting. Moreover, the knife blade 185 may be designed having different blade geometries such as serrated, notched, perforated, hollow, concave, convex etc. depending upon a particular purpose or to achieve a particular result. It is envisioned that the knife 185 generally cuts in a progressive, uni-directional fashion (i.e., distally). As mentioned above, the drive rod performs two functions, opening and closing the jaw members 110 and 120 and advancing the knife 185 to sever tissue (see FIG. 7). In order to sever the tissue, rotation of drive rod 142 imparts rotation to keyed rod 140 which, in turn, imparts rotation to camming hub 144. However, since keyed rod 140 is rotatably connected to center rod 136, no rotation is imparted thereto.

End effector assembly 100 is operably coupled to a knife 185 which is slidably supported within respective channels 224a and 224b of support member 222. More particularly, knife 185 includes a sharpened or serrated edge 185a at a distal end thereof and a pair of guide flanges 186a and 186b which extend proximally therefrom. The proximal end of flange 186a includes a detent or protrusion 187 which is configured to engage and ride within spiral or helical groove 144b defined in camming hub 144.

In operation, as camming hub 144 is rotated in direction of arrow "C", proximal end 187 rides within groove 144b of camming hub 144 and moves in an axial direction "A1" relative thereto. Rotation of the camming hub 144 in one direction forces the blade 185 distally through knife channels 115a and 115b in jaw members 110 and 120, respectively, to sever tissue disposed therebetween. Rotation in the opposite direction forces proximal end 187 proximally to retract blade 185 to a proximal-most position. A spring may be operatively associated with the camming hub 144 to bias the knife 185 in a proximal-most orientation.

Figure 8:
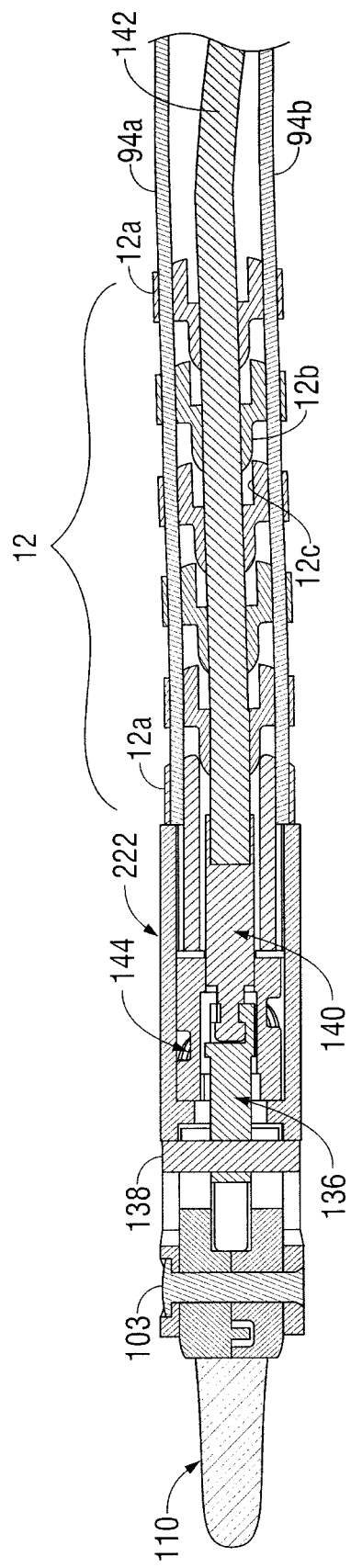
FIG. 8 is a longitudinal, cross-sectional view of the end effector assembly of FIG. 2 in an un-articulated condition.

As mentioned above, the end effector assembly 100 may also be selectively articulated. More particularly, as seen in FIG. 8 with end effector assembly 100 in an axially aligned condition, in order to articulate end effector assembly 100 via articulation assembly 90, wheel 92 is configured to rotate in a first direction to move end effector assembly 100 in a corresponding first direction and rotate in an opposite direction to move end effector assembly 100 in an opposite direction. Various pulley assemblies and gearing assemblies may be employed to accomplish this purpose.

For example, in one embodiment, the handle assembly may include at least one articulation cable operable from the housing. Each articulation cable includes a distal end operatively connectable with an end effector and a proximal end operatively connected to at least one of a control element, such as, for example, a slider, dial, lever, or the like, supported on the housing. In operation, movement of the control element results in movement of the at least one articulation cable, wherein movement of the at least one articulation cable in a first direction causes an articulation of the end effector and movement of the at least one articulation cable in a second direction results in articulation of the end effector in a second direction.

A pair of articulation cables may be provided each having a proximal end operatively connected to the control element such that movement of the control element in a first direction results in movement of a first articulation cable in a first direction and movement of a second articulation cable in a second direction; and movement of the control element in a second direction results in movement of the first articulation cable in the second direction and movement of the second articulation cable in the first direction.

Figure 9:
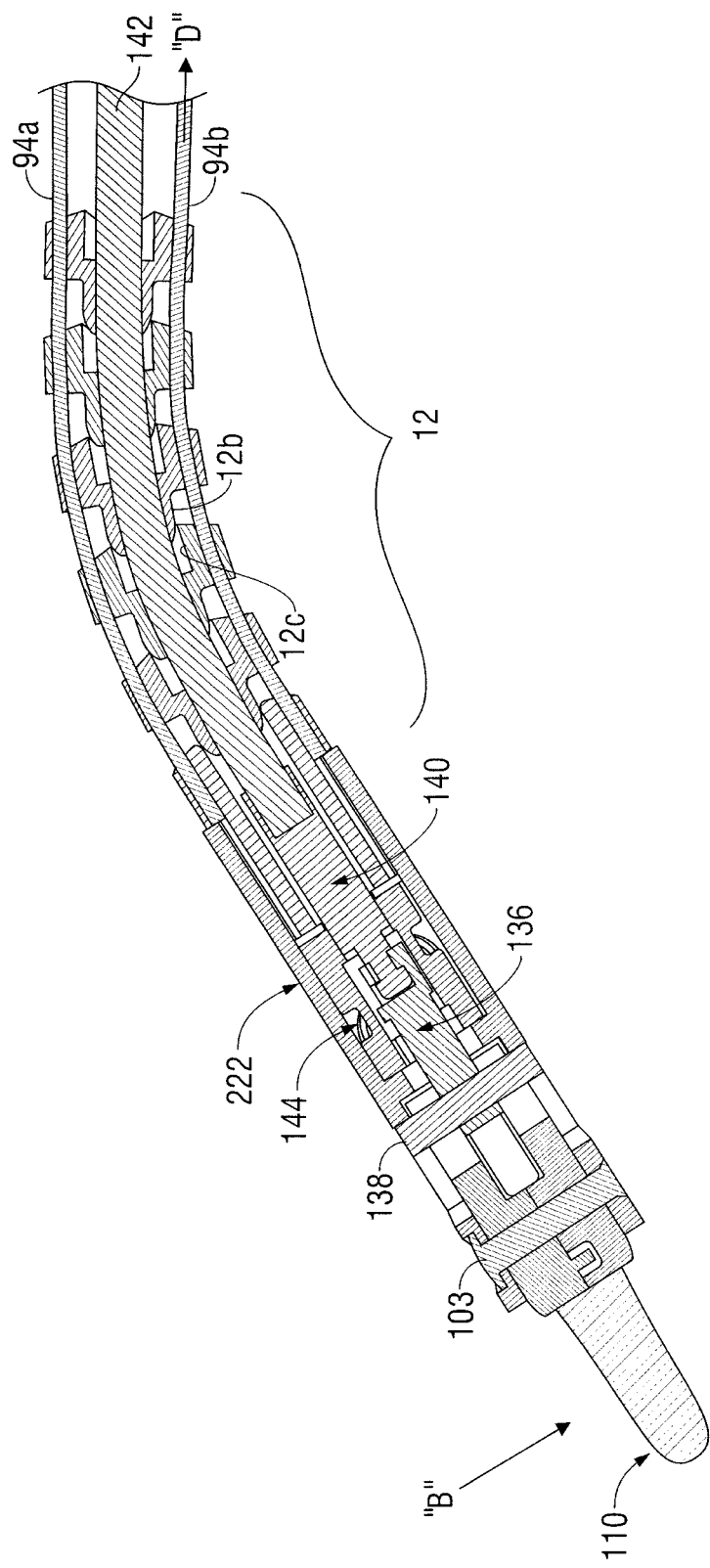
FIG. 9 is a longitudinal, cross-sectional view of the end effector assembly of FIG. 2 in an articulated condition.

More particularly and with reference to FIGS. 8 and 9, when first articulation 94b cable (i.e., the lower articulation cable as depicted in FIGS. 8 and 9) is withdrawn in a proximal direction via wheel 92, as indicated by arrow "D" of FIG. 9, a distal end of articulation cable 94b, anchored to a distal-most joint 12a, rotates about the interface between knuckles 112b and clevis' 112c thereby causing gaps defined therebetween, along a side surface thereof, to constrict. In so doing, end effector assembly 100 is articulated in a downward direction, in the direction of arrow "B", i.e., in a direction transverse to longitudinal axis "A-A". In order to return end effector assembly 100 to an un-articulated condition or to articulate end effector assembly 100 in an opposite direction, articulation cable 94a (i.e., the upper articulation cable as depicted in FIGS. 8 and 9) may be withdrawn in a proximal direction by rotation of wheel 92 in an opposite direction.

Various handles and/or handle assemblies may be operatively connected or otherwise associated with end effector assembly 100 in order to effect operation and movement of the various components thereof, i.e., drive cable 142 and/or articulation cables 94a, 94b. Exemplary handles and/or handle assemblies for use with end effector 1100 are disclosed in U.S. Provisional Application Ser. No. 60/849,562 filed on Oct. 5, 2006, entitled "PROGRAMMABLE HANDLE ASSEMBLY FOR SURGICAL DEVICES"; and U.S. Provisional Application Ser. No. 60/849,560 filed on Oct. 5, 2006, entitled "HANDLE ASSEMBLY FOR ARTICULATED ENDOSCOPIC INSTRUMENTS", the entire disclosures of each of which being incorporated herein by reference.

Figure 10:
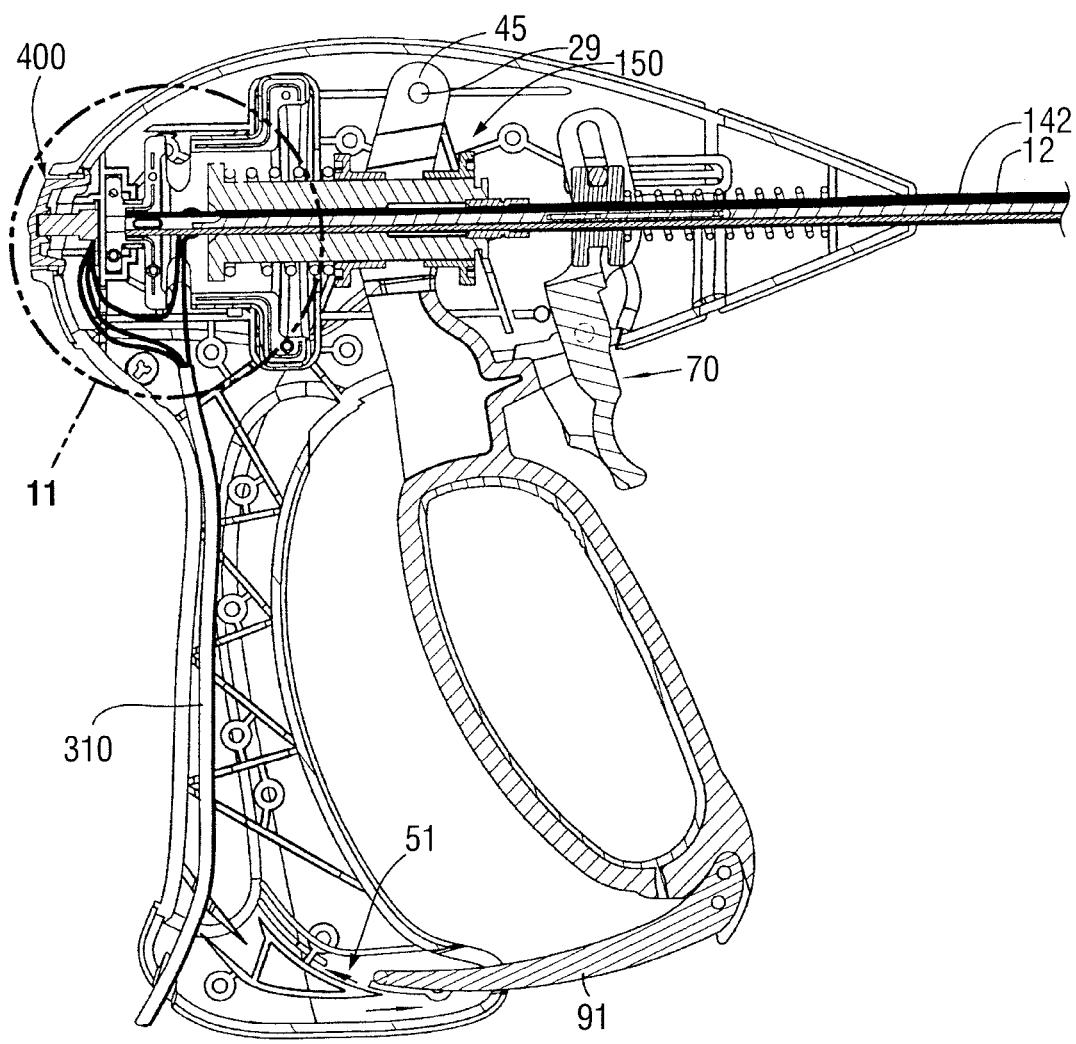
FIG. 10 is a cross-section of the housing showing the internal, electrical routing of an electrosurgical cable and electrical leads.
Figure 11:
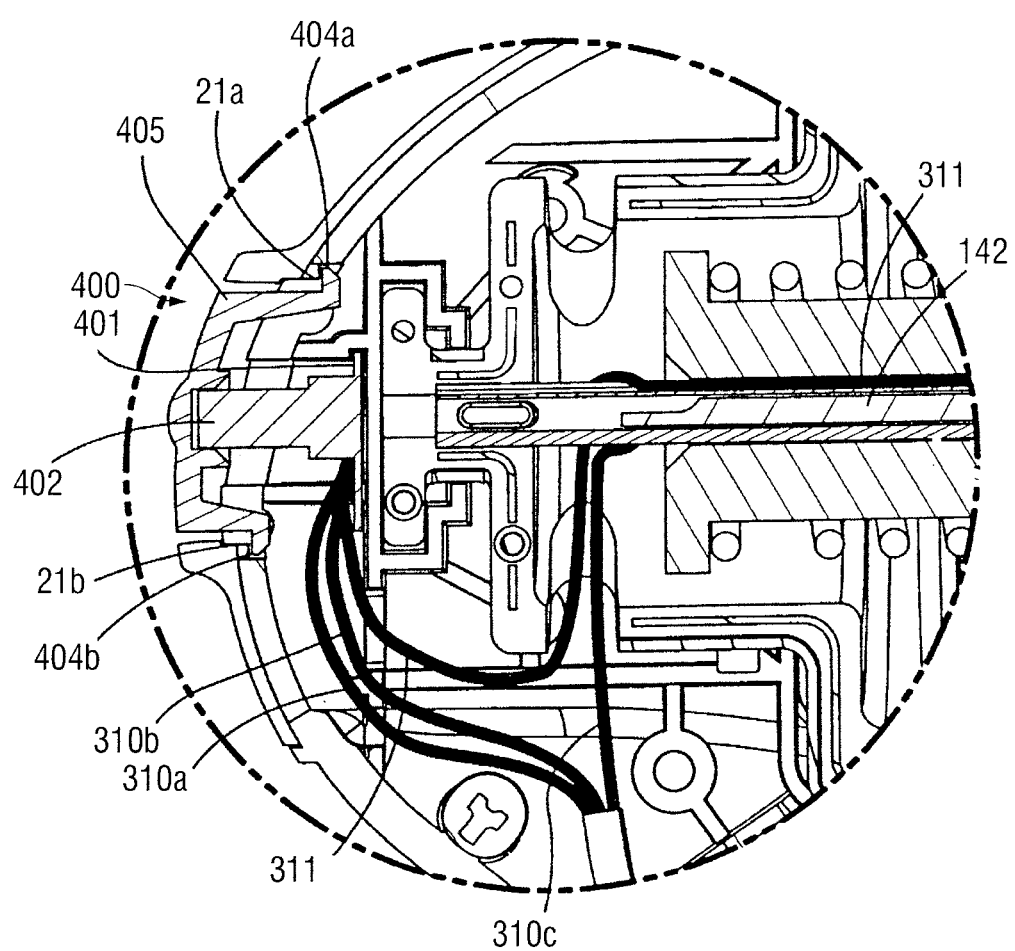
FIG. 11 is a greatly-enlarged view of the indicated area of detail of FIG. 10.
Figure 12:
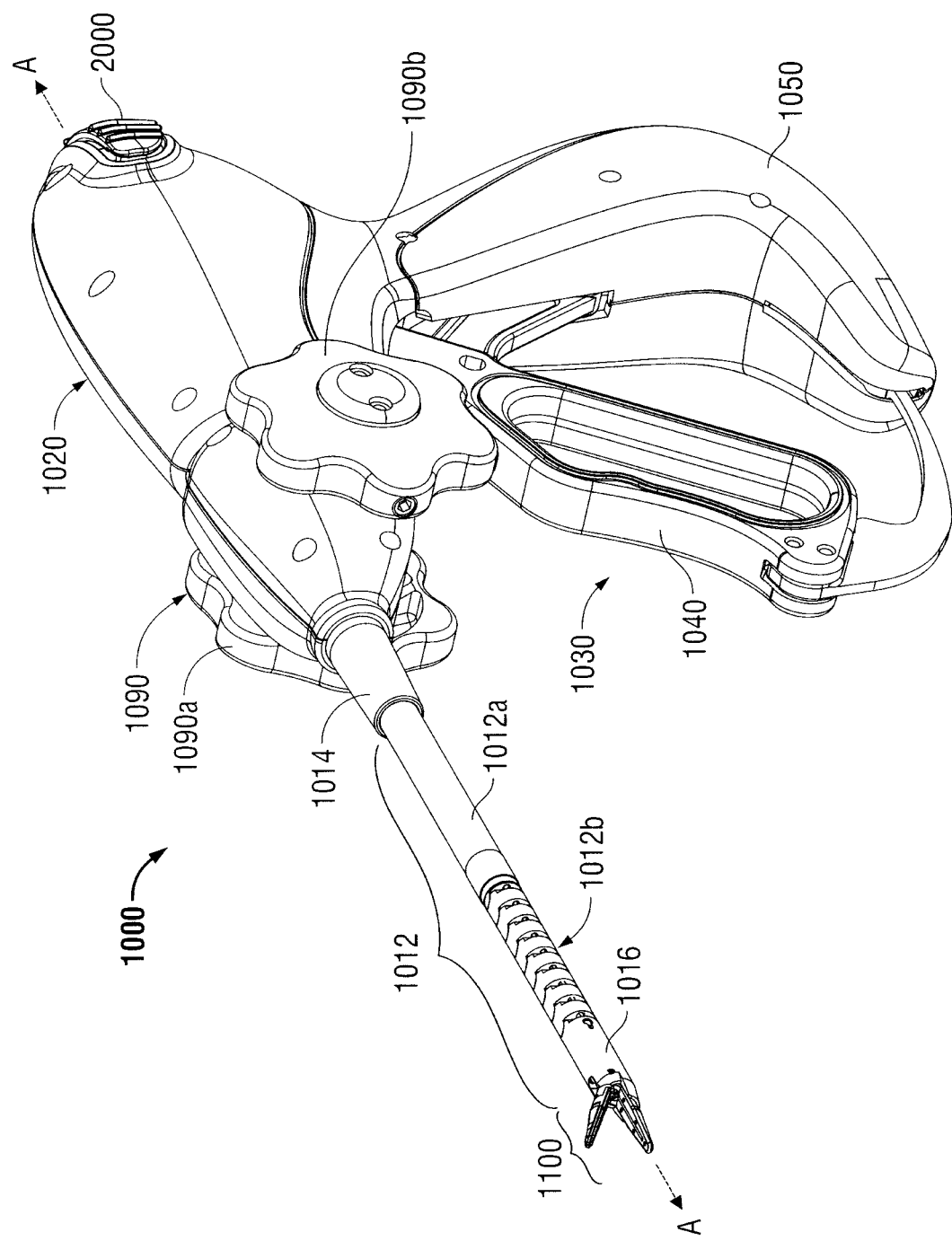
FIG. 12 is a perspective view of another embodiment of an endoscopic forceps showing a housing, a partially flexible shaft and an end effector assembly according to the present disclosure.
Figure 13:
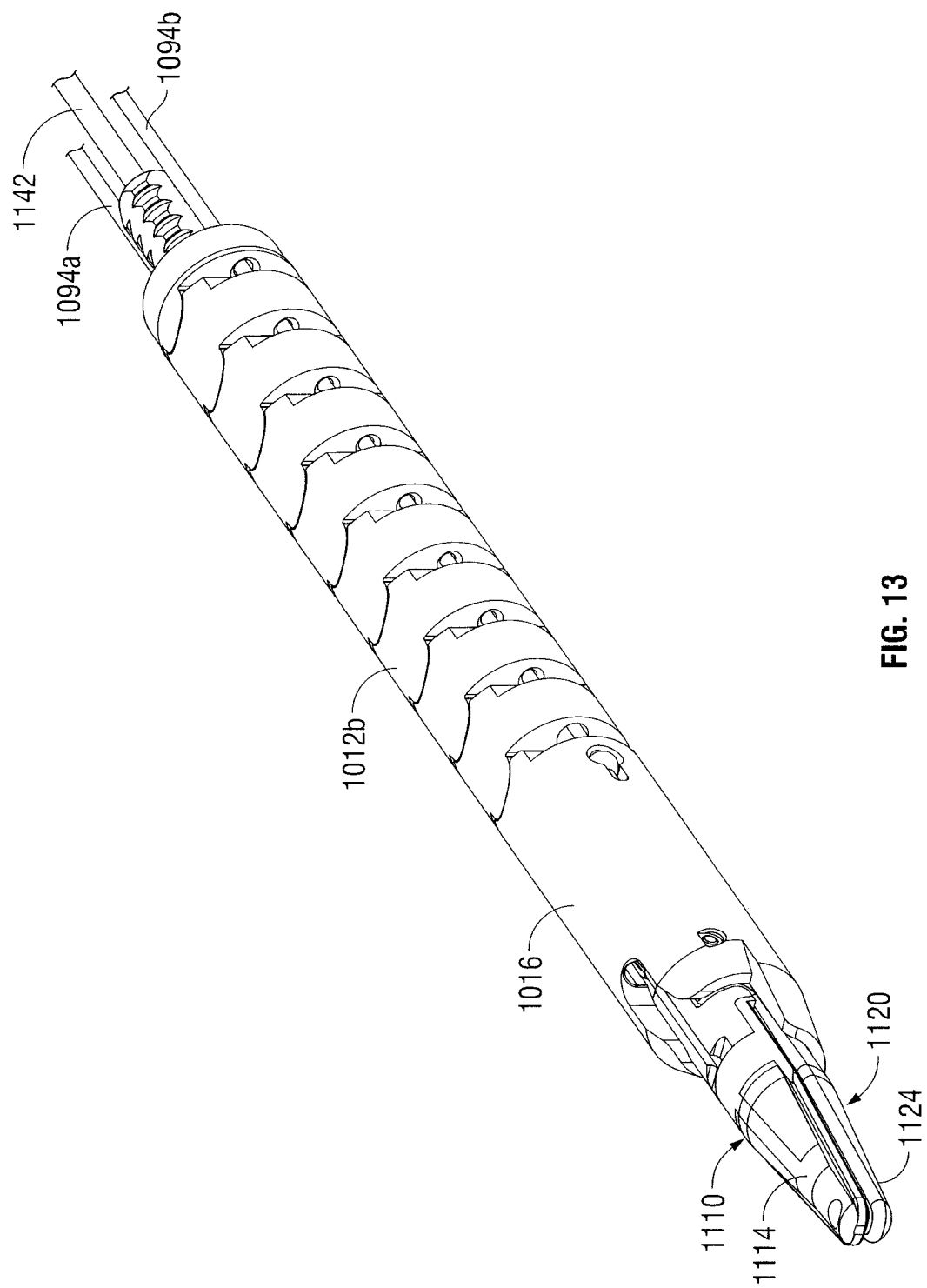
FIG. 13 is an enlarged perspective view of the partially flexible shaft of FIG. 12.

FIGS. 10 and 11 show one envisioned embodiment wherein the electrical leads 310a, 310b, 310c and 311 are fed through the housing 20 by electrosurgical cable 310. More particularly, the electrosurgical cable 310 is fed into the bottom of the housing 20 through fixed handle 50. Lead 310c extends directly from cable 310 into the rotating assembly 80 and connects (via a fused clip or spring clip or the like) to drive rod 142 to conduct the second electrical potential to jaw member 120. Leads 310a and 310b extend from cable 310 and connect to the hand switch or joy-stick-like toggle switch 400

In one embodiment, switch 400 may include an ergonomically dimensioned toggle plate 405 which may conform to the outer shape of housing 20 (once assembled). It is envisioned that the switch 400 permits the user to selectively activate the forceps 10 in a variety of different orientations, i.e., multi-oriented activation. As can be appreciated, this simplifies activation. A pair of prongs 404a and 404b extend distally and mate with a corresponding pair of mechanical interfaces 21a and 21b disposed within housing 20. Toggle plate 405 mechanically mates with a switch button 402 which, in turn, connects to an electrical interface 401. The electrical leads 310a and 310b are electrically connected to electrical interface 401. When the toggle plate 405 is depressed, trigger lead 311 carries the first electrical potential to jaw member 110. More particularly, lead 311 extends from interface 401 through the rotating assembly 80 and along a portion of shaft 12 to eventually connect to the jaw member 110. Lead 310c connects directly to either drive shaft 142 which ultimately connects to jaw member 120 or may be configured to extend directly to jaw member 120 to carry the second electrical potential.

It is envisioned that a safety switch or circuit (not shown) may be employed such that the switch cannot fire unless the jaw members 110 and 120 are closed and/or unless the jaw members 110 and 120 have tissue held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. U.S. patent application Ser. No. 10/427,832 describes one such feedback system, the entire contents of which being incorporated by reference herein.

As mentioned above, at least one jaw member, e.g., 120, may include a stop member 750 which limits the movement of the two opposing jaw members 110 and 120 relative to one another. In one embodiment, the stop member 750 extends from the sealing surface 122 a predetermined distance according to the specific material properties (e.g., compressive strength, thermal expansion, etc.) to yield a consistent and accurate gap distance "G" during sealing. It is envisioned for the gap distance between opposing sealing surfaces 112 and 122 during sealing ranges from about 0.001 inches to about 0.006 inches and, more preferably, between about 0.002 and about 0.003 inches. In one embodiment, the non-conductive stop members 750 are molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 750. Several thermal spraying techniques are contemplated which involve depositing a broad range of heat resistant and insulative materials on various surfaces to create stop members 750 for controlling the gap distance between electrically conductive surfaces 112 and 122.

FIGS. 15-21 show an alternate embodiment of an electrosurgical articulating forceps 1000 for use with vessel sealing procedures. May of the aforedescribed features of forceps 1000 are similar to forceps 10 and for the purposes of consistency, these features are hereby incorporated in the following discussion of forceps 1000 which is discussed below in a more abbreviated form.

Operation of forceps 1000 is similar to forceps 10 and includes movable handle 1040 which is movable relative to the fixed handle 1050. Movable handle 1040 is selectively moveable about a pair of pivots 1047 and 1057 (See FIG. 14C) from a first position relative to fixed handle 1050 to a second position in closer proximity to the fixed handle 1050 which, as explained below, imparts movement of the jaw members 1110 and 1120 relative to one another. In turn, each pivot 1047 and 1057 mounts to a respective housing half 1020a and 1020b.

Handle 1040 is operatively coupled to a pair of linkages 1042 and 1045 which upon movement of handle 1040 impart corresponding movement to the drive assembly 1700 as explained in more detail below. The arrangement of the handles 1040 and 1050, pivots 1047 and 1057 and linkages 1042 and 1045 provide a distinct mechanical advantage over conventional handle assemblies and allows the user to gain lever-like mechanical advantage to actuate the jaw members 1110 and 1120. This reduces the overall amount of mechanical force necessary to close the jaw members 1110 and 1120 to effect a tissue seal.

Much like the embodiment described with respect FIGS. 1-14, the lower end of the movable handle 1040 includes a flange 1044 which includes a t-shaped distal end 1044' that rides within a predefined channel 1051 disposed within fixed handle 1050. The t-shaped distal end 1044' lock the movable handle 1040 relative to the fixed handle 1050 and as explained in more detail below.

Figure 14A:
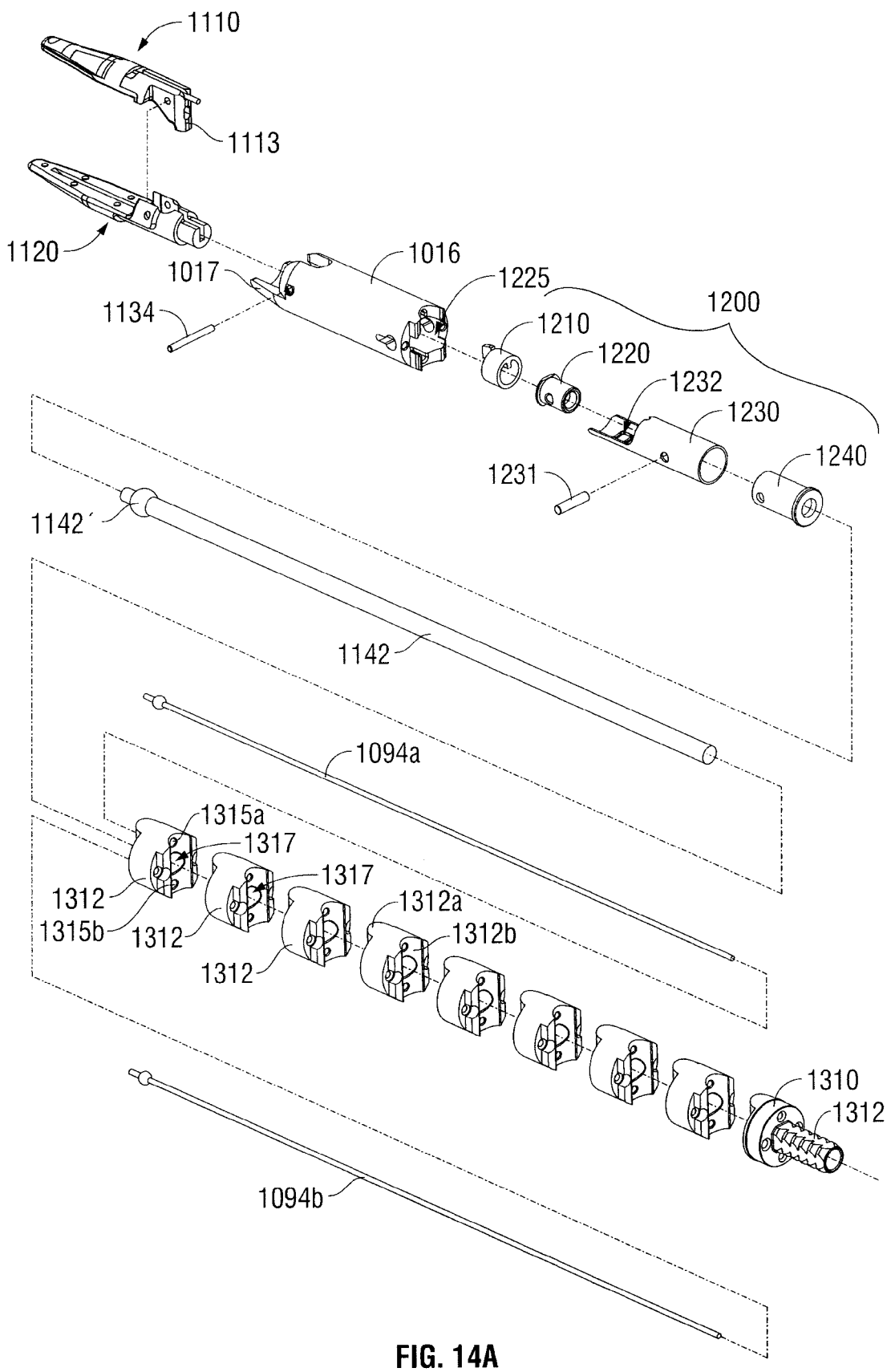
FIG. 14A is an enlarged, exploded perspective view of the partially flexible shaft of FIG. 13.

End effector assembly 1100 includes opposing jaw members 1110 and 1120 which cooperate to effectively grasp tissue for sealing purposes. The end effector assembly 1100 is designed as a unilateral assembly, i.e., jaw member 1120 is fixed relative to the shaft 1012 and jaw member 1110 pivots about a pivot pin 1134 to grasp tissue. More particularly, the unilateral end effector assembly 1100 includes one stationary or fixed jaw member 1120 mounted in fixed relation to the shaft 1012 and pivoting jaw member 1110 mounted about a pivot pin 1134 attached to the stationary jaw member 1120. A reciprocating sleeve 1230 is slidingly disposed within the shaft 1012 and is remotely operable by the drive assembly 1700. The pivoting jaw member 1110 includes a detent or protrusion 1113 which extends from jaw member 1110 through an aperture 1232 disposed within the reciprocating sleeve 1230 (FIG. 14A). The pivoting jaw member 1110 is actuated by sliding the sleeve 1230 axially within the shaft 1012 such that a distal end of the aperture 1232 abuts against the detent 1113 on the pivoting jaw member 1110 (See FIGS. 16A-17B). Pulling the sleeve 1230 proximally closes the jaw members 1110 and 1120 about tissue grasped therebetween and pushing the sleeve 1230 distally opens the jaw members 1110 and 1120 relative to one another for grasping purposes.

Unilateral end effector assembly 1100 may be structured such that electrical energy can be routed through the sleeve 1230 at the protrusion 1113 contact point with the sleeve 1230 or using a "brush" or lever (not shown) to contact the back of the moving jaw member 1110 when the jaw member 1110 closes. In this instance, the electrical energy would be routed through the protrusion 1113 to one of the jaw members 1110 or 1120. Alternatively, an electrical cable lead 1455 may be routed to energize one of the jaw members, e.g., jaw member 1120, and the other electrical potential may be conducted through the sleeve 1230 via electrical contact with lead 1450 (See FIG. 16C) and transferred to the pivoting jaw member 1110 which establishes electrical continuity upon retraction of the sleeve 1230.

Jaw members 1110 and 1120 include similar elements to jaw members 110 and 120 as described above such as jaw insulators 114 and 124 and electrically conductive sealing surfaces 112 and 122 (See FIG. 13), respectively. Jaw member 1120 also includes a series of stop members 750 (See FIG. 16B) disposed on the inner facing surface of electrically conductive sealing surface 1122 to facilitate gripping and manipulation of tissue and to define a gap "G" (See FIG. 17A) between opposing jaw members 1110 and 1120 during sealing and/or cutting of tissue. It is envisioned that the series of stop members 750 may be employed on one or both jaw members 1110 and 1120 in a variety of configurations depending upon a particular purpose or to achieve a desired result.

Articulation assembly 1090 is operatively coupled to housing 1020. Articulation wheels 1090a and 1090b may be provided in alternative arrangements such as disposed on the side of housing 1020. It is envisioned that wheels 1090a and 1090b may be replaced by other mechanisms to actuate the articulation assembly 1090 such as a levers, trackballs, joysticks, or the like.

Figure 18A:
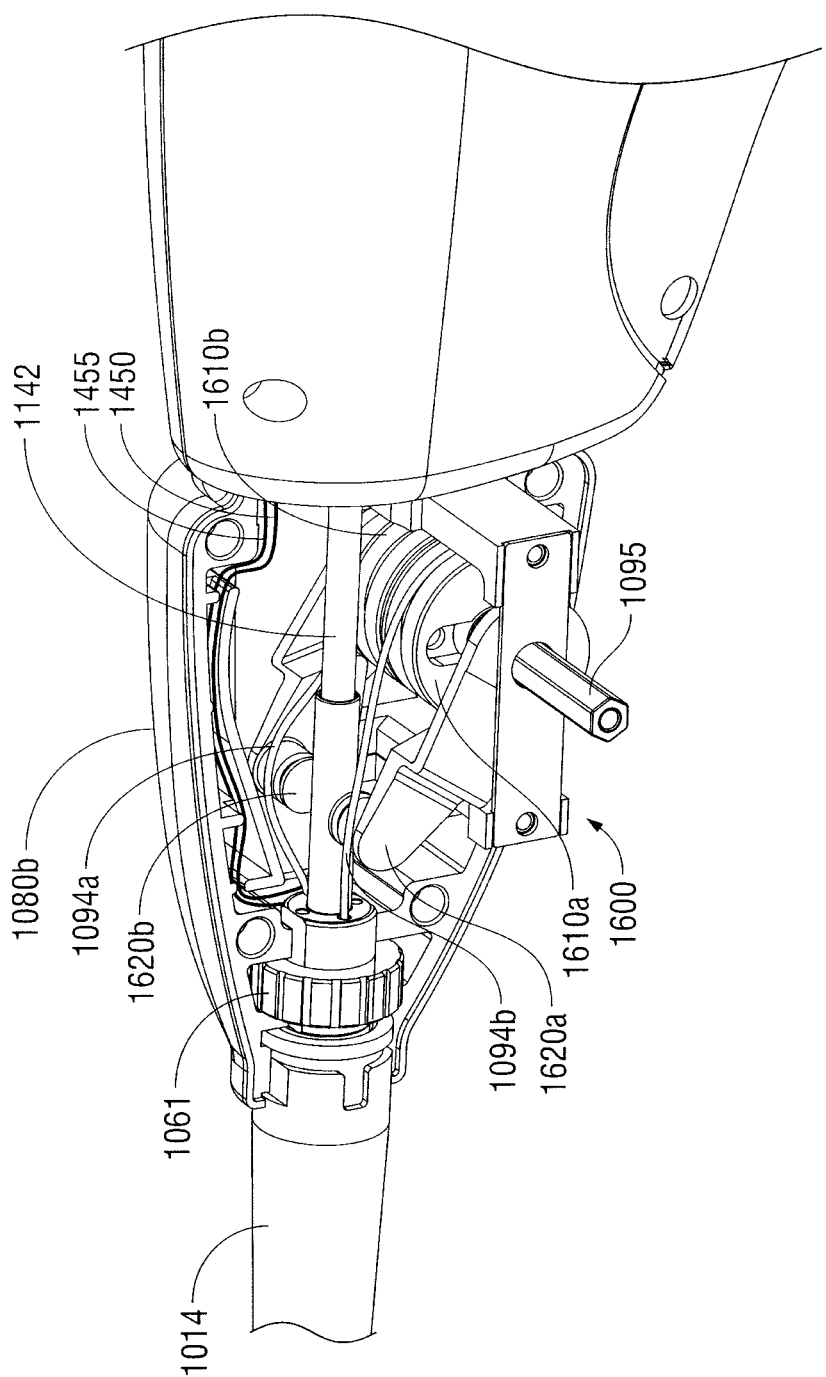
FIG. 18A is an enlarged internal perspective of an articulation assembly in accordance with the present disclosure.
Figure 18B:
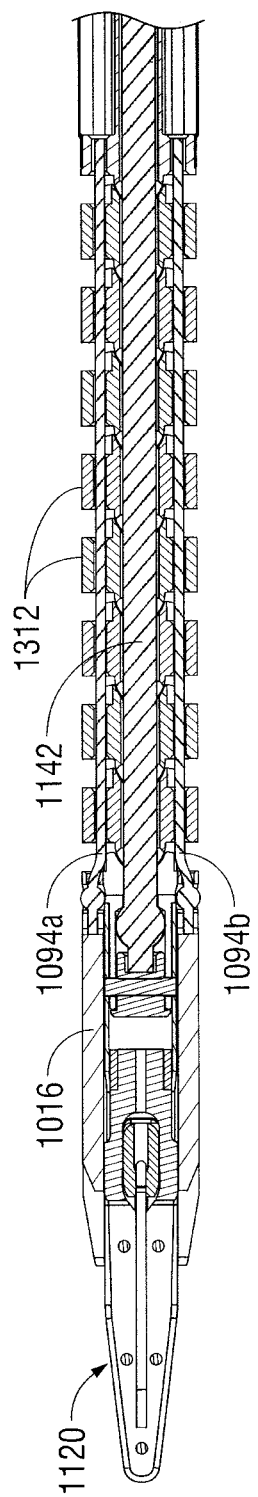
FIG. 18B is a top cross section of the partially flexible shaft of FIG. 13 in an aligned, non-articulated orientation.
Figure 18C:
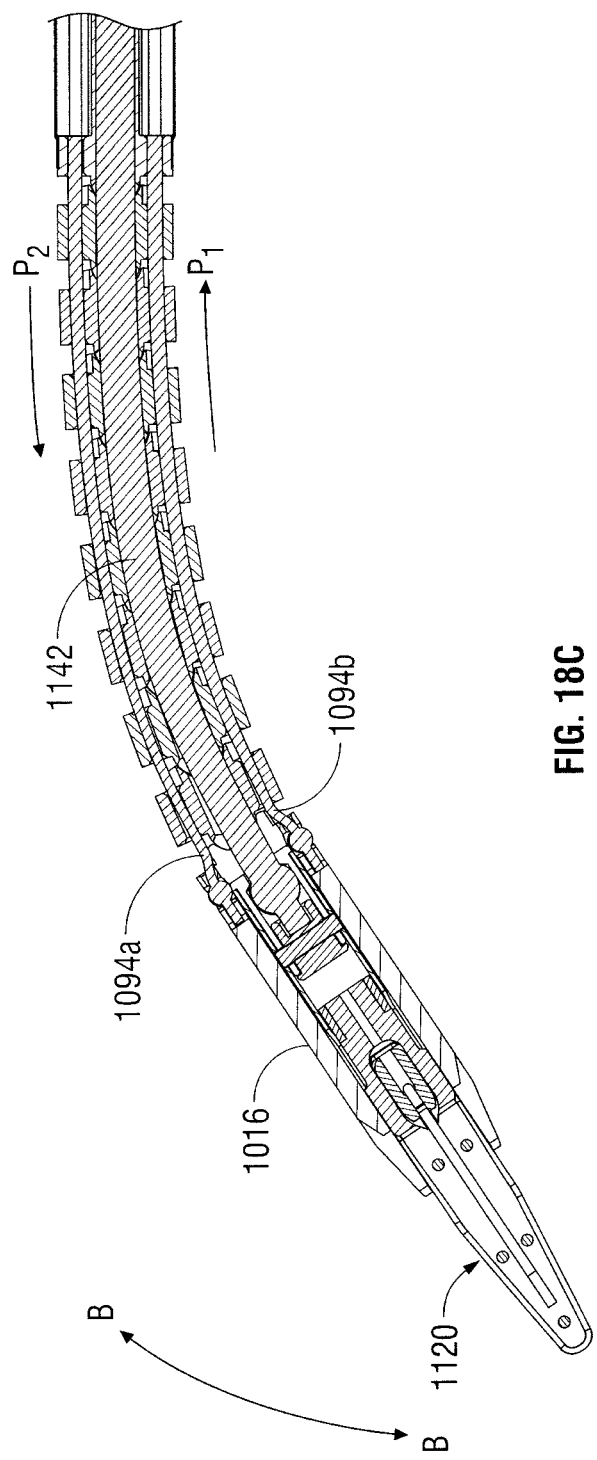
FIG. 18C is a top cross section of the partially flexible shaft of FIG. 13 in an articulated orientation.

More particularly, as seen in the comparison of FIGS. 18A-18C upon selective rotation of one of the wheels 1090a, 1090b, the end effector assembly 1100 may be articulated from an axially aligned condition (FIG. 18B) to an articulated condition (FIG. 18C). In order to articulate end effector assembly 1100 via articulation assembly 1090, wheels 1090a and 1090b are configured to rotate in a first direction to move end effector assembly 1100 in a corresponding first direction and rotate in an opposite direction to move end effector assembly 1100 in an opposite direction. Various pulley assemblies and gearing assemblies may be employed to accomplish this purpose.

For example and similar to the articulation arrangement described above, two articulation cables 1094a and 1094b may be utilized to articulate the flexible portion 1012b of shaft 1012. As best seen in FIG. 16C, each articulation cable 1094a and 1094b includes a distal end 1094a' and 1094b' which operatively connects with an end effector coupling assembly 1016 disposed at the distal end of shaft 1012. Coupling assembly 1016 includes a cavity 1225 defined therein configured to receive a series of mechanically inter-cooperating elements which are designed to engage the drive rod 1142 for reciprocation therein as well as guide the various electrical connections to the jaw members 1110 and 1120. The drive rod 1142 is preferably made from a flexible, friction-reducing material to allow the drive rod 1142 to bend in a given direction when the forceps 1000 is articulated. The friction-reducing material reduces buckling during articulation.

Coupling assembly includes a pair of bushings 1220 and 1240 which engage and secure a distal end 1142' of the drive rod 1142 to the drive sleeve 1230 via pin 1231. Bushing 1240 is slidingly engaged atop drive rod 1142 proximal to end 1142' and bushing 1220 is configured to engage bushing 1240 and secure end 1142' therebetween. Pin 1231 couples the secured bushings 1240 and 1220 and drive rod 1142 to drive sleeve 1230. The drive sleeve 1230 (and secured drive rod 1142) is received within cavity 1225 for sliding translation therein upon actuation of the drive assembly 1700 as explained in more detail below.

Coupling assembly 1016 also includes a locking element 1210 which is configured to engage a proximal end 1117 of jaw member 1120 to lock the coupling assembly 1016 (and drive rod 1142) in fixed relation relative to jaw member 1120 to limit any rotational movement therebetween. The coupling assembly 1016 also includes a distal flange 1017 which supports the lower jaw member 1120 once assembled (See FIG. 14A). As best shown in FIG. 16C, the coupling assembly 1016 also supports the electrical connection between lead 1450 and driving sleeve 1230. In addition, coupling assembly 1016 also guides electrical lead 1455 (shown in phantom) therethrough for connection to jaw member 1110.

In operation, movement of one of the articulation wheels 1090a and 1090b results in movement of the articulation cables 1094a and 1094b in opposite directions. More particularly, and as best shown in FIGS. 14C, 18A, 20A and 20B, the articulation assembly 1090 include wheels 1090a and 1090b which matingly couple to corresponding gear members 1096a and 1096b disposed on respective sides of housing 1020a and 1020b (See FIG. 20A). A hexagonal axle 1095 is mounted through both gear members 1096*a* and 1096*b* and capped on either end by wheels 1090*a* and 1090*b*. The axle 1095 is secured within the gear members 1096*a* and 1096*b* by mechanically mating surfaces (friction fit, geometric fit, etc.) or in other ways customary in the trade. The gear-like arrangement of the wheels 1090*a* and 1090*b* allow for incremental indexing of the articulation member 1090 in a given direction and a pair of set springs 1091 on each wheel prevent recoil of the wheel in any given direction. In other words, the set springs 1091 are configured to intermesh with the gears, e.g., gear 1096*b*, and allow incremental advancement in a clockwise or counter-clockwise direction. The biasing force of the set springs 1091 against the gear, e.g., gear 1096*b*, is sufficient to maintain the flexible shaft 1012*b* in any desired articulated position.

Axle 1095 supports pulley assembly 1600 within housing 1020 in operative association with cables 1094*a* and 1094*b*. More particularly, pulley assembly 1600 includes two pulleys 1610*a* and 1610*b* mounted for rotation atop axle 1095. Each pulley 1610*a* and 1610*b* includes a corresponding guide sleeve 1620*a* and 1620*b* which guide the respective cable 1094*a* and 1094*b* atop the corresponding pulley 1610*a* and 1610*b* to facilitate reciprocation thereof. As best shown in FIG. 18A, cable 1094*a* is designed to engage pulley 1620*b* for rotation one direction, while cable 1094*b* is designed to engage pulley 1620*a* for rotation in the opposite direction. As can be appreciated, this enables the pulleys 1610*a* and 1610*b* to operate in a push-pull manner to articulate the flexible shaft 1012*b*. In other words, as one cable 1094*a* is being pulled in the direction of P1, the other cable 1094*b* is being pushed (or relaxed) in the direction of P2 to allow the flexible shaft 1012*b* to articulate in a given direction (See FIG. 18C). The guide sleeves 1620*a* and 1620*b* also pre-tension the respective cables 1094*b* and 1094*a* to facilitate and enhance consistent articulation of the flexible shaft 1012*b*.

Figure 14B:
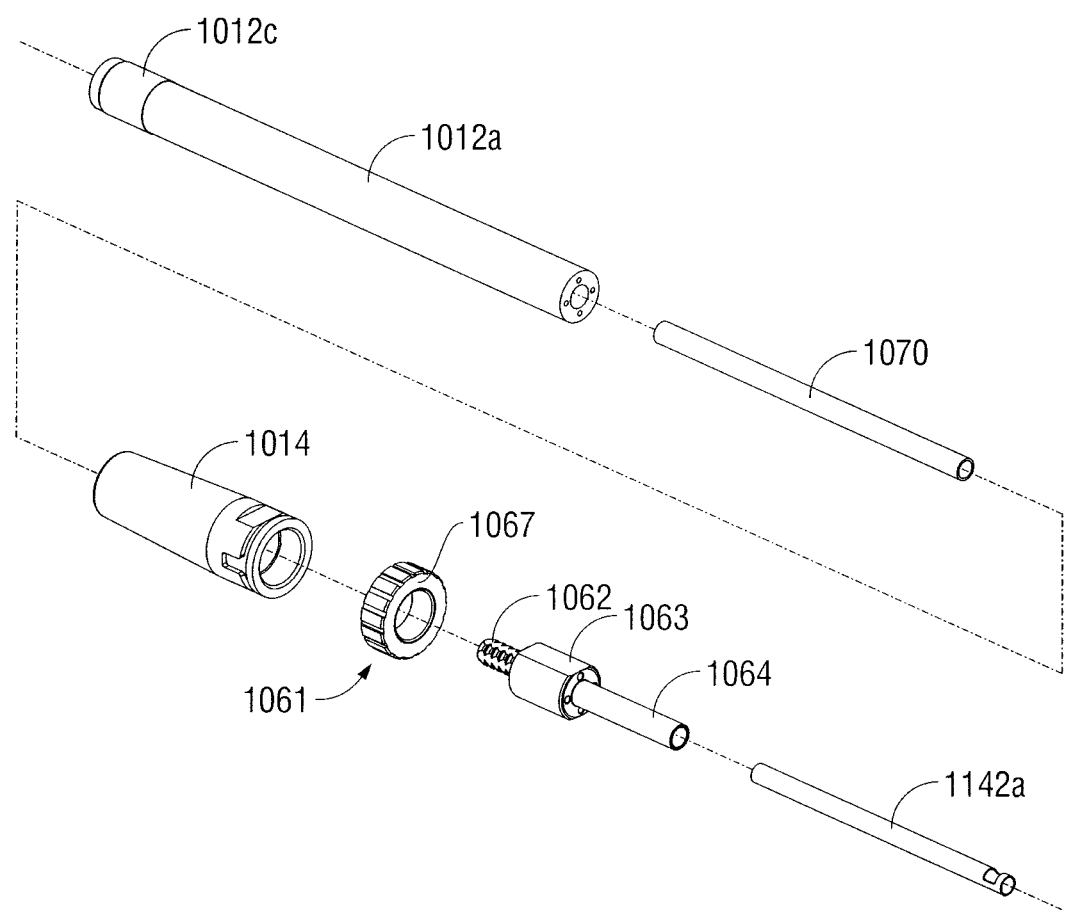
FIG. 14B is a greatly enlarged perspective view of a fine adjustment mechanism of according to the present disclosure.
Figure 14C:
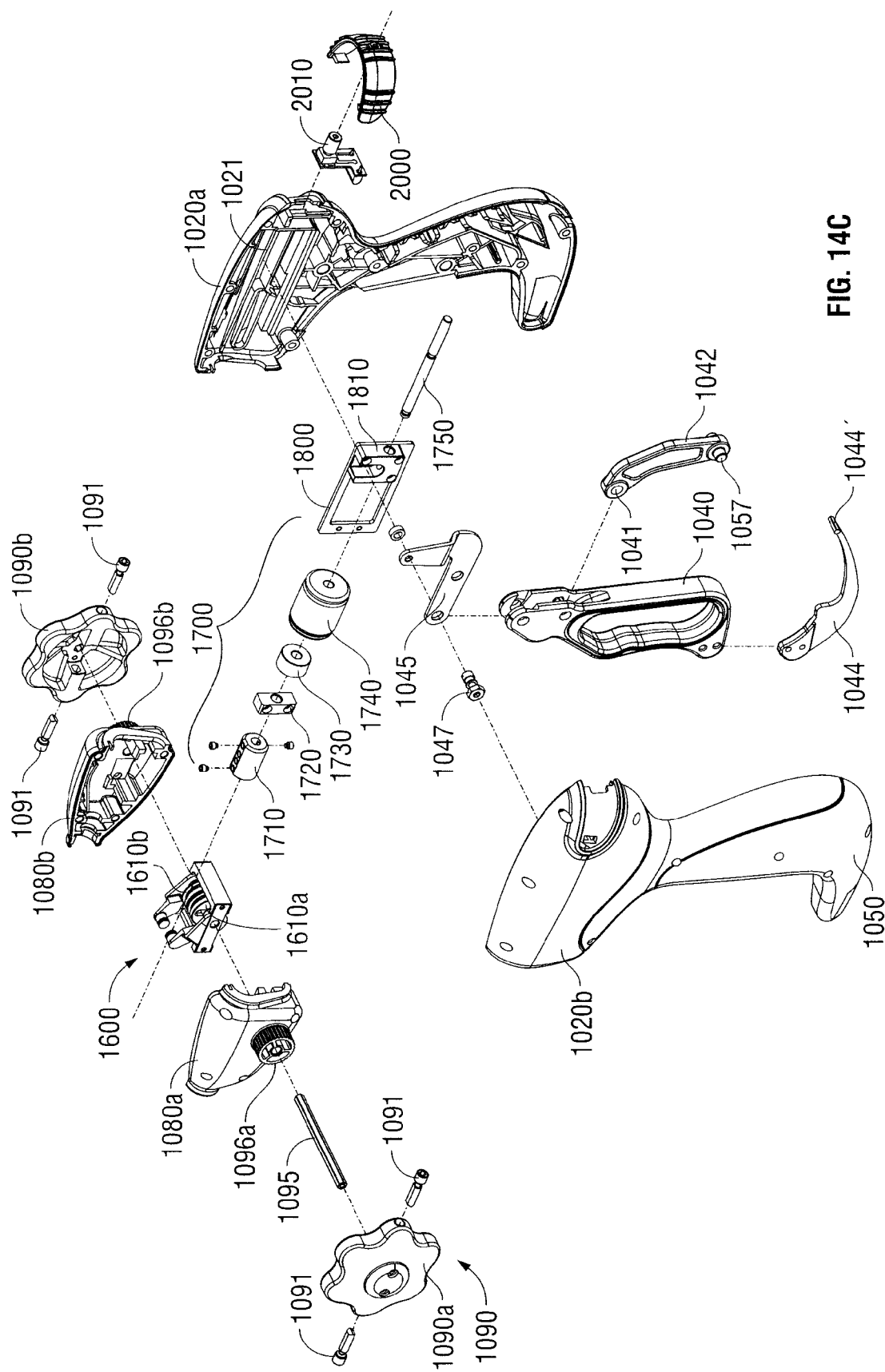
FIG. 14C is an exploded perspective view of the housing of the forceps of FIG. 12.
Figure 15A:
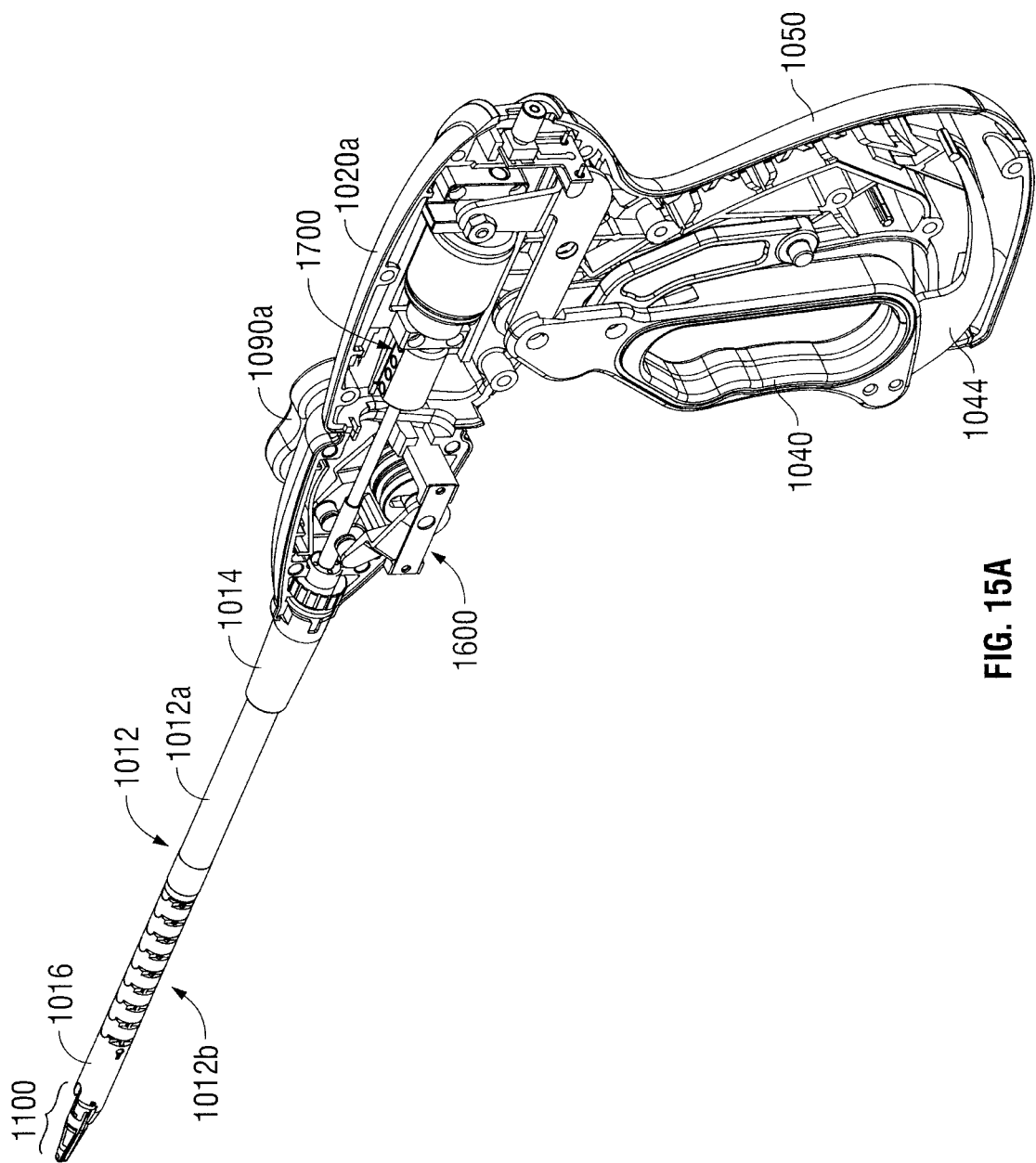
FIG. 15A is a rear perspective of the housing showing various internal components disposed therein.
Figure 15B:
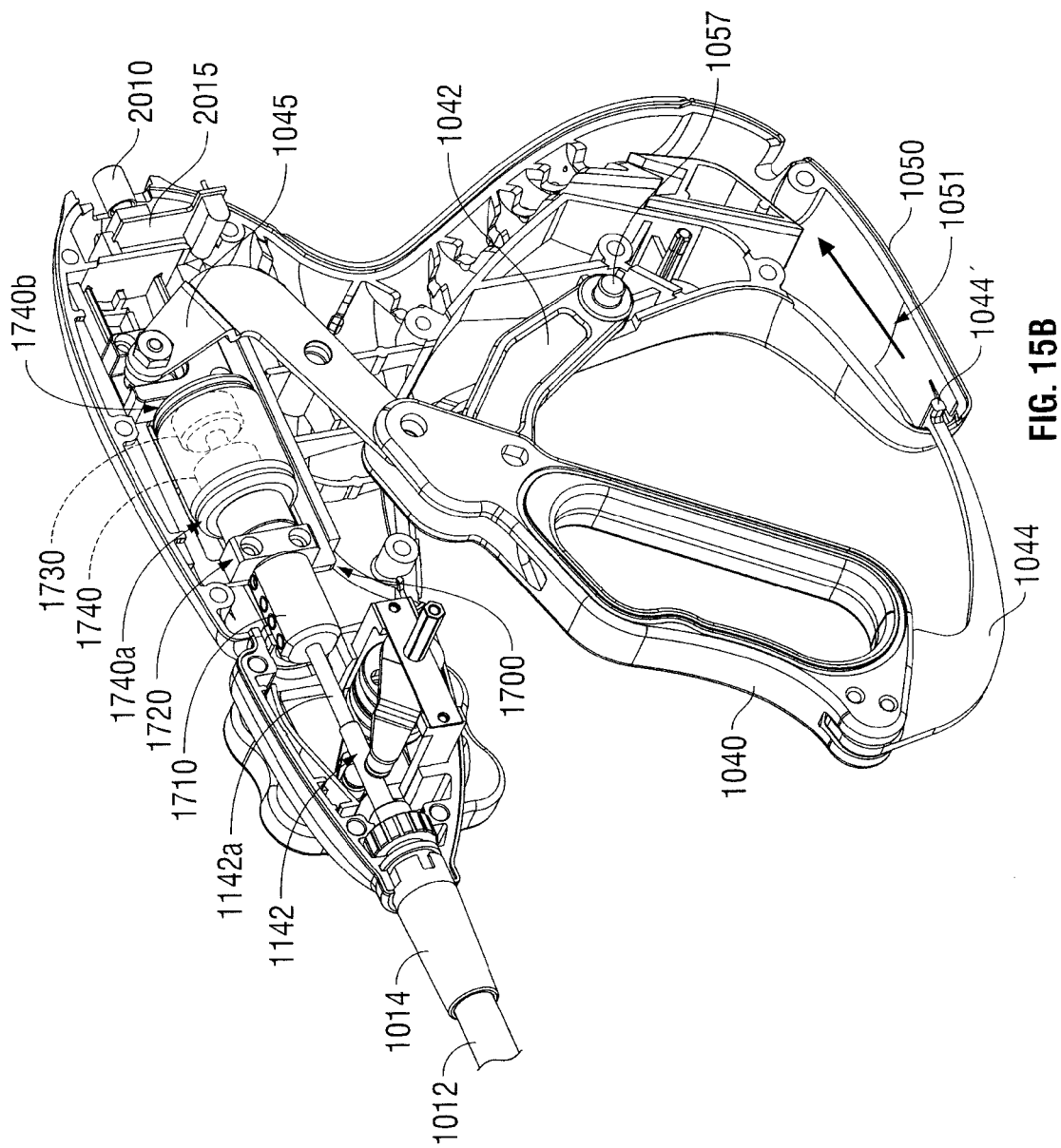
FIG. 15B is a front perspective of the housing showing various internal components disposed therein.
Figure 16A:
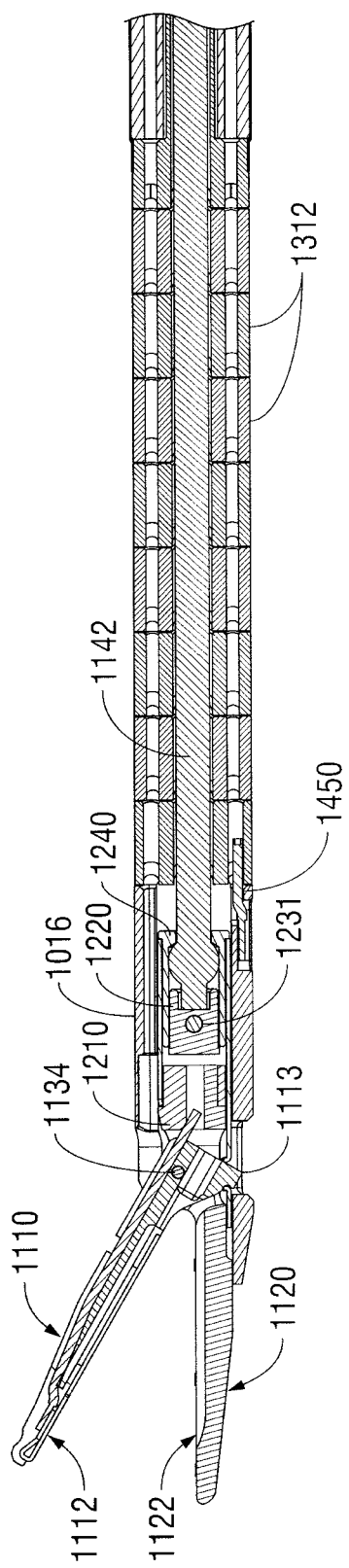
FIG. 16A is a side cross section of the partially flexible shaft of FIG. 13 with end effector assembly shown in open configuration.
Figure 16B:
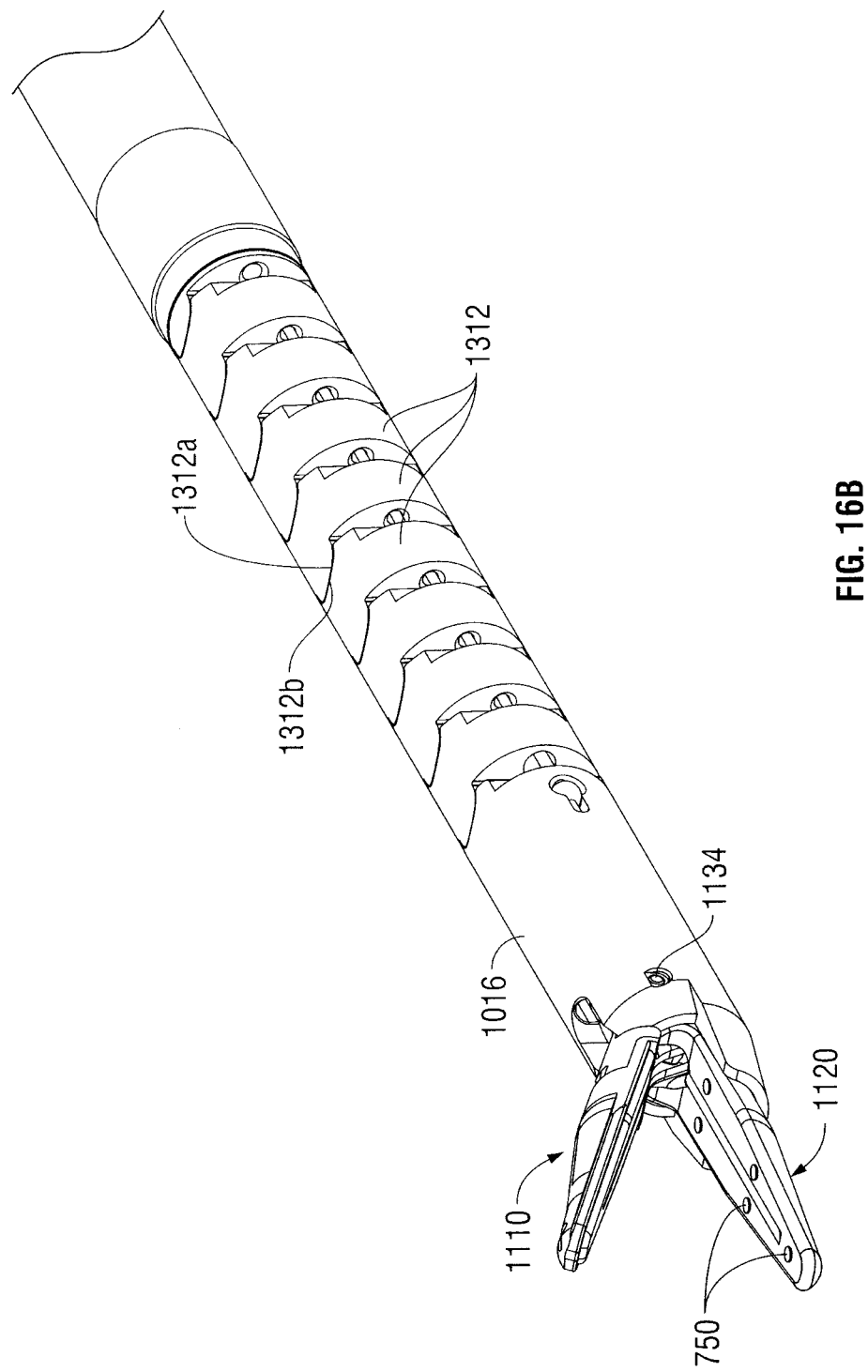
FIG. 16B is a front perspective of the partially flexible shaft of FIG. 13 with end effector assembly shown in open configuration.
Figure 17A:
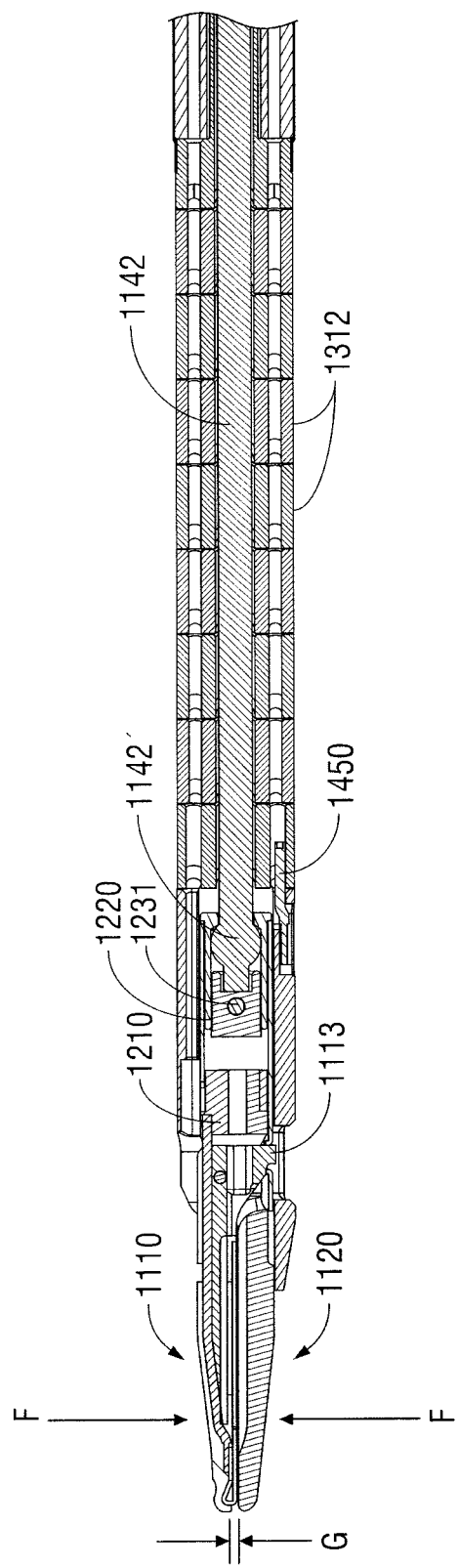
FIG. 17A is a side cross section of the partially flexible shaft of FIG. 13 with end effector assembly shown in closed configuration.
Figure 17B:
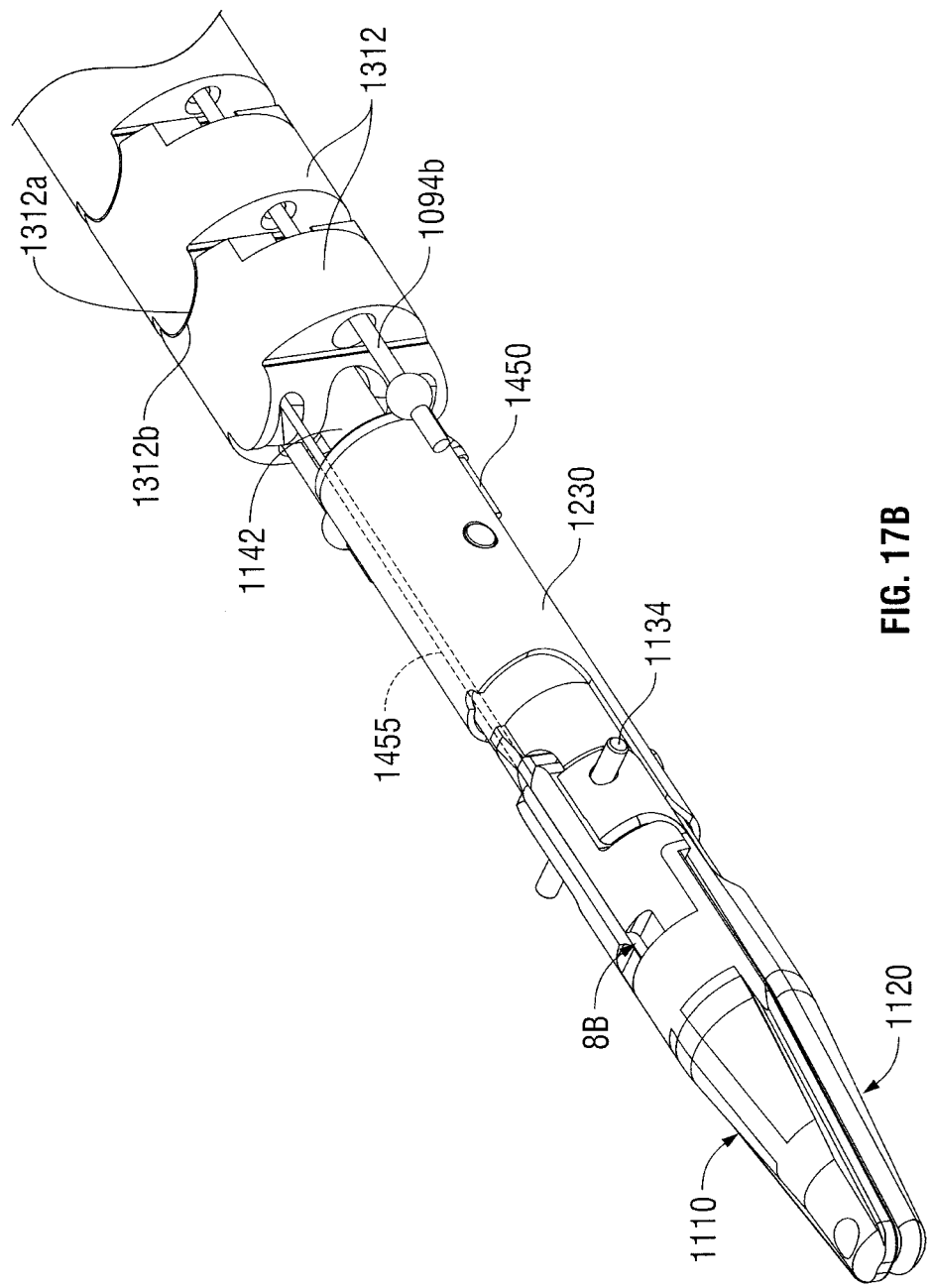
FIG. 17B is a front, internal perspective of the partially flexible shaft of FIG. 13 with end effector assembly shown in closed configuration.

As best seen ion FIG. 14B, the drive assembly 1700 also includes a fine adjustment assembly 1061 operably associated with drive rod 1142 which allows a manufacturer to finely adjust the opening of the jaw members 1110 and 1120 relative to one another prior to final assembly. More particularly, the drive rod 1142 is connected to an adapter 1063 which, in turn, connects to drive rod 1142*a* connected to drive assembly 1700 as describe below. Adapter 1063 is threaded at a distal end thereof to threadably engage an adjustment knob 1067 to allow a manufacturer to finely adjust the length of the drive rode 1142 relative to the drive assembly 1700 thereby allowing the relative separation distance of the jaw members 1110 and 1120 to be accurately and finely controlled.

As best shown in FIGS. 14C, 15A, 15B, 19A and 19B, actuation of the drive assembly 1700 allows a user to selectively open and close the jaw members 1110 and 1120 to grasp and seal tissue. More particularly, the drive assembly 1700 includes a frame block 1800 which operably mounts a compression spring 1740 that biases the drive rod 1142 and coupling drive rod 1142*a* thereagainst. The coupling drive rod 1142*a* mounts to a drive block 1710 which, in turn, is coupled to the distal end of frame block 1800 by adapter 1720. When assembled, the frame block 1800 is disposed between opposing rails 1021 defined in housing halves 1020*a* and 1020*b* (See FIG. 14C) which permit the frame block 1800 to move within the housing 1020 upon actuation of handle 1040. Spring 1740 is mounted between a spacer 1730 (disposed adjacent adapter block 1720) and the proximal end 1810 of frame block 1800. A drive pin 1750 mounts to the opposite end of drive block 1710 and supports the compression spring 1740 to enable movement of the drive rod 1142.

Figure 19A:
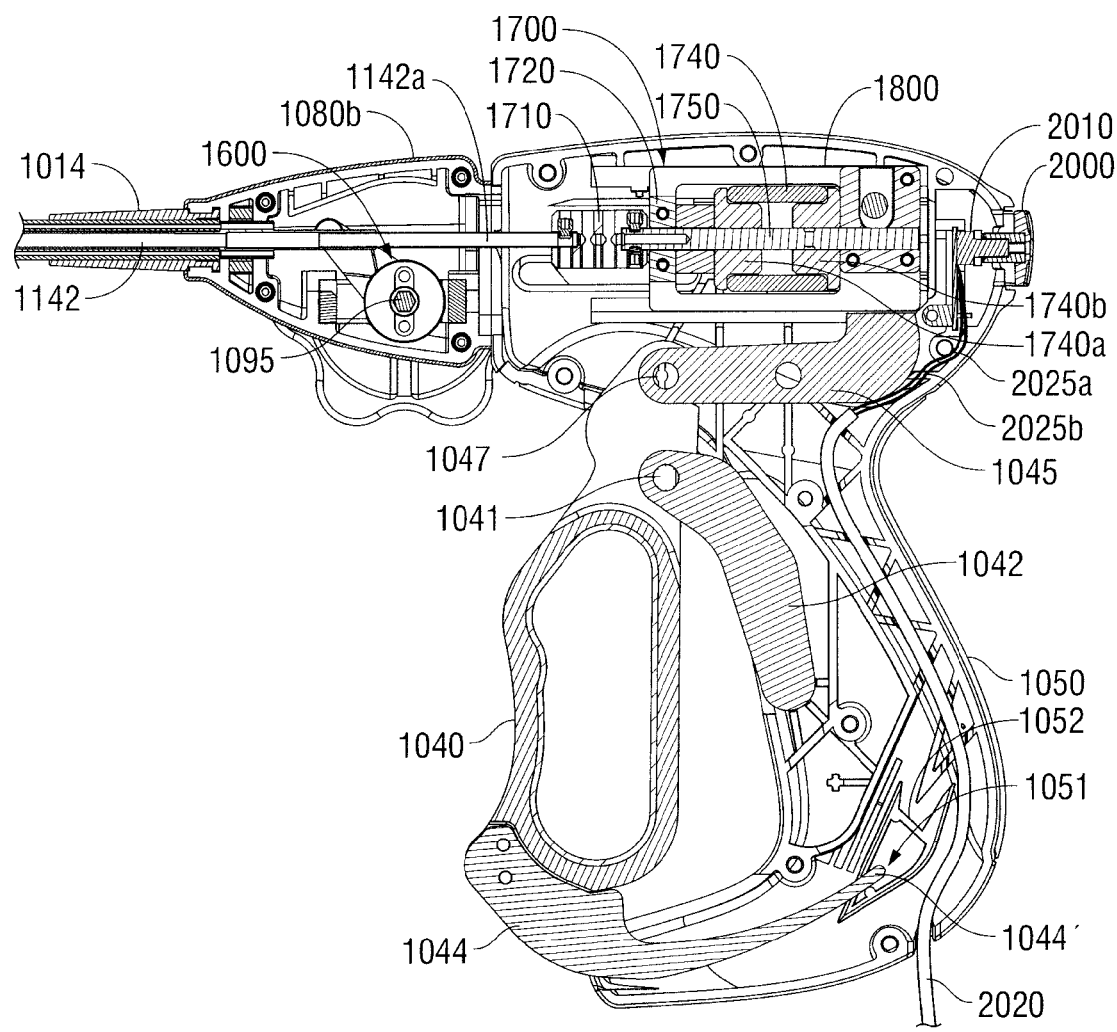
FIG. 19A is a side cross section of the housing showing the forceps in a substantially closed orientation.
Figure 19B:
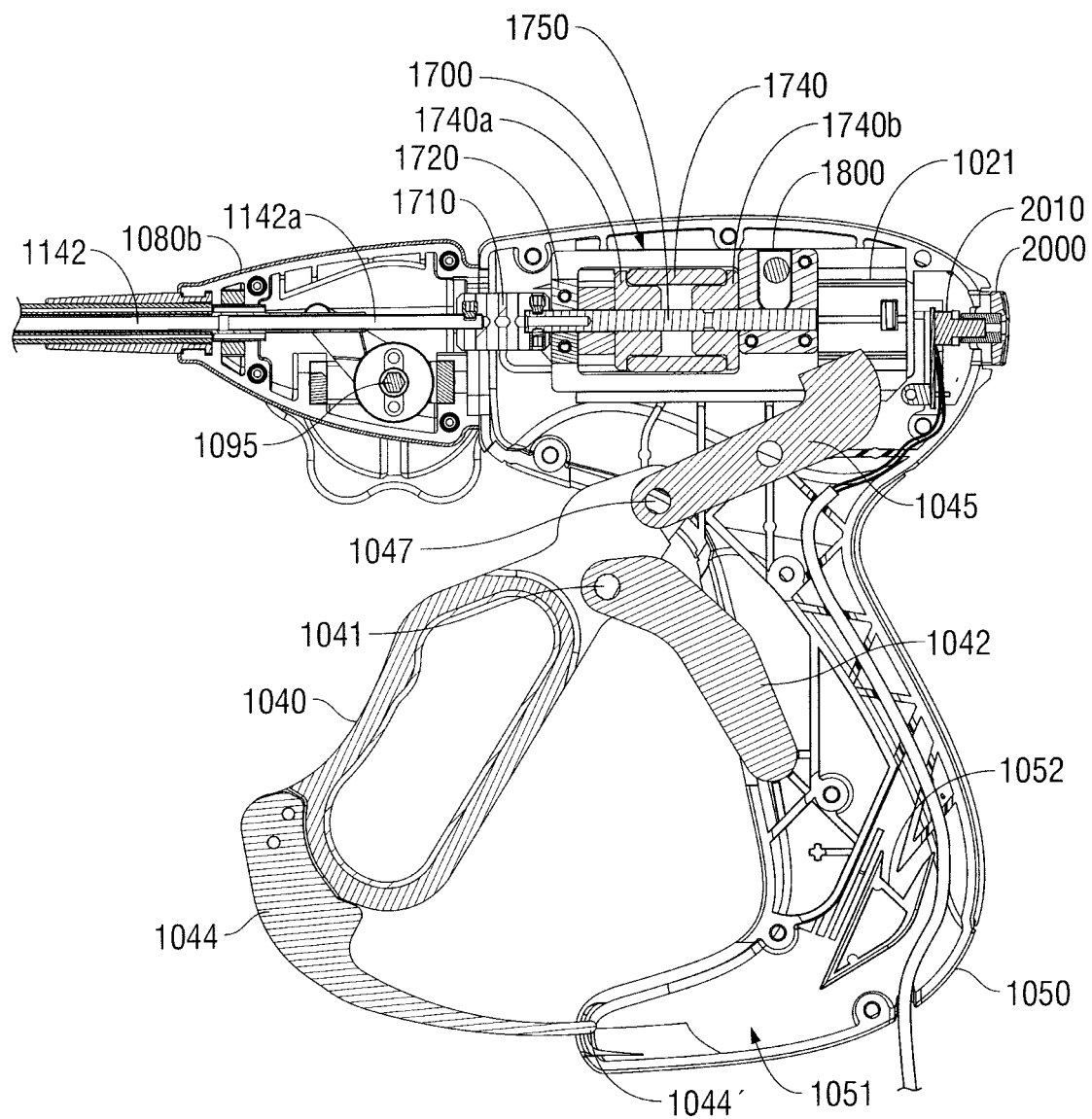
FIG. 19B is a side cross section of the housing showing the forceps in a substantially open orientation.
Figure 20A:
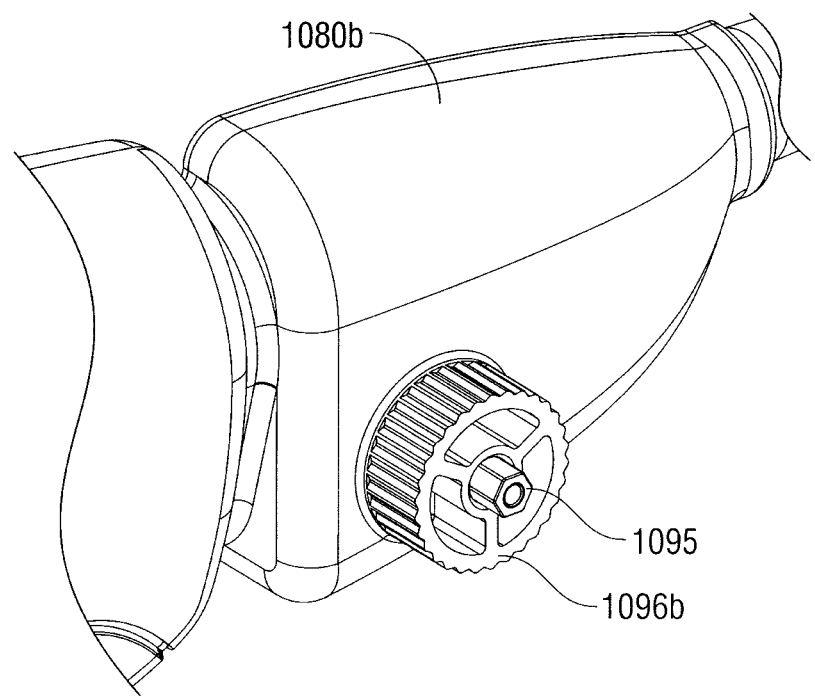
FIGS. 20A-20B are enlarged side perspective views of a gear member and articulation wheel of the articulation assembly.
Figure 20B:
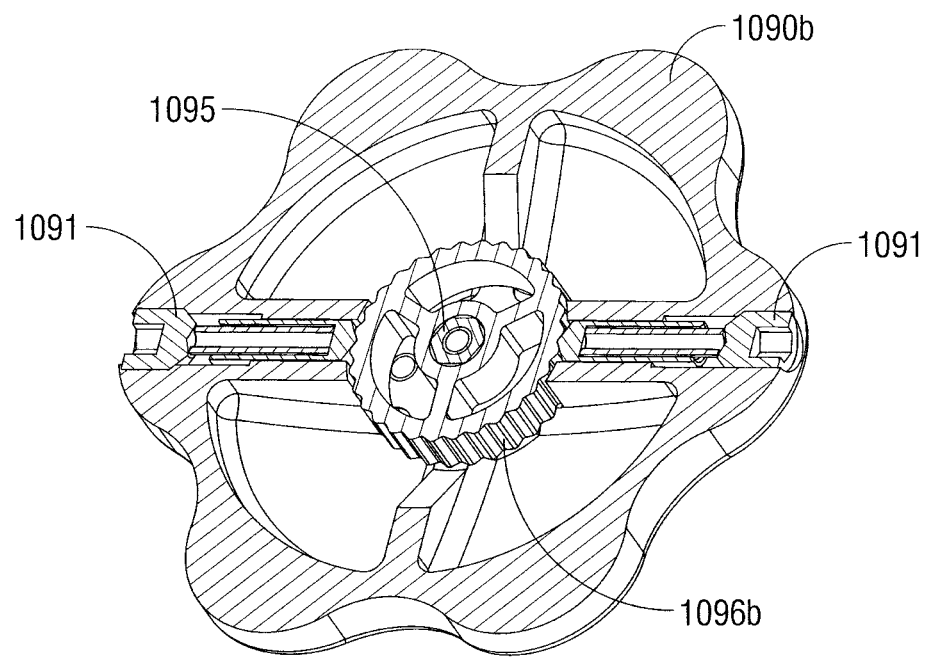

As mentioned above, handle 1040 is operable mounted to the drive assembly 1700 such that movement of the handle 1040 relative to handle 1050 translates the drive rod 1142 to open and close the jaw members 1110 and 1120. More particularly, handle 1040 is mounted at a top or distal end thereof via pin 1047 to link 1045 which, in turn, mounts to frame block 1800 also via pin 1047. Handle 1040 is also mounted to link 1042 at pivot point 1041 which, in turn, mounts to handle 1050 at pivot 1057 to complete the four bar mechanical assembly. As best shown in the comparison of FIGS. 19A and 19B, movement of handle 1040 towards handle 1050 rotates the two links 1042 and 1045 to force the frame block 1800 proximally and pull the drive rod 1142*a* proximally (which pulls drive rod 1142 proximally) to close the jaw members 1110 and 1120. At the same time, flange 1044 operably coupled to the bottom of handle 1040, reciprocates into a guide channel 1051 defined in handle 1050 such that a t-shaped end 1044' locks the handle 1040 in place relative to handle 1050. Flange 1044 and channel 1051 operate in a similar manner as described above with respect to forceps 10.

Spring 1740 includes two opposing compression discs 1740*a* and 1740*b* disposed therein which slidingly mount atop drive pin 1750. Upon movement to of handle 1040 towards handle 1050, spring disc 1740*a* is forced by movement of adapter 1720 to compress atop drive pin 1750 and pull the drive rod 1142 proximally. As mentioned above, movement of the drive rod 1142 proximally, causes the drive sleeve 1230 to engage flange 1113 of jaw member 1110 and close jaw members 1110 relative to jaw member 1120. Flange 1044 thereafter locks the handle 1040 relative to handle 1050 by virtue of the t-shaped end 1044' engaging a catch basin 1052 defined in the handle 1050. Upon re-grasping of handle 1040, the t-shaped end 1044' on flange 1044 is redirected out of channel 1051 to free handle 1040 for movement away from handle 1050. Spring 1740 biases the handle 1040 in an open orientation.

As mentioned above, jaw member 1120 may include a series of stop members 750 disposed on the inner facing surfaces of the electrically conductive sealing surface 1122 to facilitate gripping and manipulation of tissue and to define a gap "G" (see FIG. 17A) between opposing jaw members 1110 and 1120 during sealing and cutting of tissue. The preferred gap "G" between the conductive sealing surfaces 1112 and 1122 to effectively and reliably seal tissue is between about 0.001 and about 0.006 inches. The stop members 750 may be disposed in any configuration along the electrically conductive jaw surfaces 1112 and 1122 depending upon a particular jaw configuration or desired surgical result.

The end effector assembly 1100 may also be articulated in either direction (See arrow "B-B") as shown with reference to FIG. 18A. Once the tissue is grasped (within the required pressure range of about 3 kg/cm$^2$ to about 16 kg/cm$^2$), the user then selectively applies electrosurgical energy to effectively seal tissue. Once sealed, the user may then selectively advances a knife (not shown) by actuating a trigger assembly (not shown) to cut the tissue along the tissue seal. The operating features and relative movements of one envisioned knife and trigger assembly are described above and also described with reference to U.S. patent application Ser. No. 10/460,926, the entire contents being incorporated herein.

Similar to FIGS. 2 and 3 above, the forceps 1000 includes a plurality of joints 1312 which are nestingly arranged in series to form flexible shaft 1012*b*. The distal end or coupling assembly 1016 mechanically engages the end effector assembly 1100 and the proximal end 1014 of the shaft 1012 mechanically engages the housing 1020. Each of the plurality of joints 1312 of the flexible shaft 1012b includes a distal knuckle 1312a and a proximal clevis 1312b formed therewith. Each knuckle 1312a operatively engages a clevis 1312b of an adjacent joint 1312a. Each joint 1312 has a central lumen 1317 defined therein and a pair of opposed lumens 1315a and 1315b formed on either side of central lumen 1317. The articulation cables 1094a and 1094b slideably extend through respective lumens 1315a and 1315b of joints 1312. The operation of cables 1094a and 1094b is explained above. The articulation cables 1094a and 1094b are preferably made from a flexible, friction-reducing material.

A switch 2000 is included which may conform to the outer shape of housing 1020 (once assembled). It is envisioned that the switch 2000 permits the user to selectively activate the forceps 1000 in a variety of different orientations, i.e., multi-oriented activation. As can be appreciated, this simplifies activation. A push button 2010 extends distally and engages a toggle plate 2015 (See FIG. 15B) which, in turn, connects to an electrical interface or PC Board (not shown). Electrical leads 2025a and 2025b internally disposed in cable 2020 (See FIG. 19) electrically connect to electrical interface or PC board. When the push button 2010 is depressed, the leads 2025a and 2025b carry electrical potentials to the jaw members 1110 and 1120.

It is envisioned that a safety switch or circuit (not shown) may be employed such that the switch cannot fire unless the jaw members 1110 and 1120 are closed and/or unless the jaw members 1110 and 1120 have tissue held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. U.S. patent application Ser. No. 10/427,832 describes one such feedback system, the entire contents of which are incorporated by reference hereinabove.

Various handles and/or handle assemblies may be operatively connected or otherwise associated with end effector assembly 1100 in order to effect operation and movement of the various components thereof, i.e., drive rod 1142 and/or articulation cables 1094a, 1094b. Exemplary handles and/or handle assemblies for use with end effector 1100 are disclosed in U.S. Provisional Application Ser. No. 60/849,562 filed on Oct. 5, 2006, entitled "PROGRAMMABLE HANDLE ASSEMBLY FOR SURGICAL DEVICES"; and U.S. Provisional Application Ser. No. 60/849,560 filed on Oct. 5, 2006, entitled "HANDLE ASSEMBLY FOR ARTICULATED ENDOSCOPIC INSTRUMENTS", the entire disclosures of each of which being incorporated hereinabove by reference.

From the foregoing and with reference to the various figure drawings, those skilled in the art will appreciate that certain modifications can also be made to the present disclosure without departing from the scope of the same. For example, it is contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120. Examples of such sensor systems are described in commonly-owned U.S. patent application Ser. No. 10/427,832 entitled "METHOD AND SYSTEM FOR CONTROLLING OUTPUT OF RF MEDICAL GENERATOR" filed on May 1, 2003 the entire contents of which are incorporated by reference hereinabove.

As can be appreciated, locating the switch 400, 2000 on the forceps 10, 1000 has many advantages. For example, the switch 400, 2000 reduces the amount of electrical cable in the operating room and eliminates the possibility of activating the wrong instrument during a surgical procedure due to "line-of-sight" activation. Moreover, it is envisioned that the switch 400, 2000 may be decommissioned during activation of the knife 185. Decommissioning the switch 400, 2000 when the trigger is actuated eliminates unintentionally activating the forceps 10, 1000 during the cutting process. It is also envisioned that the switch 400, 2000 may be disposed on another part of the forceps 10, 1000, e.g., the handle 40, 1040, rotating assembly 80, housing 20, etc.

Another envisioned safety mechanism would be to route one of the cable leads to energize the one jaw member, e.g., jaw member 1120, and the other electrical potential may be conducted through a drive sleeve, e.g., drive sleeve 1230, surrounding drive rod 1142 and transferred to the other jaw member 1110 to establish electrical continuity only upon retraction of the drive sleeve. It is envisioned that this particular envisioned embodiment will provide at least one additional safety feature, i.e., electrical continuity to the jaw members 1110 and 1120 is made only when the jaw members 1110 and 1120 are closed. The drive rod 1142 may also be energized to the second electrical potential and include a similar-type safety mechanism.

In one envisioned embodiment, the knife 185 may not be included with the forceps 10, 1000 and the instrument is designed solely for sealing vessels or other tissue bundles. In this instance, the camming hub 144 (with respect to forceps 10 only) may be rotated to articulate the end effector assembly 100 and cables 94a and 94b may be eliminated.

In one embodiment, two isolated electrical leads may supply electrical energy to respective jaw members 110 and 120 (or 1110 and 1120). In this instance it may be desirable to provide a channel along the outside of shaft 12, 1012 which guides the electrical leads from the housing 20, 1020 to the individual jaw members 110, 120 (or 1110 and 1120) One or more wire crimps or the like may be utilized to hold the electrical leads in place. Alternatively, cables 94a and 94b (or 1094a and 1094b) may be utilized to both articulate the end effector assembly 100 (or 1100) and to supply electrical energy to the jaw members 110 and 120 (or 1110 and 1120).

With particular respect to forceps 10 in particular but nor exclusively, the cable lead, e.g., cable lead 311 of forceps 10 is held loosely but securely along the cable path to permit rotation of the jaw member 110 about pivot 103. The two potentials are isolated from one another by virtue of the insulative sheathing surrounding cable lead 311. Moreover, the proximal portion of shaft 12 may be rigid or substantially rigid and the distal portion is flexible and/or articulateable in the manner described in more detail above. Alternatively, the entire shaft 12 may be flexible. Still further, the trigger assembly 70 may be prevented from firing until movable handle 40 is locked (or simply moved) proximally to close the jaw members 110 and 120.

In embodiment relating to both forceps 10, 1000, the electrically conductive sealing surfaces 112,122 and 1112, 1122 of the jaw members 110, 120 and 1110, 1120, respectively, are relatively flat to avoid current concentrations at sharp edges and to avoid arcing between high points. In addition and due to the reaction force of the tissue when engaged, jaw members 110, 120 and 1110, 1120 can be manufactured to resist bending. For example, the jaw members 110, 120 and 1110, 1120 may be tapered along the width thereof which resists bending due to the reaction force of the tissue.

It is envisioned that the outer surface of the end effector assembly 100, 1100 may include a nickel-based material, coating, stamping, metal injection molding which is designed to reduce adhesion between the jaw members 110, 120 and 1110, 1120 with the surrounding tissue during activation and sealing. Moreover, it is also contemplated that the conductive surfaces 112, 122 and 1112 and 1122 of the jaw members 110, 120 and 1110, 1120, respectively, may be manufactured from one (or a combination of one or more) of the following materials: nickel-chrome, chromium nitride, MedCoat 2000 manufactured by The Electrolizing Corporation of OHIO, Inconel 600 and tin-nickel. The tissue conductive surfaces 112, 122 and 1112 and 1122 may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 112, 122 and 1112 and 1122 made from or coated with Ni200, Ni201 (~100% Ni) also showed improved non-stick performance over typical bipolar stainless steel electrodes.

Forceps 10, 1000 may be designed such that it is fully or partially disposable depending upon a particular purpose or to achieve a particular result. For example, end effector assembly 100, 1100 may be selectively and releasably engageable with the distal end of the shaft 12, 1012 and/or the proximal end 14, 1014 of shafts 12, 1012 may be selectively and releasably engageable with the housing 20, 1020. In either of these two instances, the forceps 10, 1000 would be considered "partially disposable" or "reposable", i.e., a new or different end effector assembly 100, 1100 (or end effector assembly 100, 1100 and shaft 12, 1012) selectively replaces the old end effector assembly 100, 1100 as needed. As can be appreciated, the presently disclosed electrical connections would have to be altered to modify the instrument to a reposable forceps.

Figure 21:
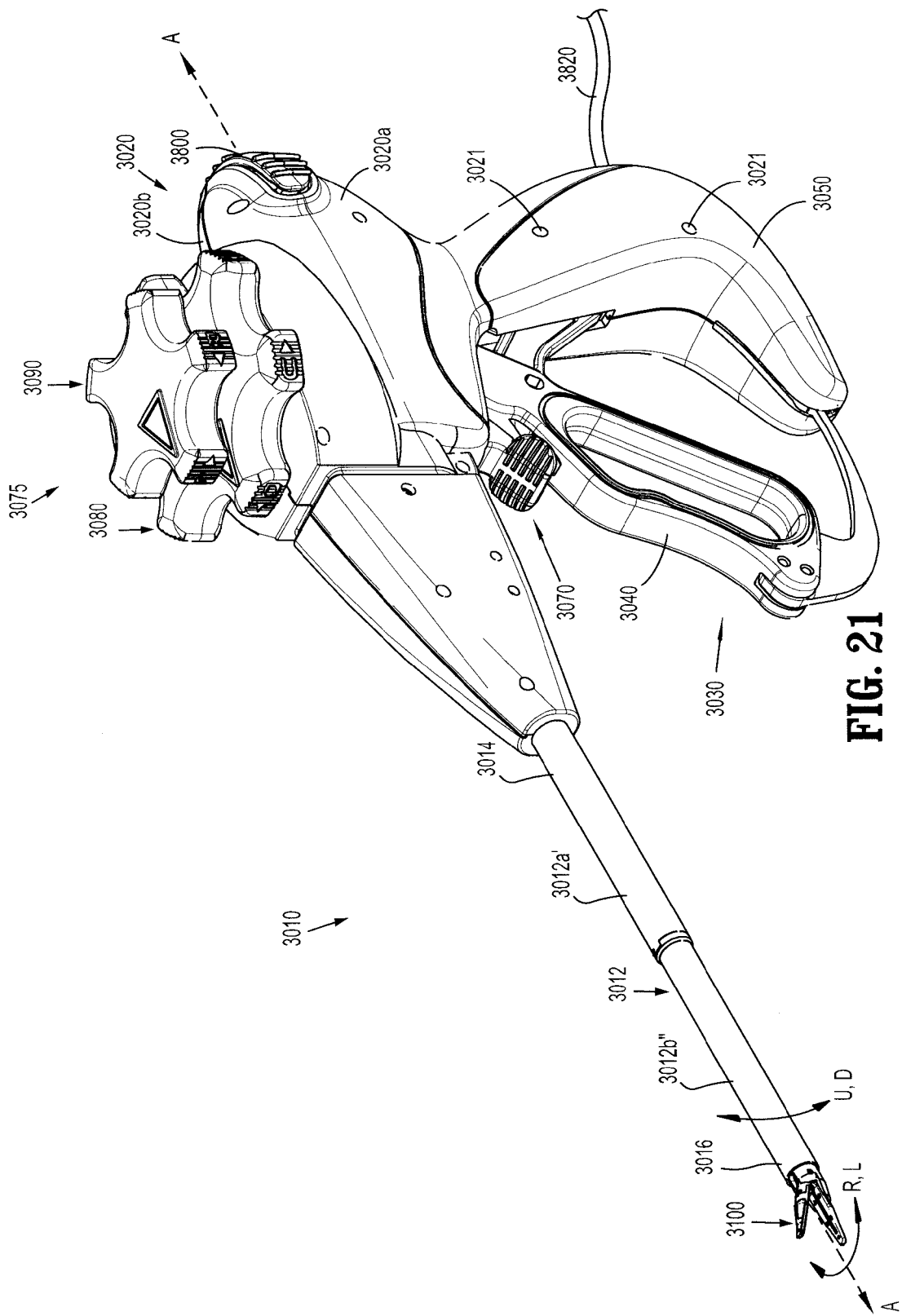
FIG. 21 is a perspective view of an endoscopic forceps showing a housing, a flexible shaft, articulating assembly and an end effector assembly according to another embodiment of the present disclosure.
Figure 22:
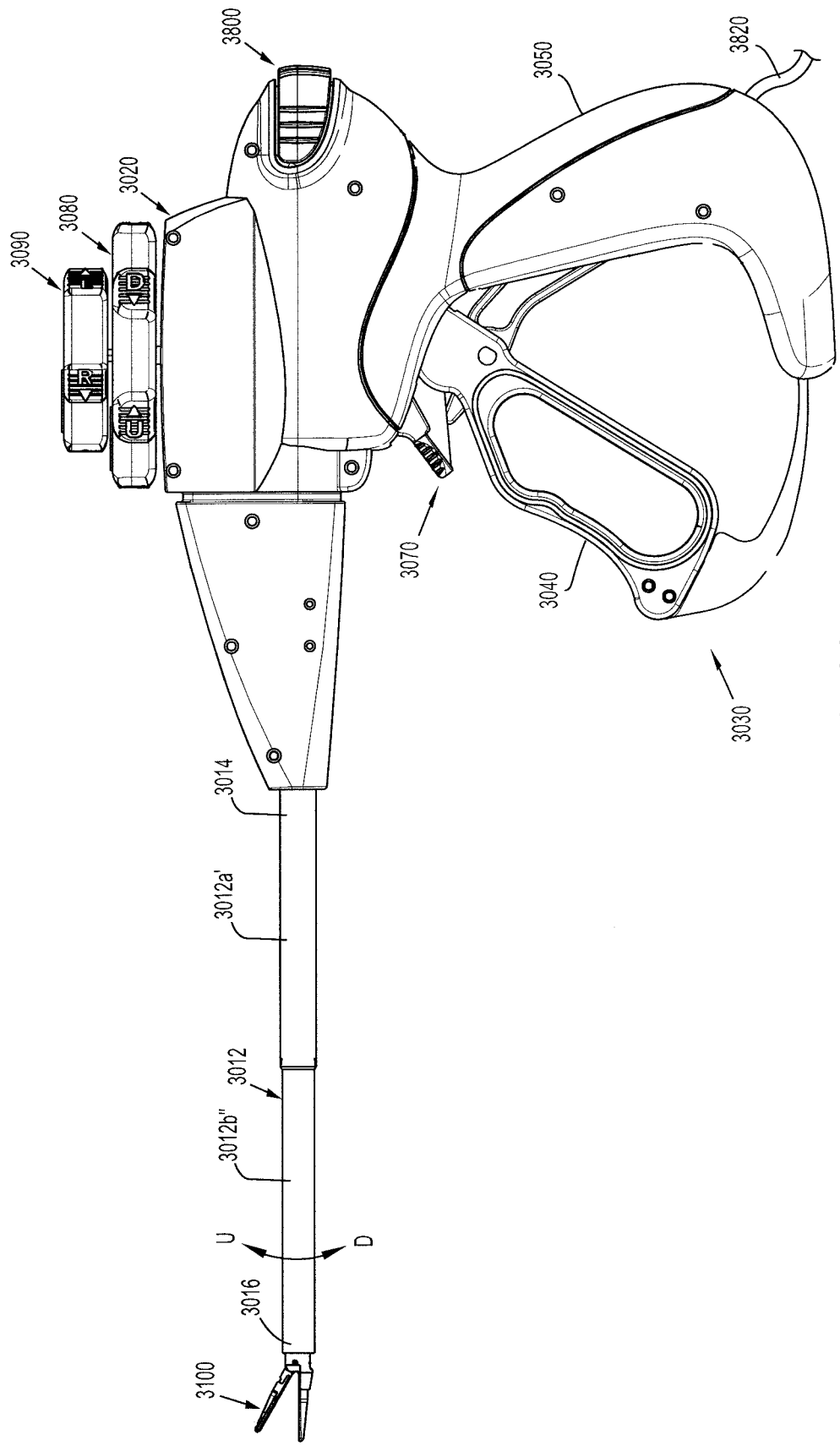
FIG. 22 is side view of the forceps of FIG. 21.

Turning now to FIGS. 21-22, another embodiment of an endoscopic vessel sealing forceps 3010 is shown for use with various surgical procedures and generally includes a housing 3020, a handle assembly 3030, an articulation assembly 3075 composed of two articulators 3080 and 3090, a trigger assembly 3070 and an end effector assembly 3100 all of which mutually cooperate to articulate, grasp, seal and divide tubular vessels and vascular tissue. Although the majority of the figures relating to this embodiment depict a bipolar sealing forceps 3010 for use in connection with endoscopic surgical procedures, the present disclosure may be used for monopolar surgical procedures which employ a remote patient pad for completing the current loop.

Forceps 3010 includes a generally flexible shaft 3012 which has a distal end 3016 dimensioned to mechanically engage the end effector assembly 3100 and a proximal end 3014 which mechanically engages a distal portion of the housing 3020. In one embodiment, the shaft 3012 has at least two portions, a proximal portion 3012a' and a distal portion 3012b' (See FIG. 23). The proximal portion 3012a' of the shaft 3012 may be formed of a flexible tubing (e.g., plastic) and may incorporate a tube of braided steel to provide axial (e.g., compressional) and rotational strength. The distal portion 3012b' of shaft 3012 may be also be flexible, but may incorporate one or more moving joints 3012a, 3012b. A casing or insulating material 3012b'' may be employed to protect a plurality of internal moving joints 3012a (See FIGS. 21 and 48) of the flexible shaft 3012.

In one embodiment, the proximal portion 3012a' of the shaft 3012 is flexible and non-articulating while the distal portion 3012b' of shaft 3012 is capable of articulating in response to movement of articulation cables or wires. Details of how the shaft 3012 flexes are described in more detail below with respect to FIGS. 38 and 40-45. The proximal end 3014 of shaft 3012 is received within a distal end of the housing 3020 and connected to the articulating assembly 3090 and drive assembly 3024 as explained in further detail below. In the drawings and in the descriptions which follow, the term "proximal," as is traditional, will refer to the end of the forceps 3010 which is closer to the user, while the term "distal" will refer to the end which is farther from the user.

As best seen in FIG. 21, forceps 3010 also includes an electrosurgical cable 3820 which connects the forceps 3010 to a source of electrosurgical energy, e.g., a generator (not shown). It is contemplated that generators such as those sold by Covidien-Energy-based Devices, located in Boulder, Colo. may be used as a source of electrosurgical energy, e.g., Covidien's LIGASURE™ Vessel Sealing Generator and Covidien's Force Triad™ Generator.

The generator may include various safety and performance features including isolated output, independent activation of accessories and/or so-called "Instant Response™" software which is a proprietary technology owned by Covidien. Instant Response™ is an advanced feedback system which senses changes in tissue 200 times per second and adjusts voltage and current to maintain appropriate power. The Instant Response™ technology is believed to provide one or more of the following benefits to vessel sealing: consistent clinical effect through all tissue types; reduced thermal spread and risk of collateral tissue damage; less need to "turn up the generator"; and designed for the minimally invasive environment.

Figure 29:
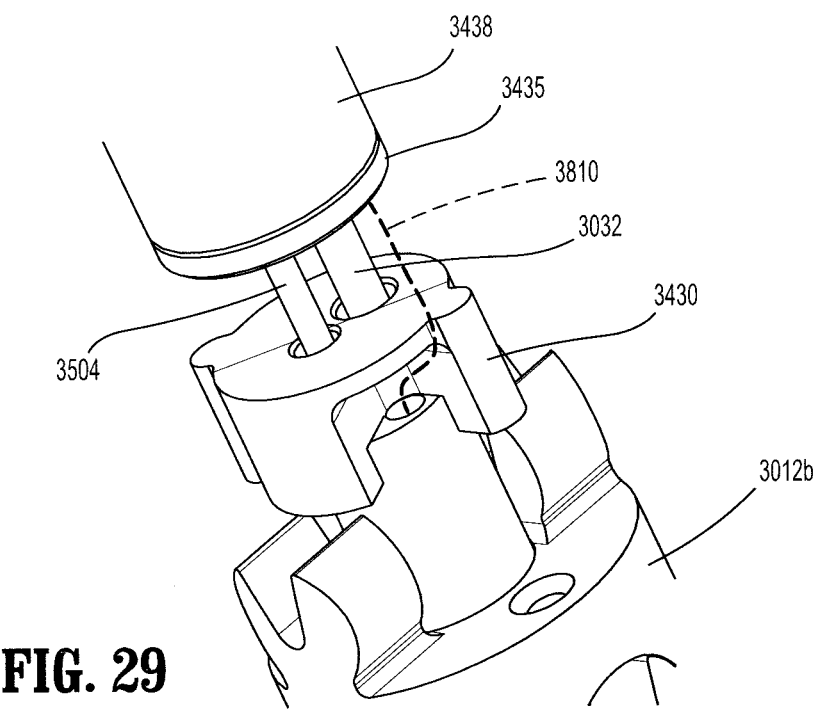
FIG. 29 is a greatly-enlarged, internal view of a guide plate configured to translationally support a drive rod and a knife rod for reciprocation therethrough.
Figure 30:
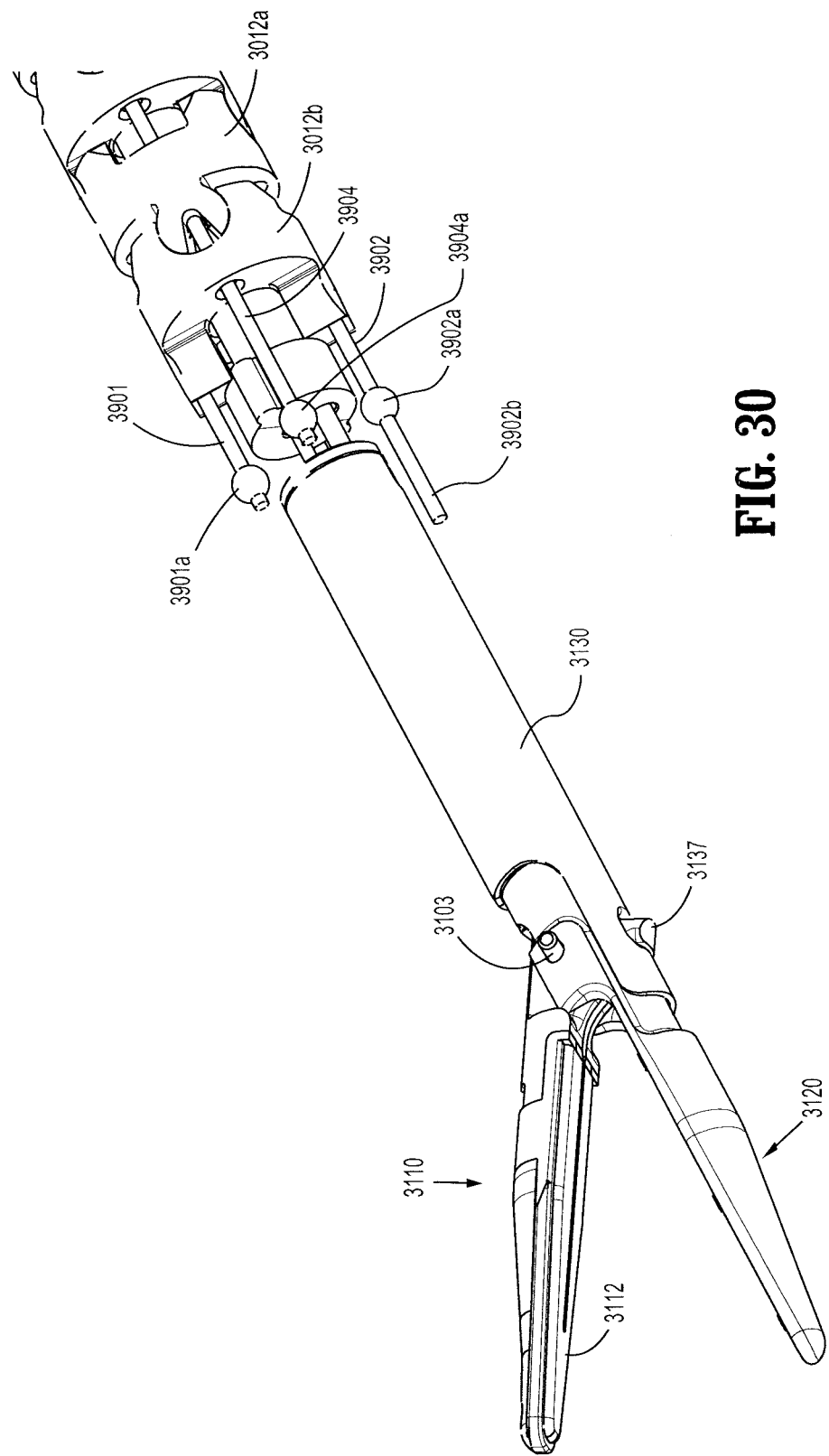
FIG. 30 is an enlarged perspective view of the forceps shown in open configuration and showing a drive sleeve for actuating the jaw members and the plurality of steering cables.
Figure 33:
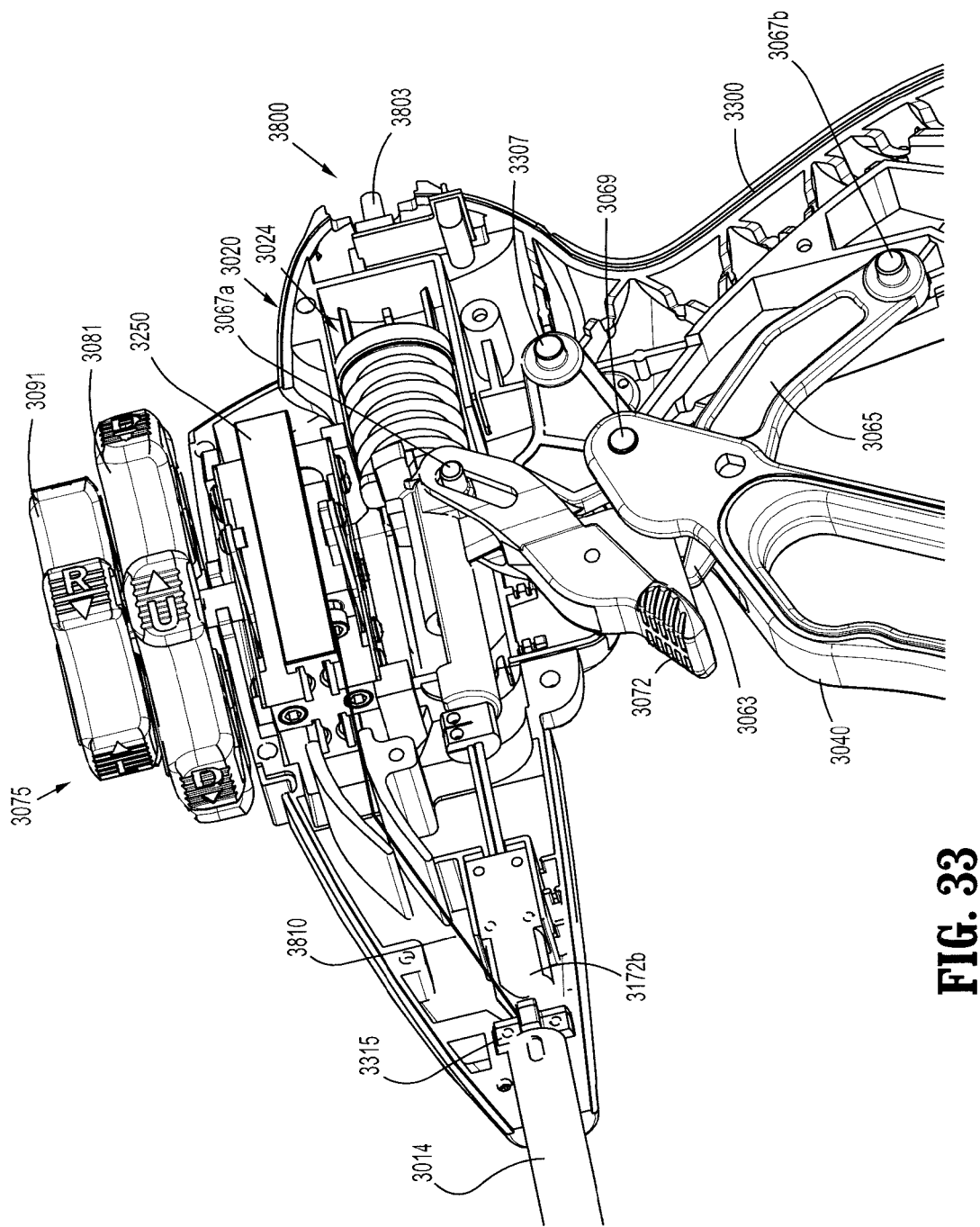
FIG. 33 is a front perspective internal view showing the internal components of the drive assembly and articulating assembly.

Cable 3820 is internally divided into numerous leads, e.g., lead 3810, control leads (not shown) and a ground lead (not shown) which each transmit electrosurgical energy through their respective feed paths 3809 (See FIG. 34) through the forceps 3010 and a guide path 3850 defined in an end effector support 3400 (See FIG. 29) for ultimate connection to the end effector assembly 3100 as explained in more detail below with respect to the description of FIG. 25.

Handle assembly 3030 includes a fixed handle 3050 and a movable handle 3040. Fixed handle 3050 is integrally associated with housing 3020 and handle 3040 is movable relative to fixed handle 3050 as explained in more detail below with respect to the operation of the forceps 3010. Articulation assembly 3075 sits atop housing 3020 and is operable via articulation wheels 3080 and 3090 to move the end effector assembly 3100 (and the flexible distal portion 3012b' of the shaft 3012) in the direction of arrows "U, D" and "R", "L" relative to axis longitudinal A-A as explained in more detail below. Wheels 3080 and 3090 may be provided in alternative arrangements such as disposed on the side of the housing 3020. Also, wheels 3080 and 3090 may be replaced by other mechanisms to articulate the jaw members 3110 ad 3120 such as levers, trackballs, joysticks, or the like. Details relating to the articulation assembly 3075 are explained in more detail below with reference to FIGS. 24A-24C, 35, 36, 38 and 40-45.

As mentioned above, end effector assembly 3100 is supported by an end effector support 3400 attached at the distal end 3016 of shaft 3012 and the end effector assembly 3100 includes a pair of opposing jaw members 3110 and 3120. Movable handle 3040 of handle assembly 3030 is ultimately connected to a drive assembly 3024 which, together, mechanically cooperate to impart movement of the jaw members 3110 and 3120 from an open position wherein the jaw members 3110 and 3120 are disposed in spaced relation relative to one another (See FIGS. 44, 47-52), to a clamping or closed position wherein the jaw members 3110 and 3120 cooperate to grasp tissue therebetween.

Figure 23:
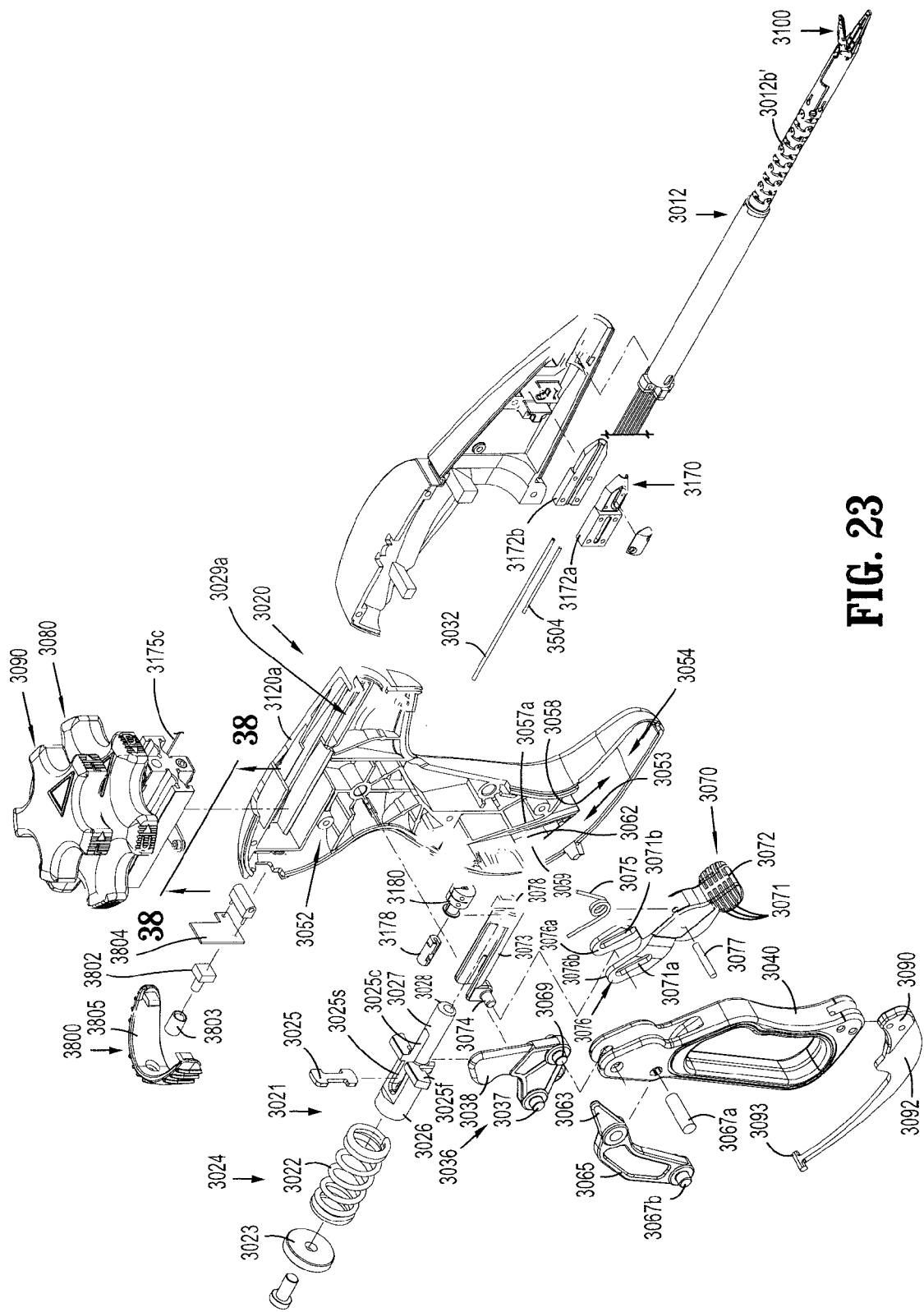
FIG. 23 is an exploded, perspective view of the forceps of FIG. 21.

As shown best in FIG. 23, housing 3020 encloses a drive assembly 3024 which cooperates with the movable handle 3040 to impart movement of the jaw members 3110 and 3120 from the open position to the clamping or closed position. The handle assembly 3030 can generally be characterized as a four-bar mechanical linkage composed of the following elements: movable handle 3040, a link 3065, a cam-like link 3036 and a base link embodied by fixed handle 3050 and a pair of pivot points 3037 and 3067b. Movement of the handle 3040 activates the four-bar linkage which, in turn, actuates the drive assembly 3024 for imparting movement of the opposing jaw members 3110 and 3120 relative to one another to grasp tissue therebetween.

It is envisioned that employing a four-bar mechanical linkage will enable the user to gain a significant mechanical advantage when compressing the jaw members 3110 and 3120 against the tissue as explained in further detail below with respect the operating parameters of the drive assembly 3024. Although shown as a four-bar mechanical linkage, the present disclosure contemplates other linkages to effect relative motion of the jaw members 3110 and 3120 as is known in the art.

Fixed handle 3050 includes a channel 3054 defined therein that is dimensioned to receive a flange 3092 which extends proximally from movable handle 3040 (See FIG. 23). Flange 3092 includes a fixed end 3090 that is affixed to movable handle 3040 and a t-shaped free end 3093 which is dimensioned for facile reception within channel 3054 of handle 3050. It is envisioned that flange 3092 may be dimensioned to allow a user to selectively, progressively and/or incrementally move jaw members 3110 and 3120 relative to one another from the open to closed positions. For example, it is also contemplated that flange 3092 may include a ratchet-like interface which lockingly engages the movable handle 3040 and, therefore, jaw members 3110 and 3120 at selective, incremental positions relative to one another depending upon a particular purpose (not shown). Other mechanisms may also be employed to control and/or limit the movement of handle 3040 relative to handle 3050 (and jaw members 3110 and 3120) such as, e.g., hydraulic, semi-hydraulic, linear actuator(s), gas-assisted mechanisms and/or gearing systems.

As best illustrated in FIGS. 21 and 23, the housing 3020 includes two halves 3020a and 3020b which include a plurality of interfaces disposed at various points around the periphery of housing halves 3020a and 3020b for ultrasonic welding purposes, e.g., energy direction/deflection points. It is also contemplated that housing halves 3020a and 3020b (as well as the other components described below) may be assembled together in any fashion known in the art. For example, alignment pins, snap-like interfaces, tongue and groove interfaces, locking tabs, adhesive ports, etc. may all be utilized either alone or in combination for assembly purposes.

Housing halves 3020a and 3020b, when assembled, form an internal cavity 3052 that predefines the channel 3054 within fixed handle 3050 such that an entrance pathway 3053 and an exit pathway 3058 are formed for reciprocation of the t-shaped flange end 3093 therein. Once assembled, a generally triangular-shaped member 3057a defines a rail or track 3059 for movement of the flange 3092 therealong. During movement of the flange 3092 along the entrance and exit pathways 3053 and 3058, respectively, the t-shaped end 3093 rides along track 3059 adjacent triangular member 3057a according to the particular dimensions of the triangularly-shaped member 3057a, which, as can be appreciated, predetermines part of the overall pivoting motion of handle 3040 relative to fixed handle 3050.

Once actuated, handle 3040 moves in a generally arcuate or curved fashion towards fixed handle 3050 about pivot 3069 which causes link 3065 to rotate proximally about pivots 3067a and 3067b which, in turn, cause cam-like link 3036 to rotate about pivots 3037 and 3069 in a generally proximal direction. Movement of the cam-like link 3036 imparts movement to the drive assembly 3024 as explained in more detail below. Moreover, proximal rotation of the link 3065 about pivots 3067a and 3067b also causes a distal end 3063 of link 3065 to release, i.e., "unlock", the trigger assembly 3070 for selective actuation. This feature is explained in detail with reference to FIGS. 31 and 53-54 and the operation of the knife assembly 3500.

As shown best in FIGS. 25-31, the end effector assembly 3100 includes opposing jaw members 3110 and 3120 which cooperate to effectively grasp tissue for sealing purposes. The end effector assembly 3100 is designed as a unilateral assembly, i.e., jaw member 3120 is fixed relative to the shaft 3012 and jaw member 3110 pivots about a pivot pin 3103 to grasp tissue.

Figure 56:
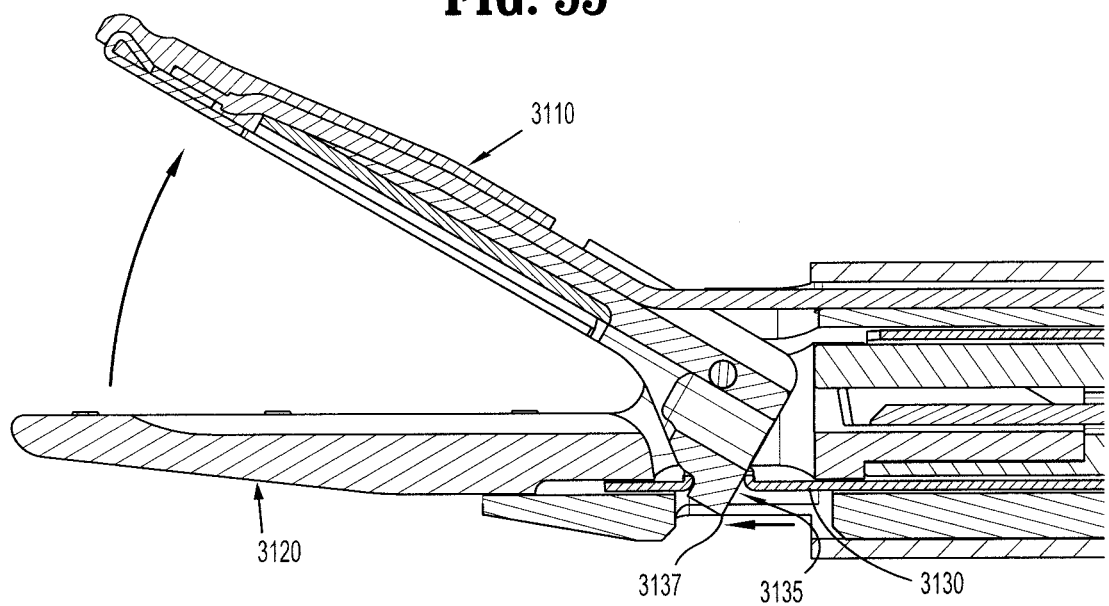
FIG. 56 is a greatly-enlarged, cross section of the end effector assembly showing the relative movement of the drive rod and drive sleeve for opening the jaw members.

More particularly, the unilateral end effector assembly 3100 includes one stationary or fixed jaw member 3120 mounted in fixed relation to the shaft 3012 and pivoting jaw member 3110 mounted about a pivot pin 3103 attached to the stationary jaw member 3120. A reciprocating sleeve 3130 is slidingly disposed within the shaft 3012 and is remotely operable by the drive assembly 3024. The pivoting jaw member 3110 includes a detent or protrusion 3137 which extends from jaw member 3110 through an aperture 3135 disposed within the reciprocating sleeve 3130 (FIG. 25). The pivoting jaw member 3110 is actuated by sliding the sleeve 3130 axially within the shaft 3012 such that a distal end of the aperture 3135 abuts against the detent 3137 on the pivoting jaw member 3110 (See FIGS. 29 and 56). Pulling the sleeve 3130 proximally closes the jaw members 3110 and 3120 about tissue grasped therebetween and pushing the sleeve 3130 distally opens the jaw members 3110 and 3120 for grasping purposes.

Figure 25:
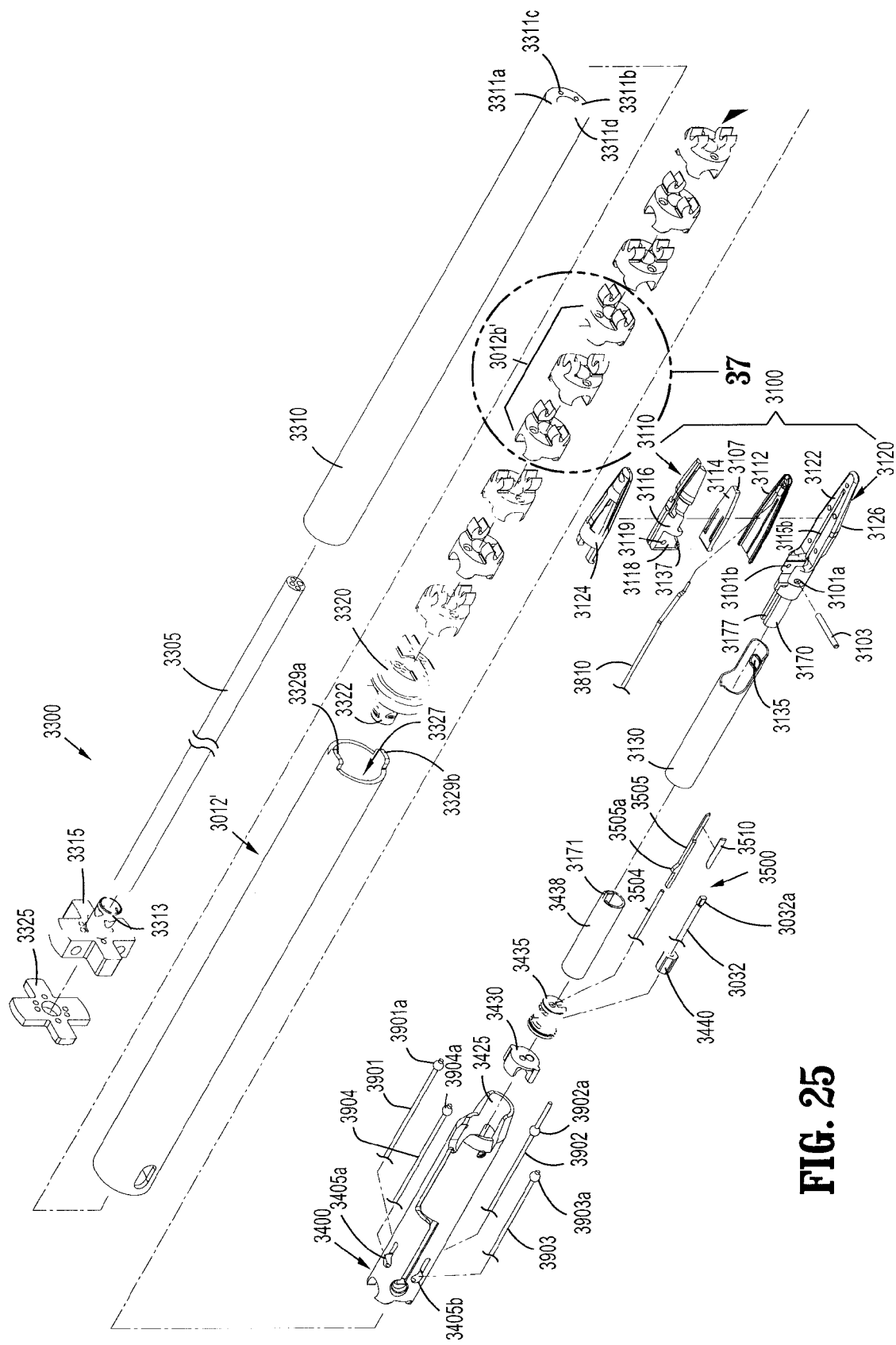
FIG. 25 is an enlarged, exploded perspective view of the flexible shaft and end effector assembly of FIG. 21.
Figure 26:
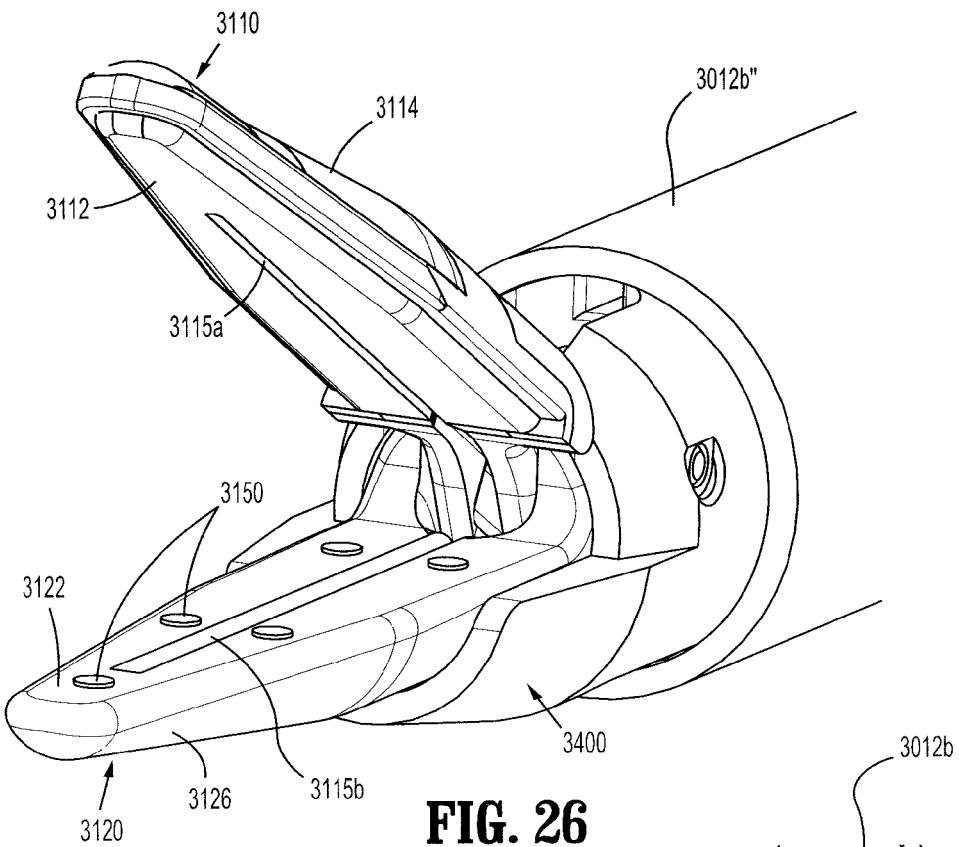
FIG. 26 is a greatly-enlarged, front perspective view of the end effector assembly of FIG. 21.
Figure 27:
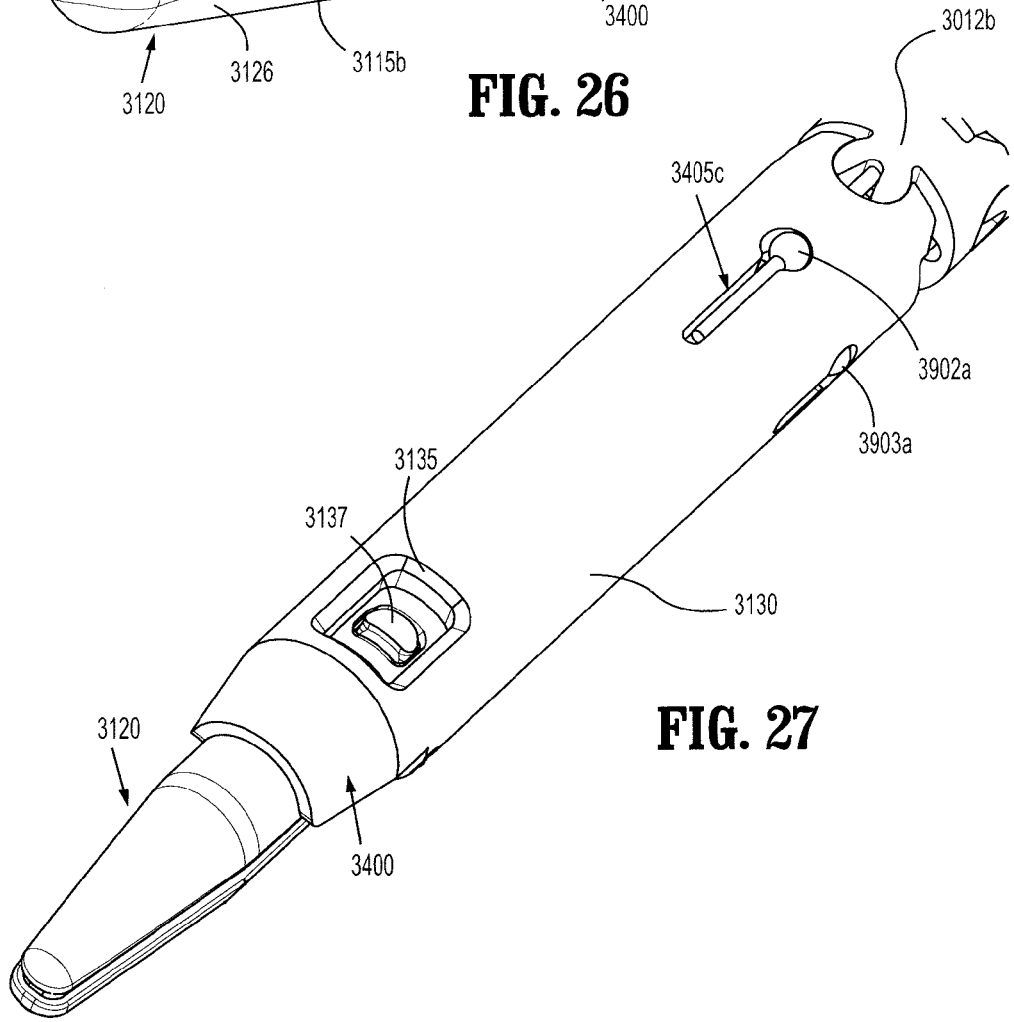
FIG. 27 is an enlarged bottom perspective view of an end effector support configured to support the end effector assembly and secure a plurality of steering cables that are actuated to articulate the forceps.
Figure 28:
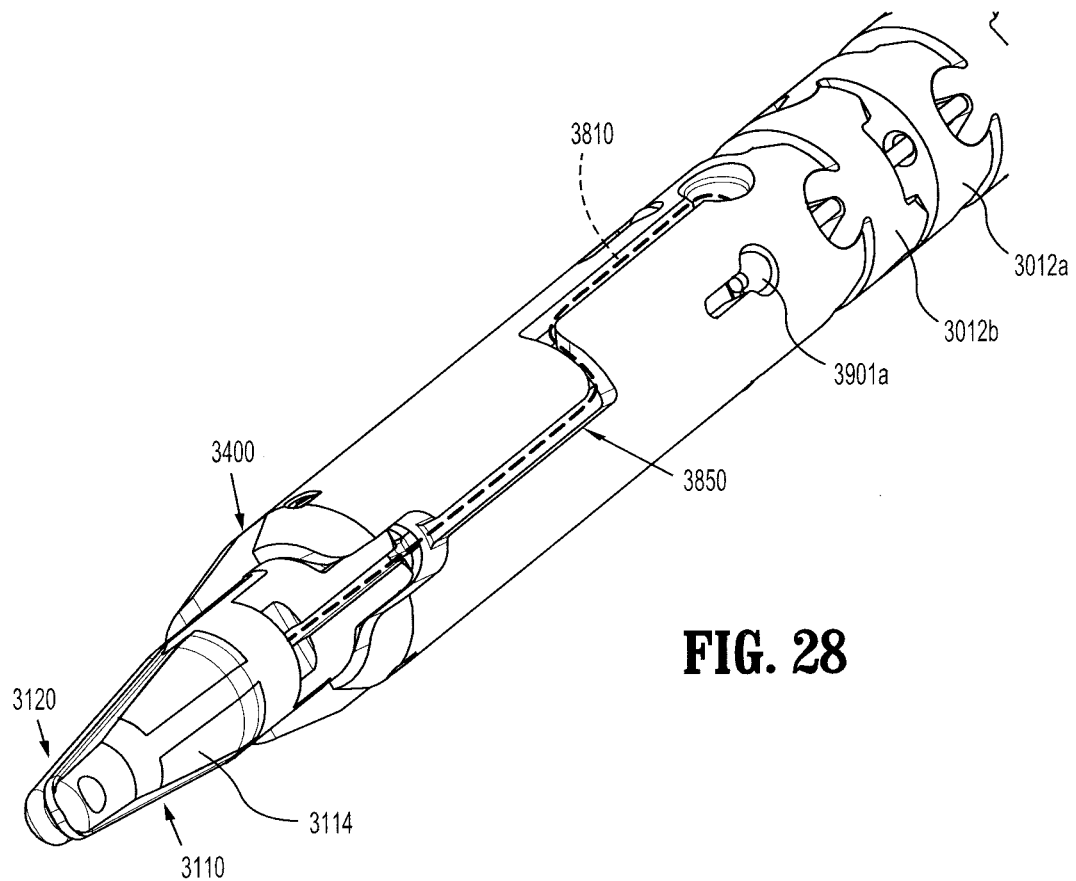
FIG. 28 is an enlarged, top perspective view of the end effector support showing a channel defined therein for guiding an electrical lead.

As best illustrated in FIGS. 25 and 26, knife channels 3115a and 3115b run through the center of the jaw members 3110 and 3120, respectively, such that a blade 3510 from the knife assembly 3500 can cut the tissue grasped between the jaw members 3110 and 3120 when the jaw members 3110 and 3120 are in a closed position. More particularly, the blade 3510 can only be advanced through the tissue when the jaw members 3110 and 3120 are closed thus preventing accidental or premature activation of the blade 3510 through the tissue. Put simply, the knife channels 3115a and 3115b are blocked when the jaws members 3110 and 3120 are opened and aligned for distal activation when the jaw members 3110 and 3120 are closed (See FIGS. 49 and 56). Electrical energy flows through steering cable 3902 (soldered to sleeve 3130) then through sleeve 3130 to jaw 3120 (sleeve 3130 is welded or soldered to jaw 3120).

As best shown in FIG. 25, jaw member 3110 also includes a jaw housing 3116 which has an insulative substrate or insulator 3114 and an electrically conducive surface 3112. Housing 3116 and insulator 3114 are dimensioned to securely engage the electrically conductive sealing surface 3112. This may be accomplished by stamping, by overmolding, by overmolding a stamped electrically conductive sealing plate and/ or by overmolding a metal injection molded seal plate. For example, the electrically conductive sealing plate 3112 may includes a series of upwardly extending flanges that are designed to matingly engage the insulator 3114. The insulator 3114 includes a shoe-like interface 3107 disposed at a distal end thereof which is dimensioned to engage the outer periphery of the housing 3116 in a slip-fit manner. The shoe-like interface 3107 may also be overmolded about the outer periphery of the jaw 3110 during a manufacturing step. It is envisioned that lead 3810 terminates within the shoe-like interface 3107 at the point where lead 3810 electrically connects to the seal plate 3112 (not shown). The movable jaw member 3110 also includes a wire channel (not shown) that is designed to guide cable lead 3810 into electrical continuity with sealing plate 3112.

All of these manufacturing techniques produce jaw member 3110 having an electrically conductive surface 3112 which is substantially surrounded by an insulating substrate 3114 and housing 3116. The insulator 3114, electrically conductive sealing surface 3112 and the outer, jaw housing 3116 are dimensioned to limit and/or reduce many of the known undesirable effects related to tissue sealing, e.g., flashover, thermal spread and stray current dissipation. Alternatively, it is also envisioned that jaw members 3110 and 3120 may be manufactured from a ceramic-like material and the electrically conductive surface(s) 3112 are coated onto the ceramic-like jaw members 3110 and 3120.

Jaw member 3110 also includes a pivot flange 3118 which includes protrusion 3137. Protrusion 3137 extends from pivot flange 3118 and includes an arcuately-shaped inner surface dimensioned to matingly engage the aperture 3135 of sleeve 3130 upon retraction thereof. Pivot flange 3118 also includes a pin slot 3119 that is dimensioned to engage pivot pin 3103 to allow jaw member 3110 to rotate relative to jaw member 3120 upon retraction of the reciprocating sleeve 3130. As explained in more detail below, pivot pin 3103 also mounts to the stationary jaw member 3120 through a pair of apertures 3101*a* and 3101*b* disposed within a proximal portion of the jaw member 3120.

It is envisioned that the electrically conductive sealing surface 3112 may also include an outer peripheral edge which has a pre-defined radius and the insulator 3114 meets the electrically conductive sealing surface 3112 along an adjoining edge of the sealing surface 3112 in a generally tangential position. At the interface, the electrically conductive surface 3112 is raised relative to the insulator 3114. Moreover, the electrically conductive surface 3112 and the insulator 3114, when assembled, form longitudinally-oriented knife slot 3115*a* defined therethrough for reciprocation of the knife blade 3510. It is envisioned that the knife channel 3115*a* cooperates with corresponding knife channel 3115*b* defined in stationary jaw member 3120 to facilitate longitudinal extension of the knife blade 3510 along a preferred cutting plane to effectively and accurately separate the tissue along a formed tissue seal.

Jaw member 3120 includes similar elements to jaw member 3110 such as jaw housing 3126 and an electrically conductive sealing surface 3122. Likewise, the electrically conductive surface 3122 and the insulative housing 3126, when assembled, include a longitudinally-oriented channel 3115*a* defined therethrough for reciprocation of the knife blade 3510. As mentioned above, when the jaw members 3110 and 3120 are closed about tissue, knife channels 3115*a* and 3115*b* allow longitudinal extension of the knife 3510 in a distal fashion to sever tissue along the tissue seal. It is also envisioned that the knife channel, e.g., knife channel 3115*b*, may be completely disposed in jaw member, e.g., jaw member 3120, depending upon a particular purpose.

As best seen in FIG. 26, jaw member 3120 includes a series of stop members 3150 disposed on the inner facing surfaces of the electrically conductive sealing surface 3122 to facilitate gripping and manipulation of tissue and to define a gap "G" of about 0.001 inches to about 0.006 inches between opposing jaw members 3110 and 3120 during sealing and cutting of tissue. It is envisioned that the series of stop members 3150 may be employed on one or both jaw members 3110 and 3120 depending upon a particular purpose or to achieve a desired result. A detailed discussion of these and other envisioned stop members 3150 as well as various manufacturing and assembling processes for attaching and/or affixing the stop members 3150 to the electrically conductive sealing surfaces 3112, 3122 are described in commonly-assigned, co-pending U.S. Application Serial No. PCT/US01/ 11413 entitled "VESSEL SEALER AND DIVIDER WITH NON-CONDUCTIVE STOP MEMBERS" by Dycus et al. which is hereby incorporated by reference in its entirety herein.

Jaw member 3120 is designed to be fixed to the end of a tube 3438 which is part of the distal articulating portion 3012*b*' of the shaft 3012 such that articulation of the distal portion 3012*b*' of the shaft 3012 will articulate the end effector assembly 3100. Jaw member 3120 includes a rear C-shaped cuff 3170 having a slot 3177 defined therein that is dimensioned to receive a slide pin 3171 disposed on an inner periphery of tube 3438. More particularly, slide pin 3171 extends substantially the length tube 3438 to slide into engagement (e.g., friction-fit, glued, welded, etc) within slot 3177. C-shaped cuff 3170 inwardly compresses to assure friction-fit engagement when received within tube 3438. Tube 3438 also includes an inner cavity defined therethrough that reciprocates the knife assembly 3500 upon distal activation thereof.

As explained in more detail below, fixed jaw member 3120 is connected to a second electrical potential through tube end effector support 3400 which is connects to steering cable 3902. More particularly, fixed jaw 3120 connects to the end effector support 3400 through a ground path connection from one or more steering cables, e.g., steering cable 3902, that includes a fuse clip, spring clip or other electro-mechanical connection at a proximal end thereof to provide electrical from the electrosurgical generator (not shown). Lead 3810 is carried through a channel defined within shaft 3012 (as explained in more detail below with respect to FIG. 32) and carries a first electrical potential to movable jaw 3110.

As mentioned above, the jaw members 3110 and 3120 may be opened, closed, articulated (and in some embodiments rotated) to manipulate and grasp tissue until sealing is desired. This enables the user to position and re-position the forceps 3010 prior to activation and sealing. As illustrated in FIGS. 21 and 23, the end effector assembly 3100 is articulatable about longitudinal axis "A-A" through rotation of wheels 3080 and 3090 of articulation assembly 3075 in either direction in the direction of arrows "R, L" and "U, D" (right, left and up, down, respectively) as explained in more detail below.

Once the tissue is grasped (within the required pressure range of about 3 kg/cm² to about 16 kg/cm²), the user then selectively applies electrosurgical energy to effectively seal tissue. Once sealed, the user then selectively advances the knife 3510 by actuating the trigger assembly 3070 to cut the tissue along the tissue seal. Actuation of the trigger assembly 3070 causes a cable 3504 extending through shaft 3012 and operatively coupled to a knife carrier 3505 for supporting the knife 3510 to move distally to thereby cut tissue along the tissue seal (See FIGS. 53 and 54). The operating features and relative movements of one envisioned trigger assembly 3070 are summarized below and more thoroughly described in the above-mentioned commonly-owned U.S. Pat. No. 7,156,846.

Figure 46:
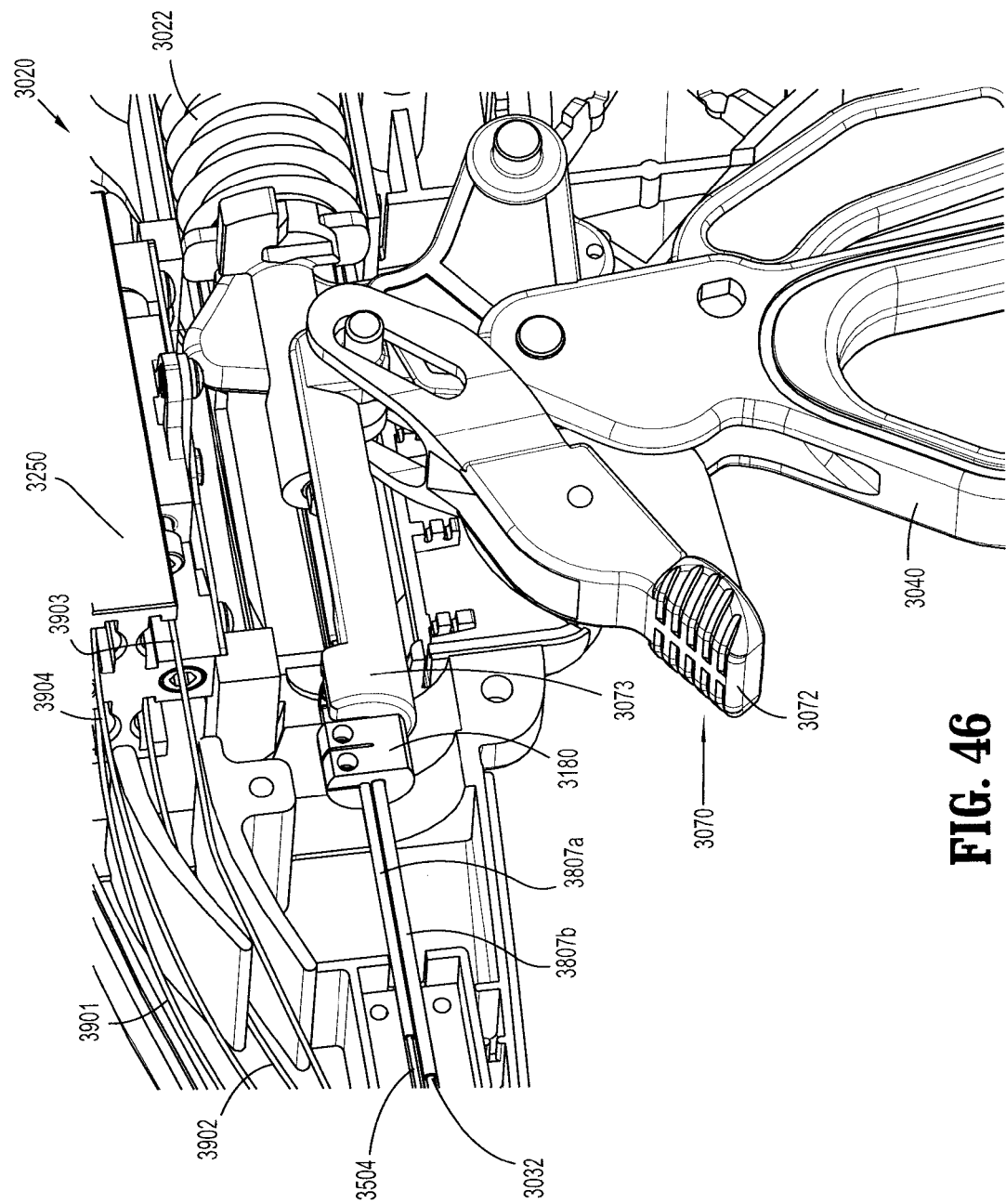
FIG. 46 is a greatly-enlarged internal view of the housing of the forceps and the internal components thereof.
Figure 47:
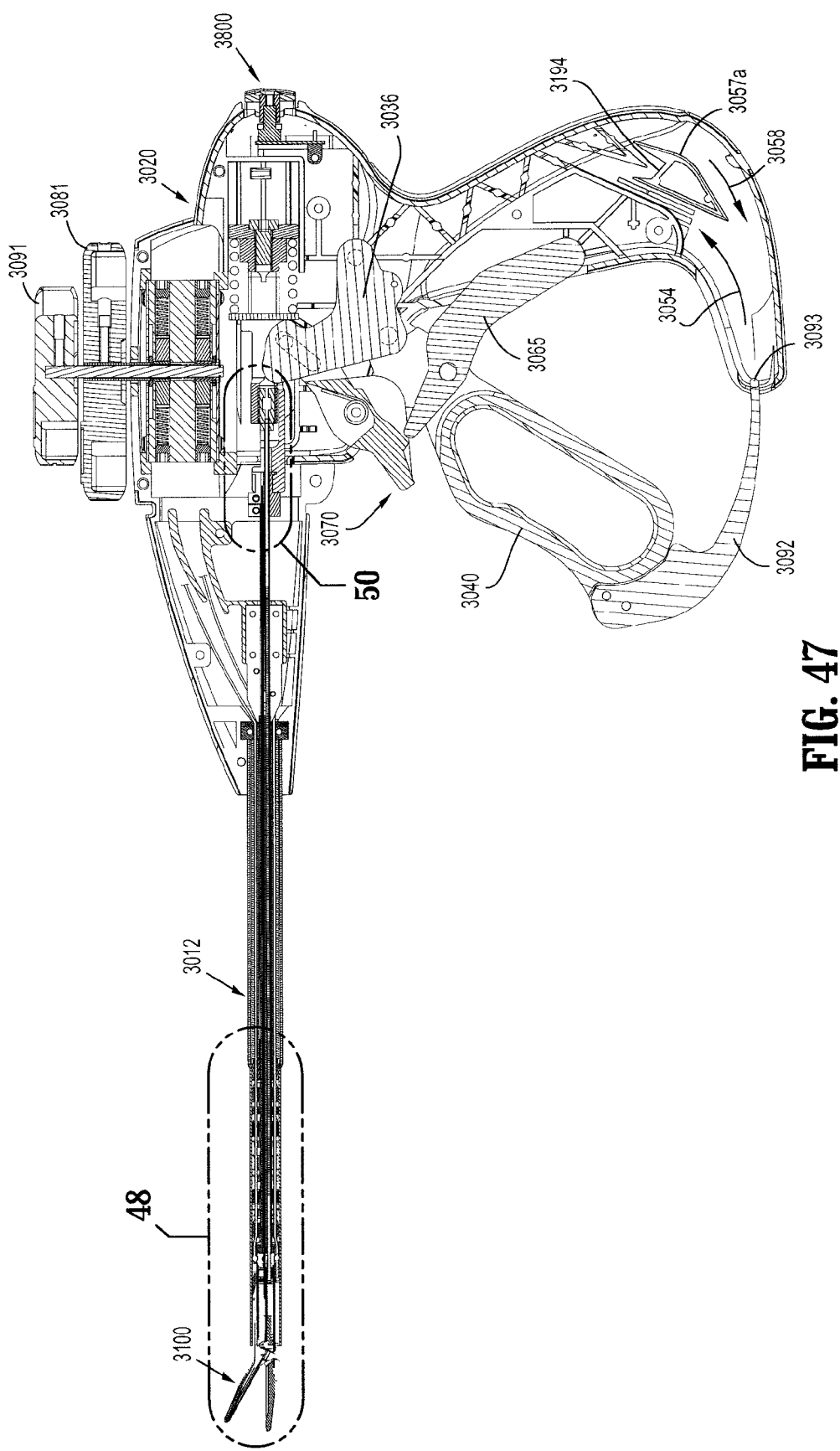
FIG. 47 is a side, cross section of the forceps of FIG. 1.
Figure 50:
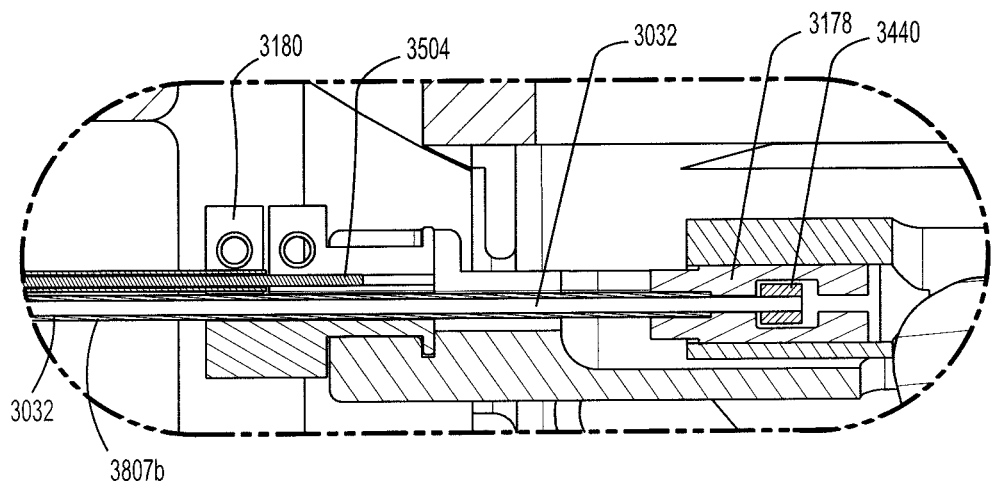
FIG. 50 is an enlarged view of the area of detail of FIG. 28.

Drive assembly 3024 is positioned within the housing 3020 between housing halves 3020a and 3020b. Drive assembly 3024 includes a drive rod 3032 and a compression mechanism 3021. Over-tube 3807b prevents drive rod 3032 from buckling along un-guided length (See FIG. 46). Compression mechanism 3021 includes a compression sleeve 3027 which is coupled to a spring mount 3026. The distal end 3028 of the compression sleeve 3027 is dimensioned to engage the nut 3178 disposed at the proximal end of drive rod 3032 such that longitudinal movement of the compression sleeve 3027 actuates the drive rod 3032. The proximal end of the compression sleeve 3027 is dimensioned to engage a barbell-shaped compression tab 3025 that is disposed within a longitudinal slot 3025s of the spring mount 3026. The compression sleeve 3027 also includes a longitudinal slot or channel 3025c which is longitudinally aligned with slot 3025s and is dimensioned to receive the cam piston 3038 of the cam link 3036 described above.

The proximal end of spring mount 3026 includes a circular flange ring 3023 that is dimensioned to bias the compression spring 3022 once the compression mechanism 3021 is assembled and seated within housing 3020. The distal end of spring mount 3026 includes a flange 3025f which restricts distal movement of the tab 3025 to within the slot 3025s of the spring mount 3026 and biases the opposite end the spring 3022.

As best seen in FIGS. 51-54, once assembled, spring 3022 is poised for compression atop spring mount 3026 upon actuation of the handle assembly 3030. More particularly, movement of the cam piston 3038 within slot 3025c (via movement of handle assembly 3030) moves the tab 3025 atop slot 3025s and reciprocates the compression sleeve 3027 within the spring mount 3026 to compress the spring 3022. Proximal movement of the compression sleeve 3027 imparts proximal movement to the drive rod 3032 which closes jaw members 3110 and 3120 about tissue. Release of the handle 3030 (as explained in more detail below), unbiases the spring 3022 to facilitate re-opening of the jaw members 3110 and 3120 relative to one another.

The trigger assembly 3070 which activates the knife assembly 3500 as described below with respect to FIGS. 53 and 54 includes an actuator 3073 having a cuff-like distal end 3078 that is dimensioned to receive the proximal rim of drive adapter 3180. A drive pin 3074 extends laterally from the proximal end of actuator 3073. As best shown in FIG. 23, the compression sleeve 3027 is dimensioned to slide internally within an actuator 3073 when the forceps 3010 is assembled. Likewise, the actuator 3073, when activated, can slide distally along the outer periphery of compression sleeve 3027 to actuate the knife assembly 3500 as described below with respect to FIGS. 23 and 54. The drive pin 3074 is dimensioned to ride along a pair of guide rails 3071a and 3071b disposed within a bifurcated tail portion of finger tab 3072 which includes ends 3076a and 3076b, respectively. The opposing ends of drive pin 3074 are also engaged in corresponding slots 3029a defined in each housing half, e.g., housing half 3020a (See FIG. 23).

A hinge or pivot pin 3077 mounts the finger tab 3072 between housing halves 3020a and 3020b. A torsion spring 3075 is incorporated within the trigger assembly 3070 to facilitate progressive and consistent longitudinal reciprocation of the actuator 3073 and knife rod 3032 to assure reliable separation along the tissue seal. In other words, the trigger assembly 3070 is configured in a proximal, "pre-loaded" configuration prior to activation. This assures accurate and intentional reciprocation of the knife assembly 3200. Moreover, it is envisioned that the "pre-load" configuration of the torsion spring 3075 acts as an automatic recoil of the knife assembly 3500 to permit repeated reciprocation through the tissue as needed. A plurality of gripping elements 3071 is preferably incorporated atop the finger tab 3072 to enhance gripping of the finger tab 3072.

Figure 55:
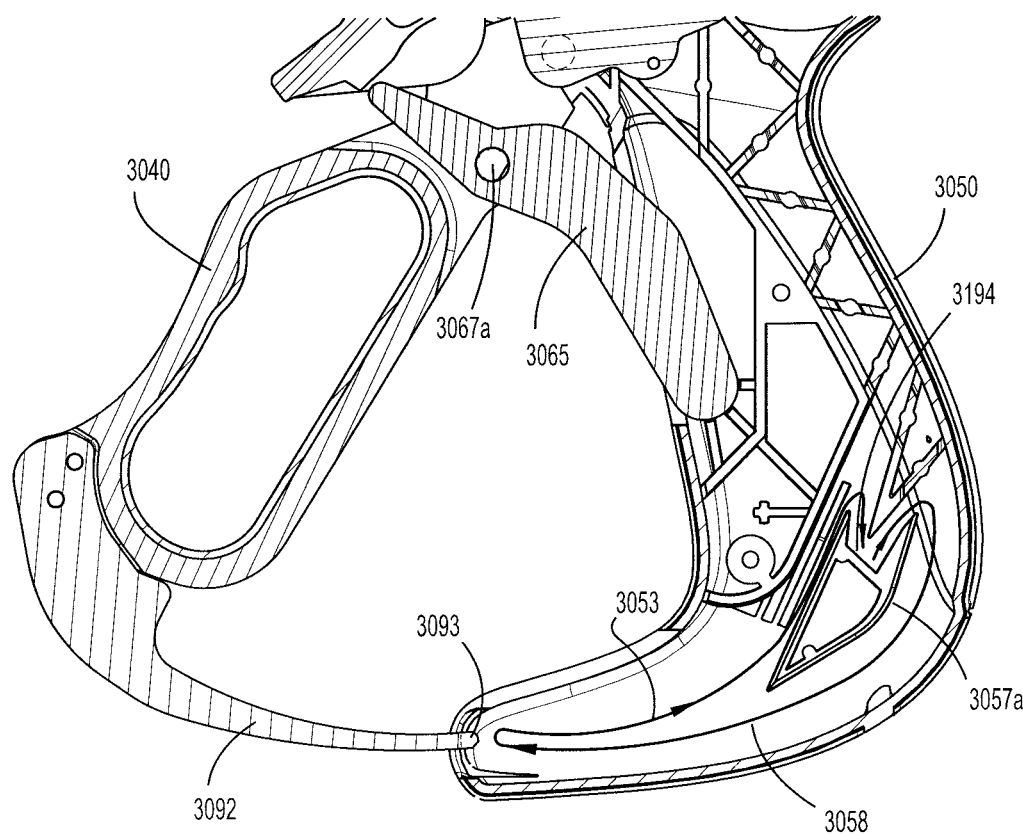
FIG. 55 is an internal view of the housing showing the relative movement of the locking mechanism when the actuating handle is released.

The trigger assembly 3070 is initially prevented from firing due to the unique configuration of the distal end 3063 of the link 3065 which abuts against the finger tab 3072 and passively "locks" the trigger assembly 3070 prior to actuation of the handle assembly 3030. Moreover, it is envisioned that the opposing jaw members 3110 and 3120 may be articulated and partially opened and closed without unlocking the trigger assembly 3070 which, as can be appreciated, allows the user to grip and manipulate the tissue without premature activation of the knife assembly 3500. As mentioned below, only when the t-shaped end 3093 of flange 3092 is completely reciprocated within channel 3054 and seated within a pre-defined catch basin 3062 (explained below) will the distal end 3063 of link 3065 move into a position which will allow activation of the trigger assembly 3070. The operating features and relative movements of these internal working components of the forceps 3010 are shown by phantom representation and directional arrows and are best illustrated in FIG. 55.

The operating features and relative movements of the internal working components of the forceps 3010 are shown by phantom representation in the various figures. As mentioned above, when the forceps 3010 is assembled a predefined channel 3052 is formed within the fixed handle 3050. The channel includes entrance pathway 3053 and an exit pathway 3058 for reciprocation of the flange 3092 and the t-shaped end 3093 therein. Once assembled, the two generally triangular-shaped members 3057a are positioned in close abutment relative to one another and define track 3192 disposed therebetween.

As the handle 3040 is squeezed and flange 3092 is incorporated into channel 3054 of fixed handle 3050, the driving assembly 3024, through the mechanical advantage of the four bar linkage, biases tab 3025 to compress spring 3022 against a rear flange ring 3023. As a result thereof, nut sleeve 3178 pulls the drive rod 3032 proximally which, in turn, closes jaw member 3110 onto jaw member 3120. It is envisioned that the utilization of a four-bar, cam-like pivot 3036 and drive assembly 3024 allows the user to selectively compress the coil spring 3022 a specific distance which, in turn, imparts a specific pulling load on the drive rod 3032 which is converted to a rotational torque about the jaw pivot pin 3103. As a result, a specific closure force can be transmitted to the opposing jaw members 3110 and 3120.

Figure 51:
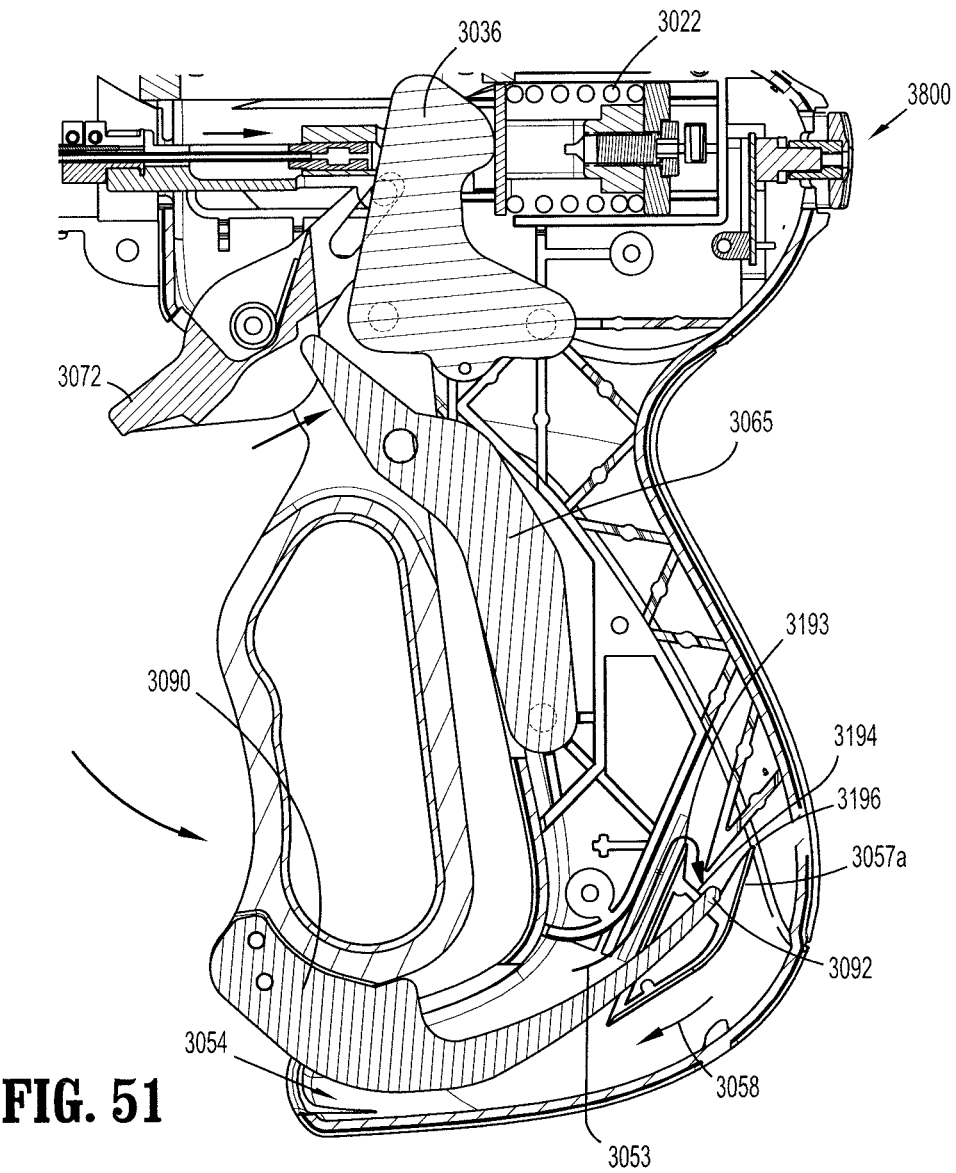
FIG. 51 is an internal view of the housing showing the relative movement of the drive assembly and a locking mechanism when the forceps is actuated.
Figure 52:
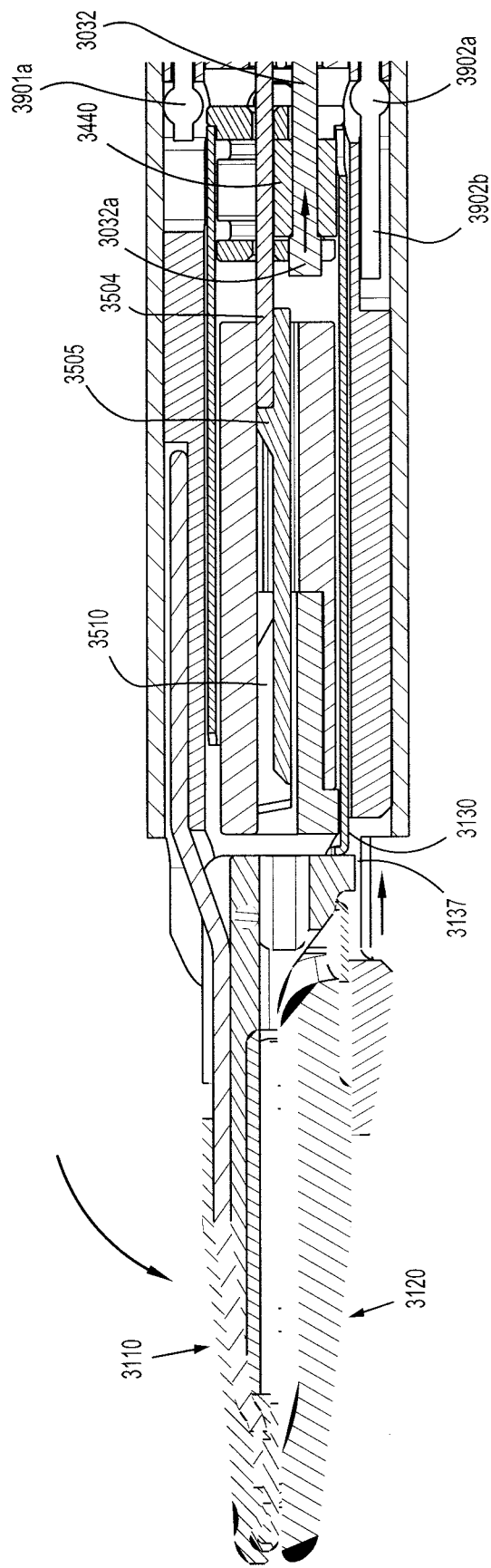
FIG. 52 is a greatly-enlarged cross section of the end effector assembly showing the relative movement of the drive rod and drive sleeve for actuating the jaw members.

FIG. 51 shows the initial actuation of handle 3040 towards fixed handle 3050 which causes the free end 3093 of flange 3092 to move generally proximally and upwardly along entrance pathway 3053. During movement of the flange 3092 along the entrance and exit pathways 3053 and 3058, respectively, the t-shaped end 3093 rides along track 3059 between the two triangular members 3057a. Once the desired position for the sealing site is determined and the jaw members 3110 and 3120 are properly positioned, handle 3040 may be compressed fully such that the t-shaped end 3093 of flange 3092 clears a predefined rail edge 3193 located atop the triangular-shaped members 3057a. Once end 3093 clears edge 3193, releasing movement of the handle 3040 and flange 3092 is redirected into a catch basin 3194 located at the proximal end of the triangular member 3057a. More particularly, upon a slight reduction in the closing pressure of handle 3040 against handle 3050, the handle 3040 returns slightly distally towards entrance pathway 3051 but flange 3092 re-directed towards exit pathway 3058. At this point, the release or return pressure between the handles 3040 and 3050, which is attributable and directly proportional to the release pressure associated with the compression of the drive assembly 3024, causes the end 3093 of flange 3092 to settle or lock within catch basin 3194. Handle 3040 is now secured in position within fixed handle 3050 which, in turn, locks the jaw members 3110 and 3120 in a closed position against the tissue.

Re-initiation or re-grasping of the handle 3040 again moves t-shaped end 3093 of flange 3092 generally proximally along exit pathway 3058 until end 3093 clears a lip 3196 disposed atop triangular-shaped members 3057a along exit pathway 3058. Once lip 3196 is sufficiently cleared, handle 3040 and flange 3092 are fully and freely releasable from handle 3050 along exit pathway 3058 upon the reduction of grasping/gripping pressure which, in turn, returns the jaw members 3110 and 3120 to the open, pre-activated position.

As mentioned above, the jaw members 3110 and 3120 may be opened, closed and articulated to manipulate tissue until sealing is desired. This enables the user to position and re-position the forceps 3010 prior to activation and sealing. As illustrated in FIG. 23, the end effector assembly 100 is articulatable about longitudinal axis "A-A" through rotation of the rotating wheels 3080 and 3090. The unique feed path of the cable lead 3810 through the housing, along shaft 3012 and, ultimately, to the jaw member 3110 enables the user to articulate the end effector assembly 3100 in multiple directions without tangling or causing undue strain on cable lead 3810.

Figure 53:
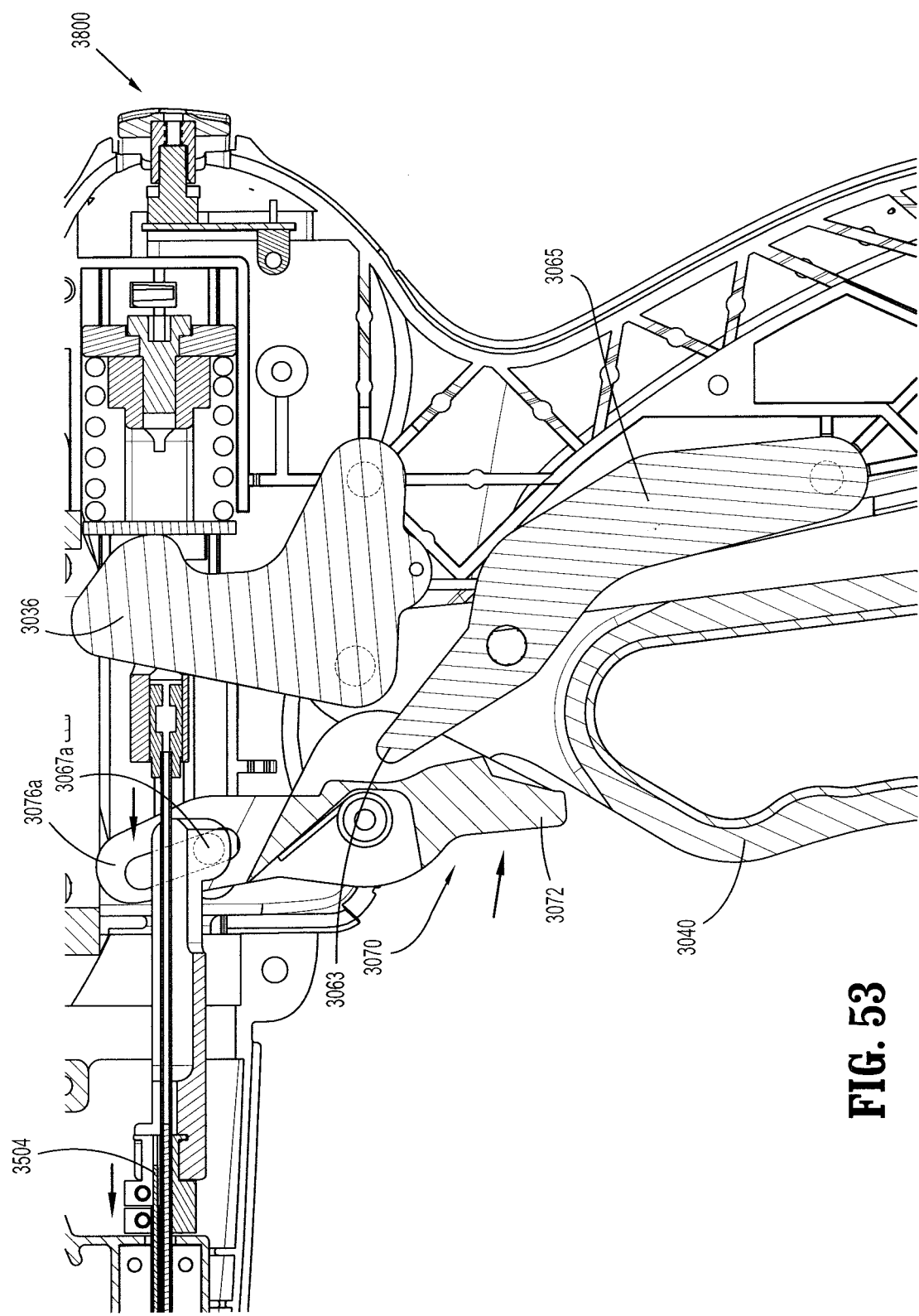
FIG. 53 is an internal view of the housing showing the relative movement of the knife assembly and knife rod when actuated.
Figure 54:
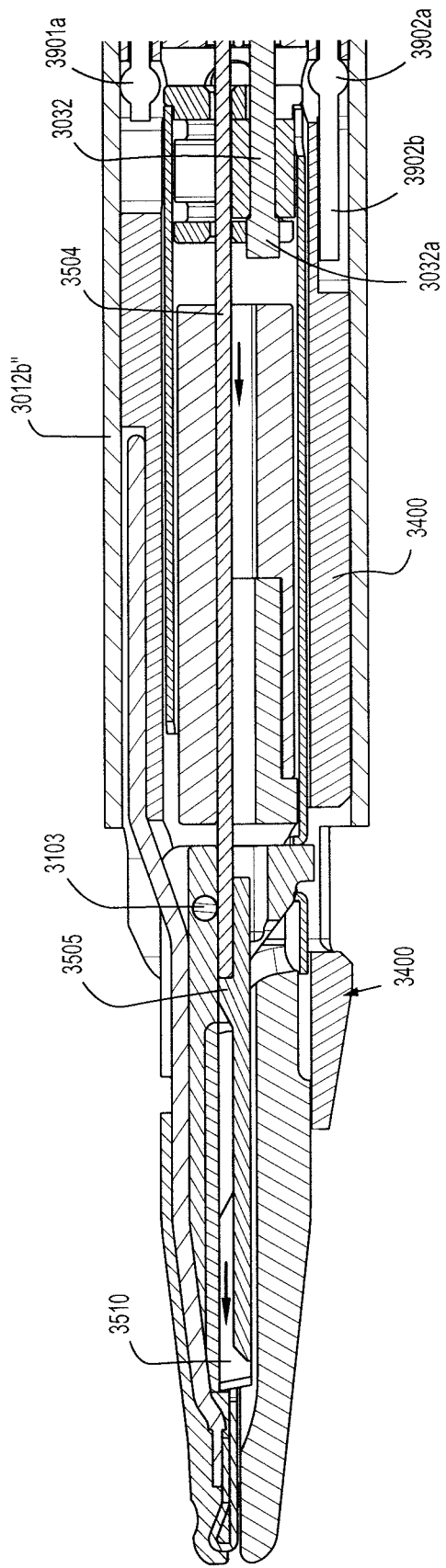
FIG. 54 is a greatly enlarged cross section of the end effector assembly showing the relative movement of the knife rod for cutting tissue disposed between the jaw members.

Again as best shown in FIG. 53, trigger assembly 3070 mounts atop movable handle 3040 and cooperates with the knife assembly 3500 to selectively translate knife 3510 through a tissue seal. More particularly, the trigger assembly 3070 includes a finger actuator 3072 and a U-shaped upwardly-extending flange 3076 having legs 3076a and 3076b. A pivot pin 3077 mounts the trigger assembly 3070 between housing halves 3020a and 3020b for selective rotation thereof. Legs 3076a and 3076b of the U-shaped flange 3076 each include a respective rails 3071a and 3071b defined therein which are each dimensioned to receive a free end of the respective drive pin 3074. The compression sleeve 3027 is dimensioned to slide internally within actuator 3073 when the forceps 3010 is assembled. Likewise, the actuator 3073, when activated, can slide distally along the outer periphery of compression sleeve 3027 to actuate the knife assembly 3500. The drive pin 3074 (or opposing pins (not shown)) is dimensioned to ride along a pair of guide rails 3071a and 3071b disposed within the u-shaped bifurcated tail portion of finger tab 3072 which includes ends 3076a and 3076b, respectively.

Proximal activation of the finger tab 3072 rotates the trigger assembly 3070 about pivot pin 3077 which, in turn, forces the actuator 3073 distally, which, as explained in more detail below, ultimately extends the knife 3510 through the tissue. Torsion spring 3075 biases the trigger assembly 3070 in a retracted position such that after severing tissue the knife 3510 and the trigger assembly 3070 are automatically returned to a pre-firing position.

Figure 34:
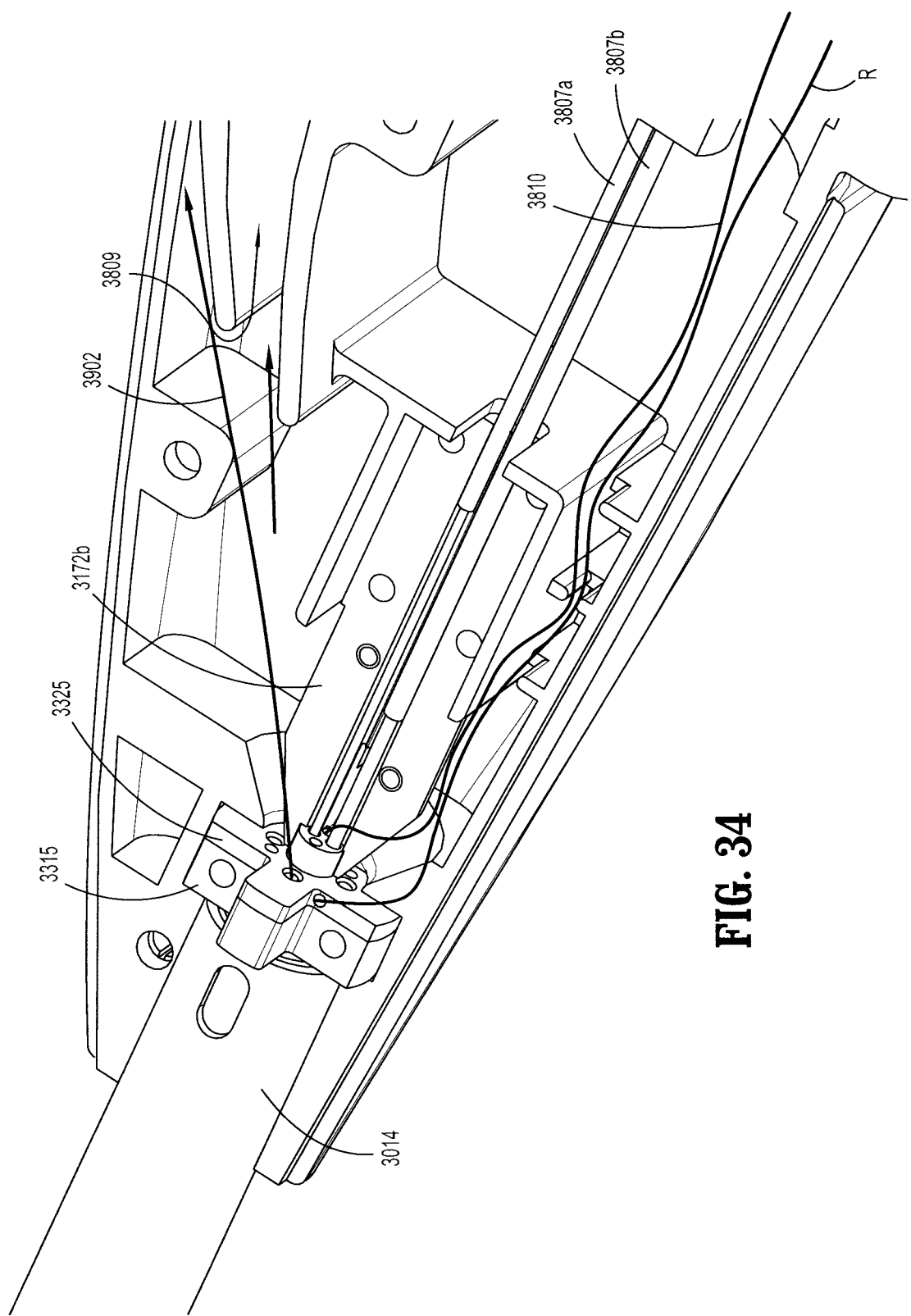
FIG. 34 is a greatly-enlarged, internal perspective view showing a path defined in the housing for guiding the steering cables therethrough.
Figure 35:
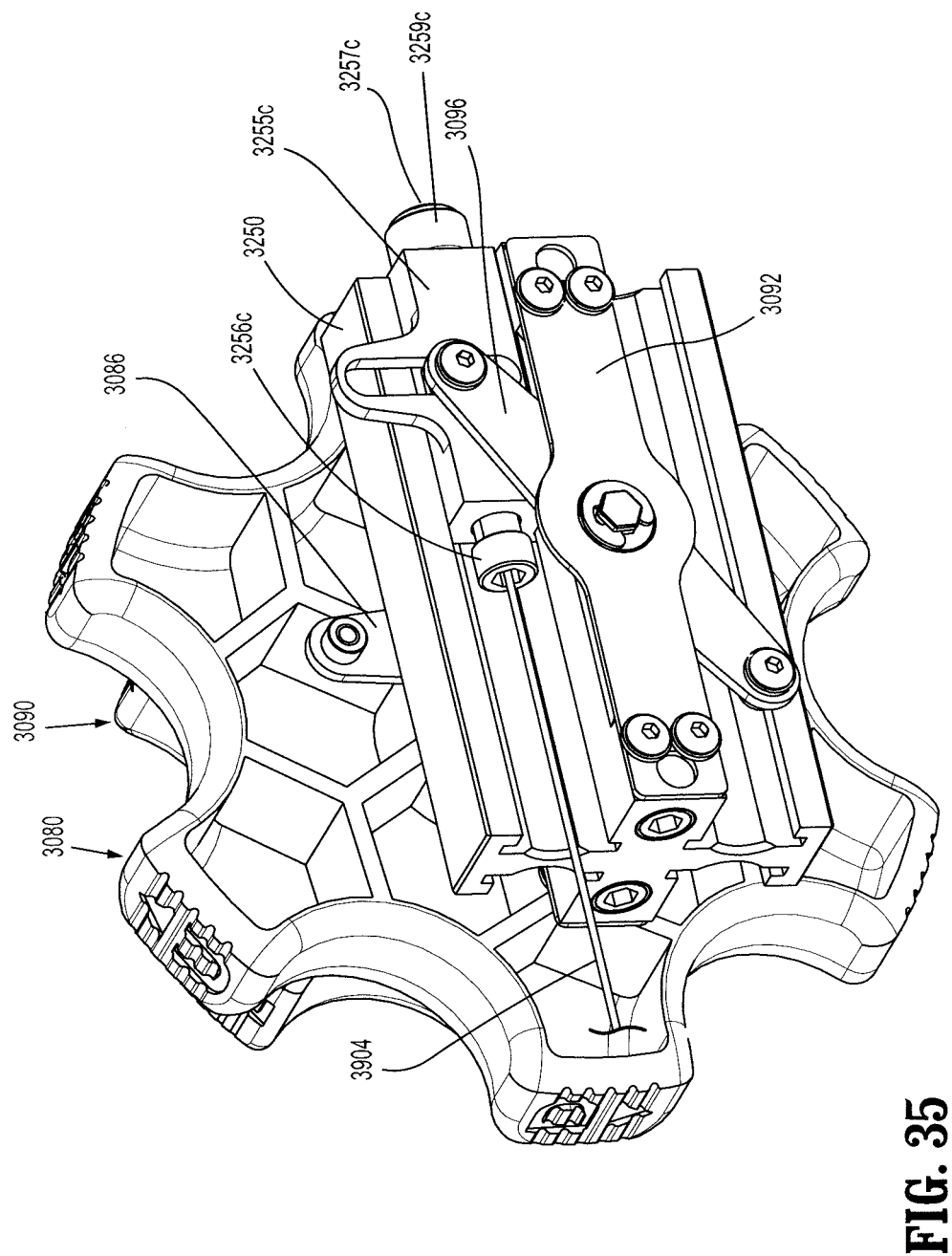
FIG. 35 is an enlarged, bottom perspective view of the articulation assembly of FIG. 21.
Figure 36:
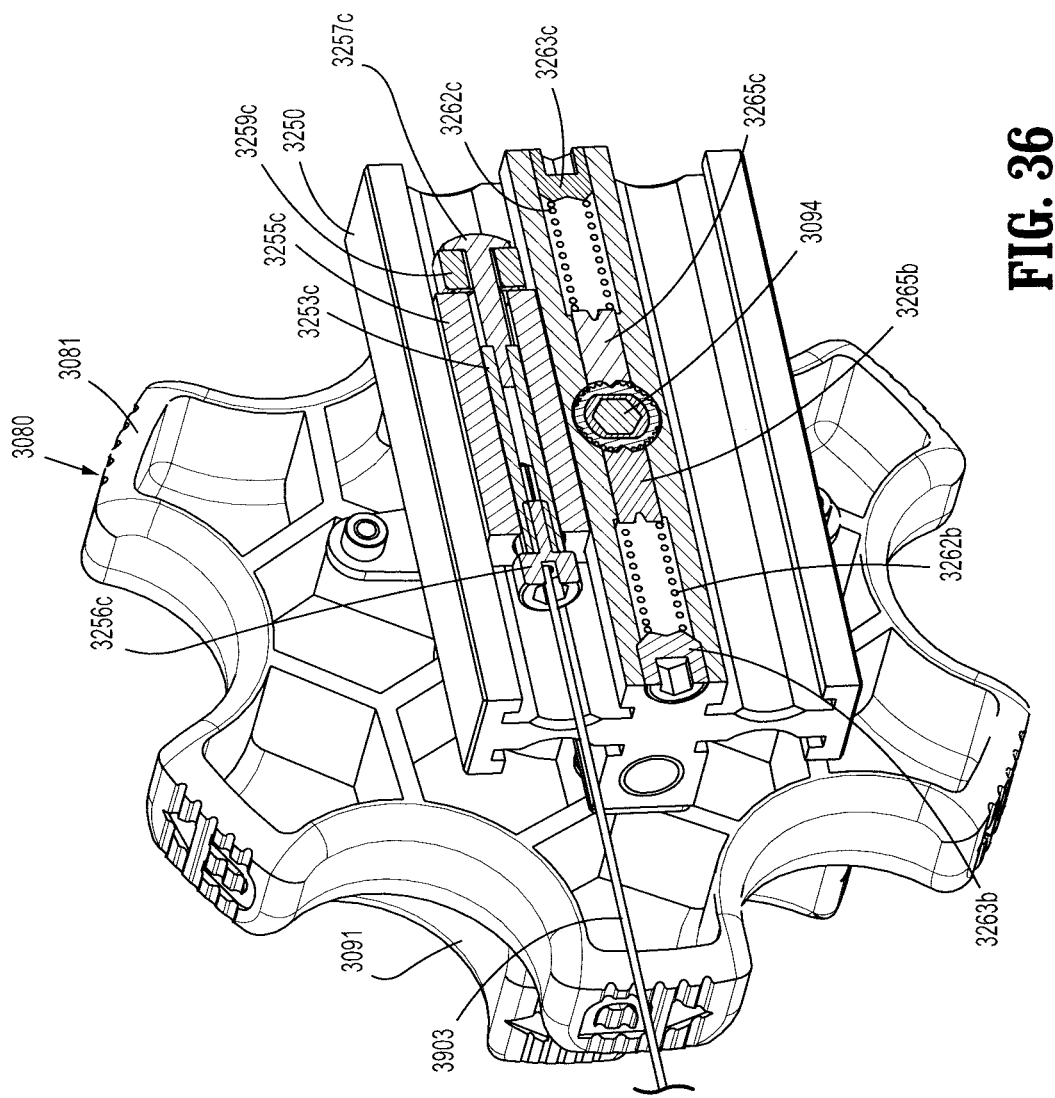
FIG. 36 is an enlarged, bottom perspective partial cross section of the articulation assembly of FIG. 15.

As best shown in the internal view of the FIG. 34, the electrical leads 3810 and control leads (not shown) are fed through the housing 3020 from electrosurgical cable 820. More particularly, the electrosurgical cable 3820 is fed into the bottom of the housing 3020 through fixed handle 3050. A ground lead (not shown) extends directly from cable 3820 and connects (via a fused clip or spring clip or the like) to steering cable 3902 to conduct the second electrical potential to fixed jaw member 3120. Control leads (not shown) extend from cable 3820 and connect to the hand switch or joy-stick-like toggle switch 3800. Lead 3810 extends from hand switch 3800 to jaw member 3110 as explained above.

Switch 3800 includes an ergonomically dimensioned switch plate 3805 which conforms to the outer shape of housing 3020 (once assembled). Switch 3800 may include a hermetically-sealed bushing 3803 that is operably disposed through switch plate 3805 and which protects electrical switch 3802 from fluids. Electrical switch 3802 is positioned atop and electrically coupled to a printed circuit board 3804 that regulates and controls the flow of electrosurgical energy to the jaw members 3110 and 3120 upon activation of switch 3804.

When switch 3800 is depressed, trigger lead 3810 carries the first electrical potential to jaw member 3110 thus activating a bipolar circuit. More particularly, when switch 3800 is depressed and the PC board 3804 is activated, the generator recognizes a voltage drop across control leads (not shown) from cable 3820 which initiates activation of the generator to supply a first electrical potential to jaw member 3110 and a second electrical potential to jaw member 3120. Switch 3800 acts as a control circuit and is protected or removed from the actual current loop which supplies electrical energy to the jaw members 3110 and 3120. This reduces the chances of electrical failure of the switch 3800 due to high current loads during activation. A footswitch (not shown) which may also be utilized with the forceps 3010, also operates in a similar manner, i.e., upon activation of the footswitch, the generator recognizes a voltage drop across the input and output leads of the footswitch which, in turn, signals the generator to initiate electrosurgical activation of the jaw members 3110 and 3120.

A safety switch or circuit (not shown) may be employed with the printed circuit board such that the switch cannot fire unless the jaw members 3110 and 3120 are closed and/or unless the jaw members 3110 and 3120 have tissue held therebetween. In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Various sensor mechanisms and feedback systems are described in commonly-owned, co-pending U.S. patent application Ser. No. 10/427,832 entitled "METHOD AND SYSTEM FOR CONTROLLING OUTPUT OF RF MEDICAL GENERATOR" filed on May 1, 2003 the entire contents of which are incorporated by reference hereinabove.

It is contemplated that utilizing a cable feed path 3809 (See FIG. 34) for cable lead 3810 and by utilizing steering cable 3902 to carry the first and second electrical potentials, respectively, not only electrically isolates each jaw member 3110 and 3120 but also allows the jaw members 3110 and 3120 to pivot about pivot pin 3103 without unduly straining or possibly tangling cable lead 3810. Moreover, it is envisioned that the simplicity of the electrical connections greatly facilitates the manufacturing and assembly process and assures a consistent and tight electrical connection for the transfer of energy through the tissue.

Figure 24A:
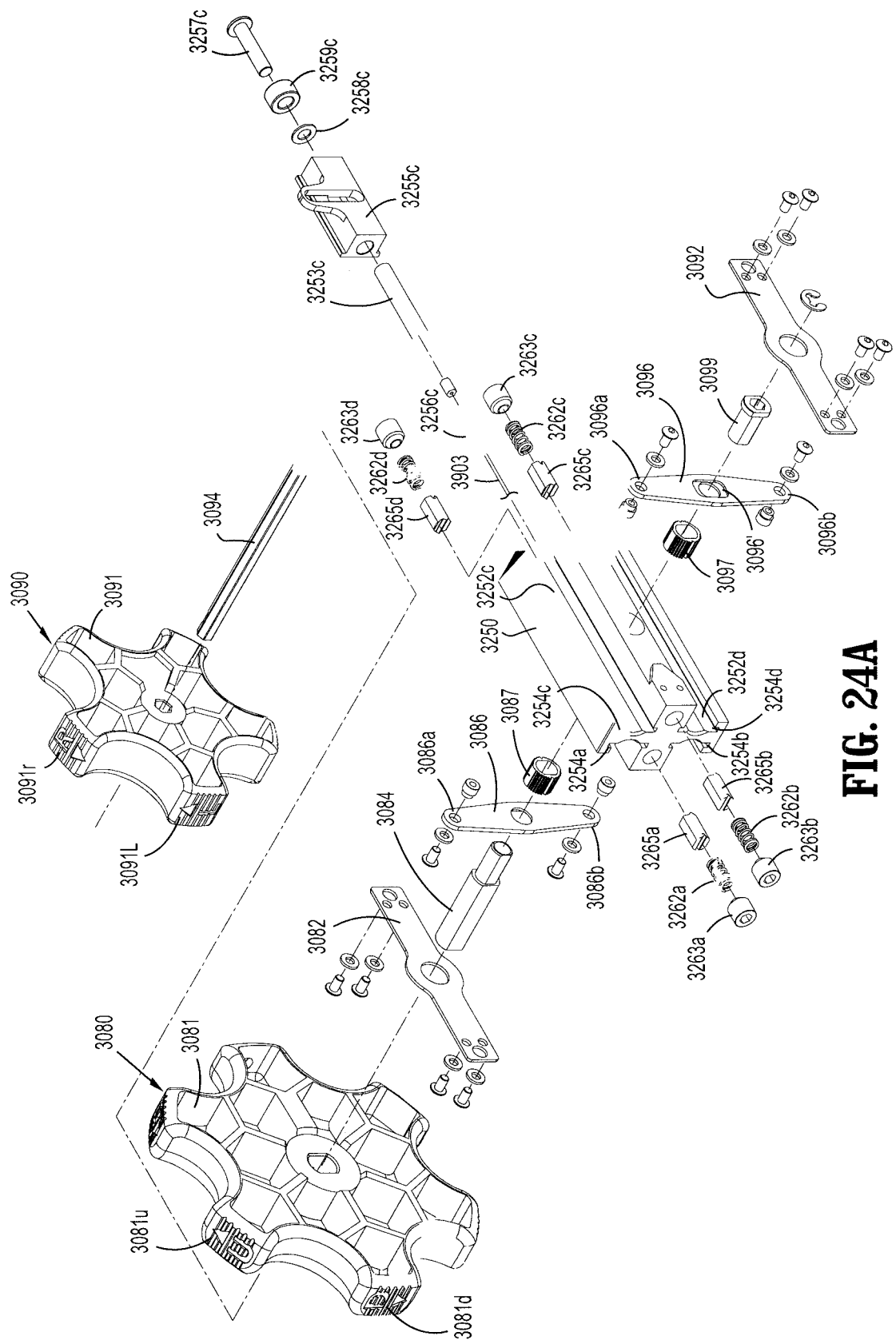
FIG. 24A is an enlarged, exploded perspective view of the articulating assembly of FIG. 21.
Figure 24B:
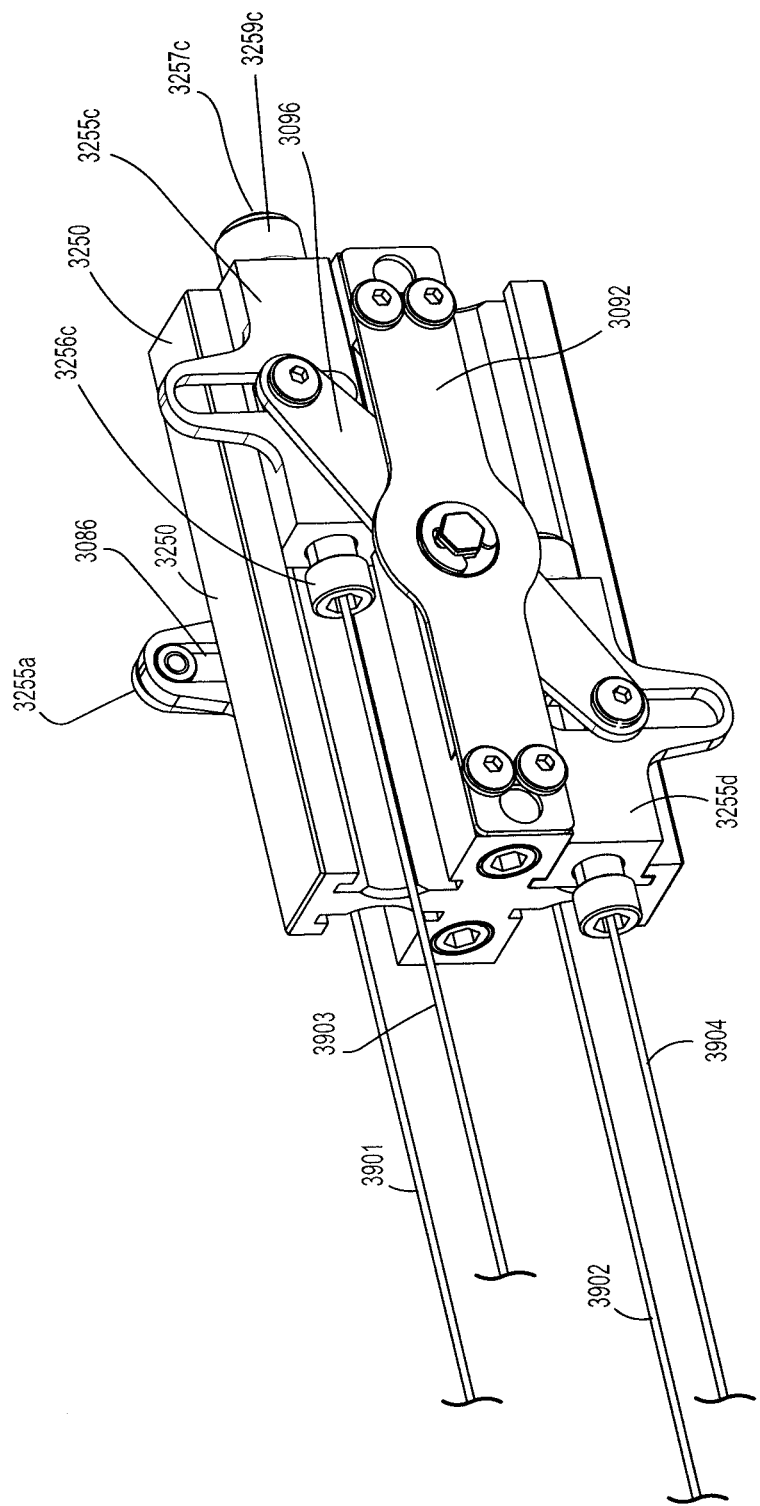
FIG. 24B is an enlarged perspective view of a slider of the articulating assembly.
Figure 24C:
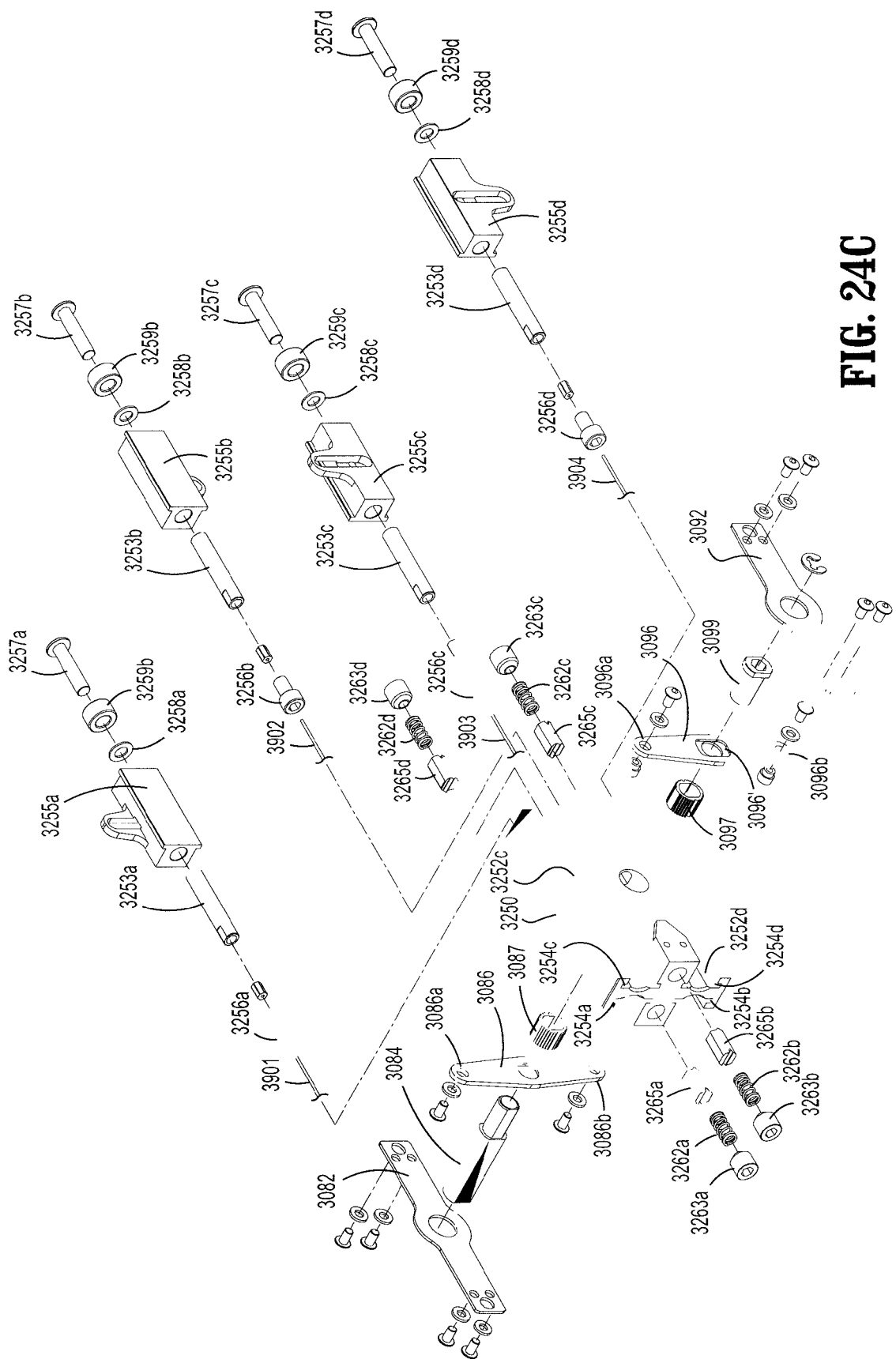
FIG. 24C is an enlarged exploded perspective view of the slider of FIG. 24B.

FIGS. 24A and 24C show exploded views of the two articulation assemblies 3080 and 3090 that allow selective articulation of the end effector assembly 3100 to facilitate the manipulation and grasping of tissue in tight surgical cavities. More particularly, the two rotating assemblies 3080 and 3090 include selectively rotatable wheels, 3081 and 3091, respectively, that sit atop the housing 3020. Each wheel, e.g., wheel 3081, is independently moveable relative to the other wheel, e.g., 3091, and allows a user to selectively articulate the end effector assembly 3100 along a given axis of articulation relative to the longitudinal axis "A-A." For example and as explained in more detail below, rotation of wheel 3091 articulates the end effector assembly 3100 along arrows R, L (or right-to-left articulation) and rotation of wheel 3081 articulates the end effector assembly along arrows U, D (or up and down articulation) (See FIGS. 21 and 38-45).

Turning in detail to the exploded views of FIGS. 24A and 24C, articulation assembly 3080 operably couples to an articulation block 3250 that mounts within housing 3020. More particularly, an elongated hollow spindle 3084 mechanically interfaces at one end with the articulation wheel 3081 (set screw or friction-fit manner) such that rotation of the wheel 3081, in turn, rotates the spindle 3084. The opposite end of the spindle 3084 mechanically interfaces with a rotation link 3086. The link 3086 rotates in reference to the articulation block 3250. The link plate 3082 prevents link 3086 from sliding out of a receiving hole defined in the articulation block 3250 and the link 3082 is attached to the block by bolts or other mechanical connections.

Link 3086, in turn, mounts to the articulation block 3250 such that each end 3086a and 3086b couples to a respective slider 3255a and 3255b (See FIGS. 24B and 24C) that each ride along a series of predefined rails 3254a and 3254b disposed in the articulation block 3250. The sliders 3255a and 3255b each couple to an end of a respective steering cable 3901 and 3902 (See FIG. 24C) via a series of tensioning bolts 3256a-3256b, sleeves 3253a-3253b, washers 3258a-3258b, elastic compression bushings or springs 3259a-3259b and tensioning bolts 3257a-3257b such that rotation of the wheel 3081 in a given direction causes the respective sliders 3255a and 3255b to slide oppositely relative to one another within rails 3254a and 3254b to pull or contract a respective steering cable 3901-3902. For example, rotation of wheel 3081 in a clockwise direction (DOWN "D"), causes the rotational link 3086 to rotate clockwise which, in turn, causes end 3086a to rotate distally and end 3086b to rotate proximally. Tensioning bolts 3257a-3257b and bushings 3259a-3259b are designed to maintain the tension of the cables 3901-3902 within the respective sliders 3255a and 3255b.

As a result thereof, slider 3255a moves distally and slider 3255b moves proximally causing steering cable 3901 to move distally and steering cable 3902 to move proximally thus causing end effector assembly to flex DOWN "D". When wheel 3081 is rotated counter-clockwise, the sliders 3255a and 3255b move in an opposite direction on rails 3254a and 3254b and end effector assembly 3100 has an opposite effect, i.e., the end effector assembly 3100 is articulated in an UP "U" direction (See FIG. 45). Rotational movement of wheel 3081 moves the end effector along an UP "U" and DOWN "D" plane relative to the longitudinal axis "A-A" (See FIG. 21). The cam-like connection between the sliders 3255a and 3255b and the link 3086 offers increased mechanical advantage when a user increases the articulation angle, i.e., the cam-like connection helps overcome the increasing resistance to articulation as the flexible shaft 3012b' is articulated in a given direction.

Wheel assembly 3090 attaches to articulation block 3250 in a similar manner. More particularly, wheel 3091 operably engages to one end of a solid spindle 3094 which, in turn, attaches at an opposite end thereof to rotational link 3096 disposed on an opposite end of the articulation block 3250. Spindle 3094 is dimensioned for insertion through elongated spindle sleeve 3084 in a manner that spindle 3094 is rotatable relative to spindle sleeve 3084. Shaft 3094 passes through the spindle sleeve 3084 and engages a locking nut 3099, which is, in turn, welded to rotational link 3096. To accomplish this purpose, spindle sleeve 3084 includes an outer-shaped periphery, rotational link 3096 includes a locking recess 3096' engraved therein and the locking nut 3099 is utilized to seat within link 3096 and lock spindle 3094 relative to spindle sleeve 3084 such that rotational movement of spindle 3094 does not cause rotation of spindle sleeve 3084. Indexing wheels 3087 and 3097 are utilized on either side of the articulation block 3250 to assure secure engagement of the spindles 3084 and 3094 therein and to provide notches that interact with the slides 3265a-3265d to index the wheels 3081 and 3091 for proper fine positioning and secure indexing thereof. The slides 3265a-3265d are tensioned via respective tensioning screws 3263a-3263d and springs 3262a-3262d. The largest notch on the indexing wheels 3087, 3097 is designed to indicate a so-called "home" orientation for a respective articulation wheel 3081, 3091. As the spindles 3084 and 3094 are rotated, the indexing wheels 3087 and 3097 act like miniature ratchet mechanisms to enhance fine discreet adjustment of each articulation wheel 3081 and 3091 relative to the longitudinal axis.

As mentioned above, spindle 3094 connects at an opposite end thereof to rotational link 3096. A link plate 3092 is utilized to secure the link to the opposite side of the articulation block 3250. Much like link 3086, link 3096 operably couples to a pair of sliders 3255c and 3255d which are configured to ride in rails 3254c and 3254d defined on the opposite side of the articulation block 3250. More particularly, each end 3096a and 3096b of link 3096 couples to a respective slider 3255c and 3255d (See FIGS. 24B and 24C) that each ride along rails 3254c and 3254d disposed in the articulation block 3250. The sliders 3255c and 3255d each couple to an end of a respective steering cable 3903 and 3904 via a series of tensioning bolts 3256c-3256d, sleeves 3253c-3253d, washers 3258c-3258d, elastic compression bushings or springs 3259c-3259d and tensioning bolts 3257c-3257d such that rotation of the wheel 3091 in a given direction causes the respective sliders 3255c and 3255d to slide oppositely relative to one another within rails 3254c and 3254d to pull or contract a respective steering cables 3903-3904. For example, rotation of wheel 3091 in a clockwise direction (RIGHT "R"), causes the rotational link 3086 to rotate clockwise which, in turn, causes end 3096a to rotate distally and end 3096b to rotate proximally (See FIGS. 40-42). As a result thereof, slider 3255c moves distally and slider 3255d moves proximally causing steering cable 3903 to move distally and steering cable 3904 to move proximally thus causing end effector assembly 3100 to flex to the RIGHT "R". When wheel 3091 is rotated counter-clockwise, the sliders 3255c and 3255d move in an opposite direction on rails 3254c and 3254d and end effector assembly 3100 has an opposite effect, i.e., the end effector assembly 3100 is articulated in a LEFT "L" direction (See FIG. 41). Rotational movement of wheel 3091 moves the end effector along an RIGHT and LEFT plane relative to the longitudinal axis "A-A."

As can be appreciated, the articulation assembly 3075 enables a user to selectively articulate the distal end of the forceps 3010 (i.e., the end effector assembly 3100) as needed during surgery providing greater flexibility and enhanced maneuverability to the forceps 3010 especially in tight surgical cavities. By virtue of the unique arrangement of the four (4) spring loaded steering cables 3901-3904, each articulating assembly 3080 and 3090 provides a positive drive, back and forth motion to the end effector assembly 3100 that allows the end effector assembly 3100 to remain in an articulated configuration under strain or stress as the forceps 3010 is utilized and/or prevent buckling through a range of motion. Various mechanical elements (not shown) may be utilized to enhance this purpose including guide paths 3809 through the housing 3020 (See FIG. 34), friction fits sleeves that prevent buckling 3807a, 3807b (See FIG. 34), ratchet like interfaces 3087, 3097 (See FIG. 24A) and tensioning/locking mechanisms or pins 3265c (See FIG. 24A). In addition, the flexible shaft 3012 and end effector assembly 3100 may also be manipulated to allow multi-directional articulation through the manipulation of both wheels 3081 and 3091 simultaneously or sequentially thereby providing more maneuverability to the forceps.

Figure 37:
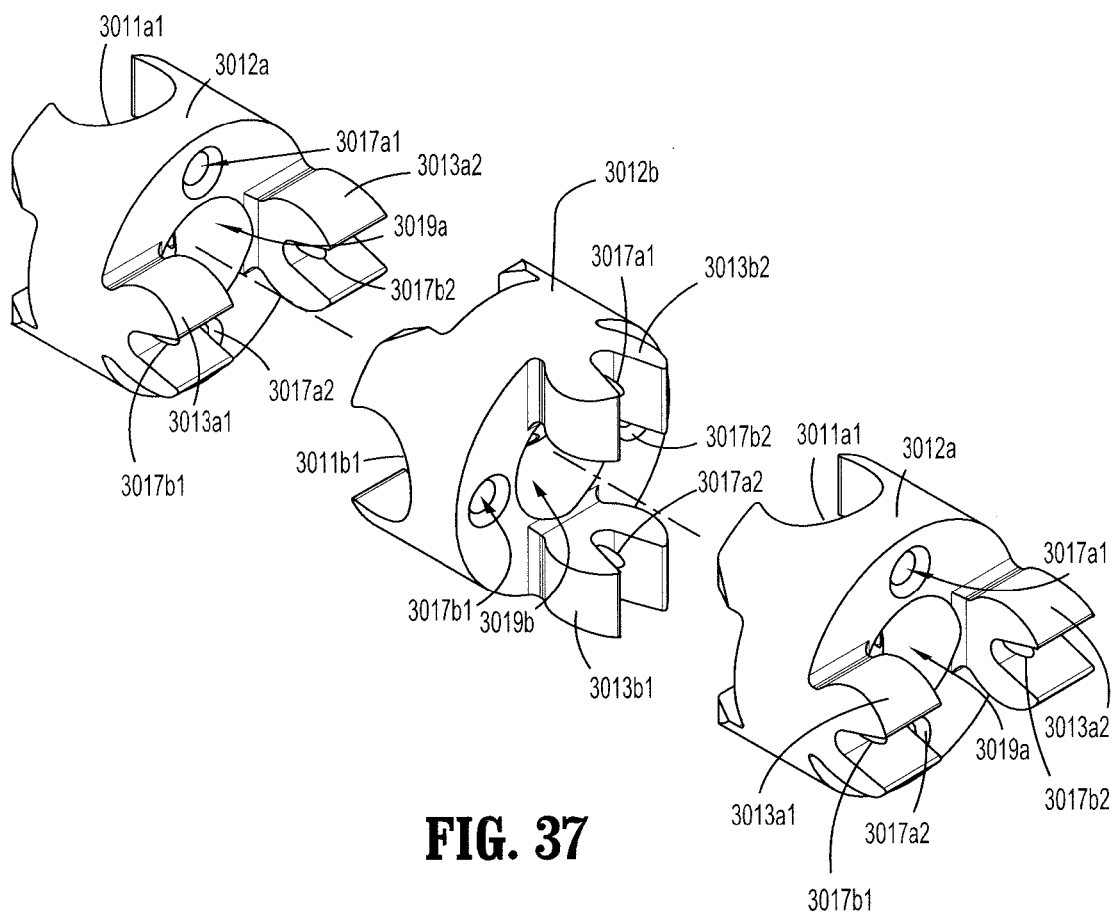
FIG. 37 is a greatly-enlarged, perspective view of a plurality of joints that are configured to nestingly engaged one another to form the flexible portion of the shaft.
Figure 40:
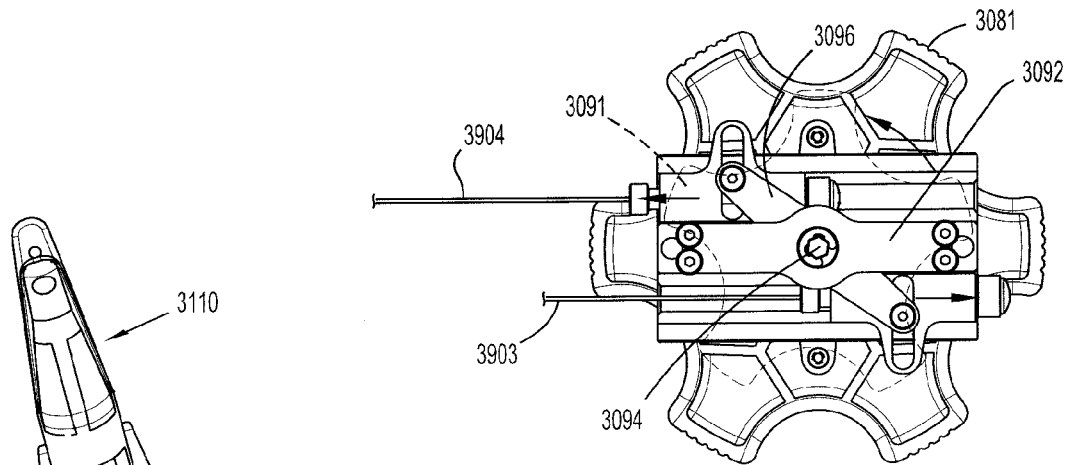
FIG. 40 is an enlarged, bottom view of the articulating assembly showing the orientation of two steering cables of the plurality of steering cables when articulation the flexible shaft to the "RIGHT" (R)
Figure 42:
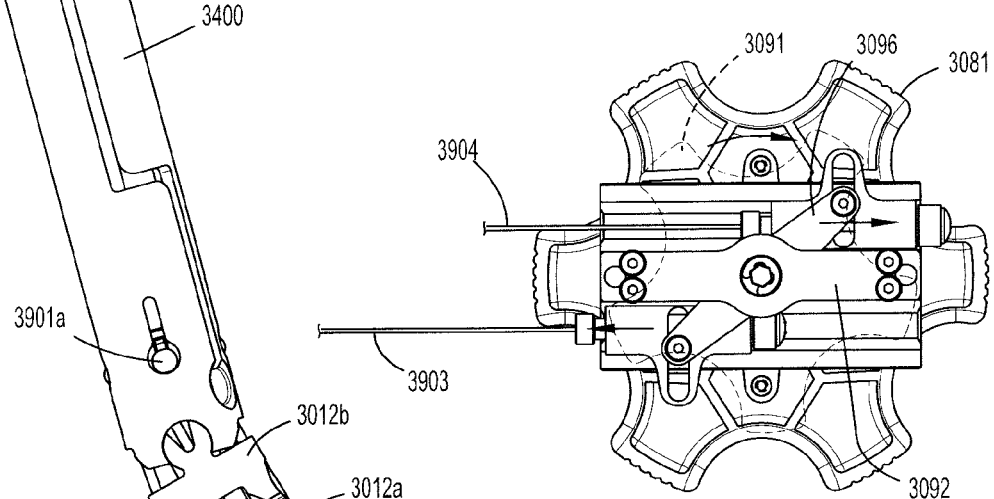
FIG. 42 is an enlarged, bottom view of the articulating assembly showing the orientation of two steering cables of the plurality of steering cables when articulation the flexible shaft to the "LEFT" (L)
Figure 41:
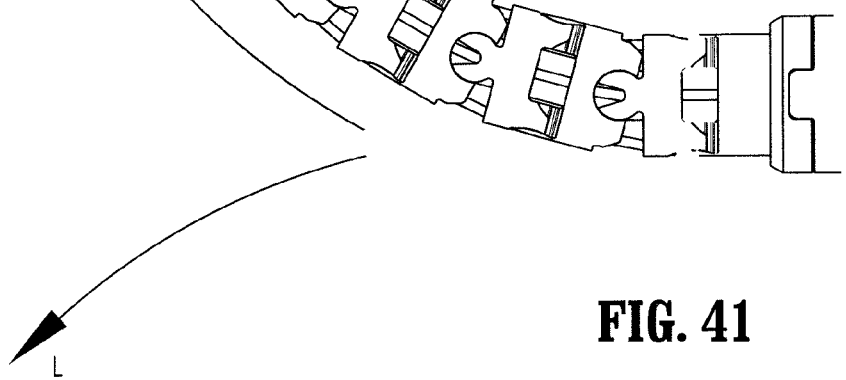
FIG. 41 is an enlarged, top view of the flexible shaft in a "RIGHT" (R) articulated orientation.
Figure 44:
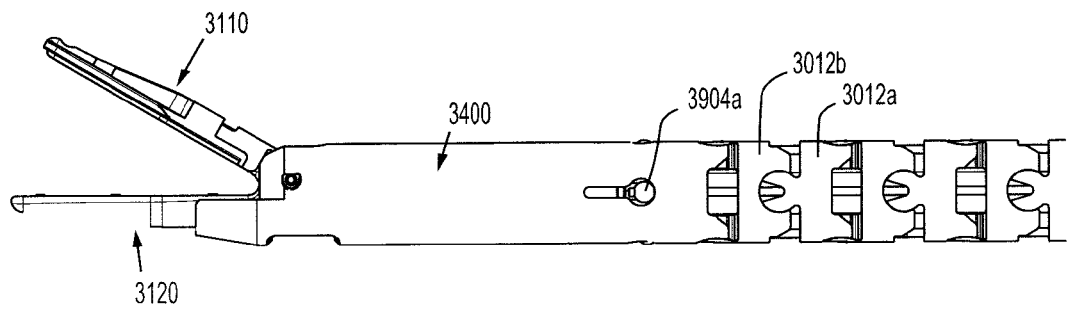
FIG. 44 is a side view of the end effector assembly in an open configuration.
Figure 45:
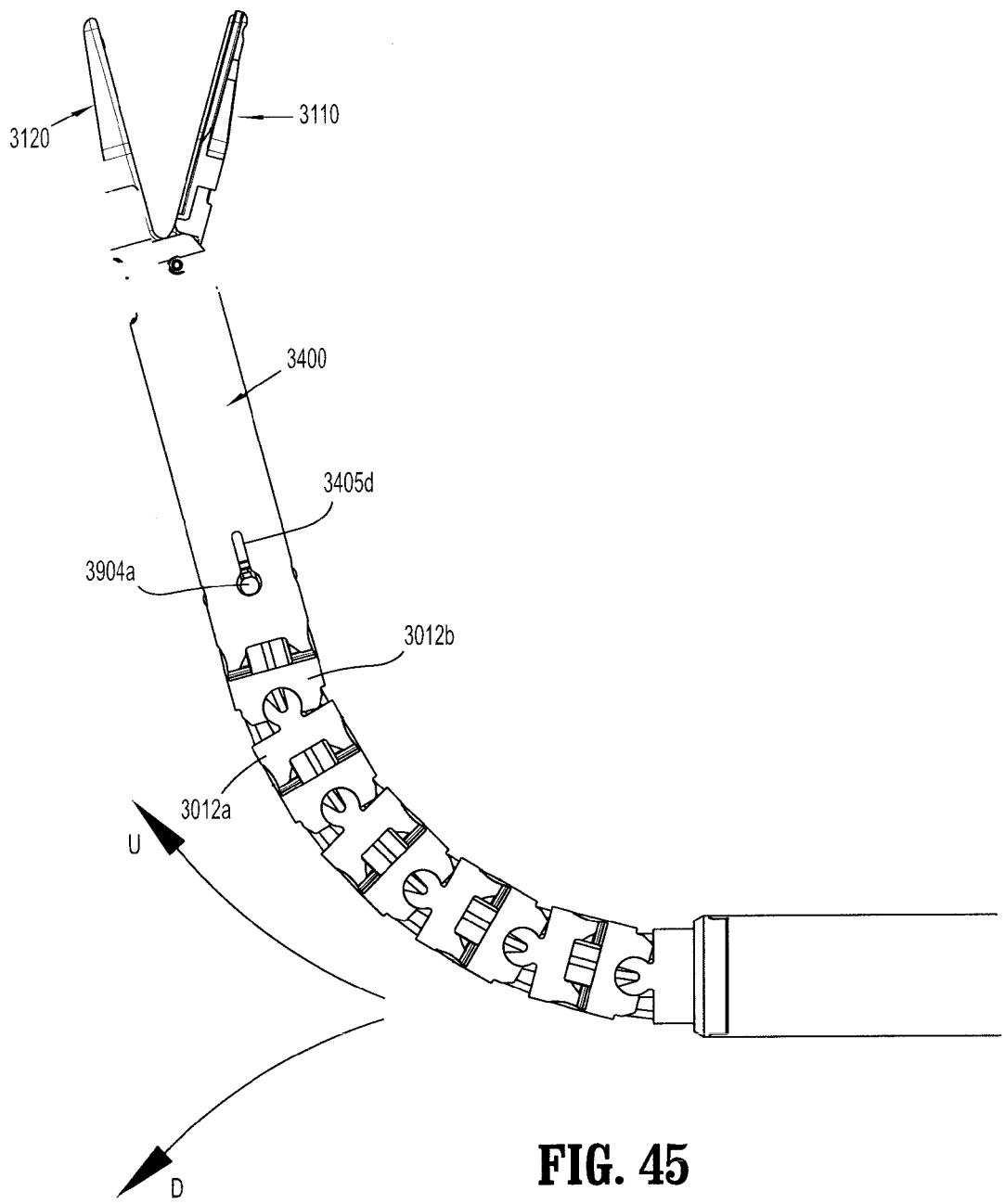
FIG. 45 is an enlarged, side view of the flexible shaft in a "UP" (U) articulated orientation.

Turning now to the flexible shaft and with particular respect to FIGS. 25, 28-32, 37, 41 and 45, the forceps 3010 includes a plurality of joints 3012a and 3012b that are nestingly arranged in alternating series to form flexible shaft 3012. The distal end 3016 of shaft 3012 mechanically engages the end effector assembly 3100 and the proximal end 3014 of the shaft 3012 mechanically engages the housing 3020. As best shown in FIG. 37, there are two sets of joints that are nestingly arranged in alternating series, namely, joints 3012a and 3012b. Both joints 3012a and 3012b are similar in construction but are offset relative to one another by ninety degrees) (90°) to facilitate and enhance relative movement between joints 3012a and 3012b. Joint 3012a includes a pair of distal knuckles 3013a1 and 3013a2 and pair of opposing proximal clevises 3011a1 and 3011a2 formed therewith. Joint 3012b includes a pair of distal knuckles 3013b1 and 3013b2 and pair of opposing proximal clevises 3011b1 and 3011b2 formed therewith. Each knuckle 3013a1, 3013a2 operatively engages a corresponding clevis 3011b1, 3011b2 of an adjacent joint 3012b. Joint 3012a also defines a central lumen 3019a formed therein and a pair of opposed lumen pairs 3017a1 and 3017a2 and 3017b1 and 3017b2 formed on the four sides of central lumen 3019a. Joint 3012b likewise defines a central lumen 3019b formed therein and the pairs of opposed lumens 3017a1, 3017a2 and 3017b1, 3017b2 formed on the sides of central lumen 3019a.

A flexible tubing 3012b" covers the distal portion of shaft 3012 (See FIG. 21) and the flexible shaft 301b' (See FIG. 25). Moreover, the tubing secures the lead 3810 within channel 3850 defined within end effector support 3400 (See FIG. 28). Flexible tubing 3012b" may also be configured to seal various lubricants within the flexible portion 3012b' of shaft 3012 and prevent the ingress of body fluids into the forceps 3010 during use.

Steering cables 3901-3904 slideably extend through lumens 3017a1, 3017a2 and 3017b1, 3017b2 of joints 3012a and 3012b, respectively, and operably couple to an end effector support 3400 (See FIG. 25). More particularly, each steering cable 3901-3904 includes a ball-like mechanical interface at a distal end thereof, namely, interfaces 3901a-3904a, that are configured to securely mate within a corresponding recess defined in the end effector support 3400. More particularly, interface 3901a engages recess 3405a (See FIG. 25), interface 3902a engages recess 3405c (See FIG. 27), interface 3903a engages recess 3405b (See FIG. 25) and interface 3904a engages recess 3405d (See FIG. 45). As explained above, actuation of one or both articulation wheels 3081 and 3091 pull and release a pair of steering cables 3901, 3902 and 3903, 3904 to articulate the end effector assembly 3100 as desired. Offsetting the flexible joints 3012a and 3012b relative to one another by ninety degrees) (90°) allows articulation of the forceps 3100 in two planes.

As best shown in FIG. 25, the steering cables 3901-3904 are fed through the shaft 3012 through a series of passageways defined therein. More particularly, a cross shaped cable guide adapter 3315 and guide adapter liner or washer 3325 initially orient the cables 3901-3904 for passage though an outer tube 3310 at 90° degree angles relative to one another. The adapter 315 helps attach shaft 3012 to the housing 3020. The liner or washer 3325 is made from a copper material which may ultimately connect to the steering cable 3902 (which acts as a return path) as explained in more detail below.

The tube 3310 includes passageways 3311a-3311d defined therein to orient the cables 3901-3904, respectively, for reception into the flexible joints 3012a and 3012b for ultimate connection to the end effector support 3400 as described above. A central guide tube 3305 is utilized to orient the drive rod 3032 and the knife rod 3504 through the shaft for ultimate connection to jaw member 3110 and knife assembly 3500 as well as drive cable 3810. The central guide tube 3305 is dimensioned for reception within tube 3310 as shown in FIG. 25. One or more steering cables, e.g., 3902, includes a distal portion 3902b that electrically connects to the end effector support 3400 which, in turn, connects to jaw member 3120 thereby providing a return path (i.e., ground path) through the tissue for electrosurgical energy from jaw member 3110 (See FIGS. 30 and 49). The proximal end of the steering cable 3902 may, in turn, electrically interface with the PC board 3804 through cable "R" (See FIG. 34).

The central extrusion or guide tube 3305 is made from a highly flexible and lubricious material and performs several important functions: tube 3305 guides the drive rod 3032, the knife rod 3504 and the electrical lead 3810 from the guide adapter 3315, shaft 3012 and flexible shaft 3012b' to the end effector support 3400 and knife assembly 3500; the tube 3305 provides electrical insulation between component parts; the tube 3305 keeps the lead 3810 and rods 3032 and 3504 separated during relative movement thereof; the tube 3305 minimizes friction and clamping force loss; and tune 3305 keeps the lead 3810 and rods 3032 and 3504 close to the central longitudinal axis to minimize stretching during articulation. The tube 3305 (and internal lumens) may be made from or include materials like polytetrafluoroethene (PTFE), graphite or other lubricating agents to minimize friction and other common losses associated with relative movement of component parts. Alternatively, a coaxial structure (not shown) may be utilized to guide the drive rod 3032 and knife rod 3504.

One or more distal guide plates 3430 and an adapter 3435 may also be utilized to further align the drive rod 3032 and knife rod 3504 and facilitate actuation of the jaw members 3110 and 3120 (See FIG. 25). More particularly and as mentioned above, sleeve 3130 engages flange 3137 of jaw member 3110 such that axial movement of the sleeve 3130 forces jaw member 3110 to rotate around pivot pin 3103 and clamp tissue. Sleeve 3130 connects to adapter 3435 which secures drive rod 3032 therein via a wire crimp 3440. The drive rod 3032 has a flat 332a at a distal end thereof to reinforce attachment to crimp 3440 (See FIGS. 31 and 50). By actuating handle 3040, the drive rod 3032 retracts sleeve 3130 to close jaw member 3110 about tissue.

FIG. 25 also shows the knife assembly 3500 that supports and allows facile reciprocation of the knife blade 3510 through tissue. More particularly, the knife assembly 3500 is configured to operably couple to the trigger assembly 3070 as described above such that actuation of the trigger 3072 translates the knife blade 3510 through tissue held between the jaw members 3110 and 3120. The knife blade 3510 is supported atop a knife support 3505 The knife rod 3504 feeds through adapter 3435 and operably engages a butt end 3505a of the knife support 3505. By squeezing trigger 3072, the knife rod 3504 is forced distally into the butt end 3505a which, in turn, forces the knife 3510 through tissue held between the jaw members 3110 and 3120. The knife rod 3504 may be made from steel or other hardened substances to enhance the rigidity of the rod along the length thereof.

Once a proper tissue seal is formed, the tissue may be severed along the tissue seal. Again, one or more safety features may be employed to assure that a proper seal has been formed prior to severing tissue. For example, the generator may include a safety lockout which electrically prevents or electro-mechanically prevents actuation of the knife 3510 unless a proper and effective seal has been formed.

It is envisioned that knife blade 3510 may also be coupled to the same or an alternative electrosurgical energy source to facilitate separation of the tissue along the tissue seal. Moreover, it is envisioned that the angle of the knife blade tip may be dimensioned to provide more or less aggressive cutting angles depending upon a particular purpose. For example, the knife blade 3510 may be positioned at an angle which reduces "tissue wisps" associated with cutting. More over, the knife blade 3510 may be designed having different blade geometries such as serrated, notched, perforated, hollow, concave, convex etc. depending upon a particular purpose or to achieve a particular result. It is envisioned that the knife 3510 generally cuts in a progressive, uni-directional fashion (i.e., distally).

Various handles and/or handle assemblies may be operatively connected or otherwise associated with end effector assembly 3100 in order to effect operation and movement of the various components thereof, i.e., drive cable 3032 and/or articulation cables 3901-3904. Exemplary handles and/or handle assemblies for use with end effector 3100 are disclosed in U.S. Provisional Application Ser. No. 60/849,562 filed on Oct. 5, 2006 entitled "PROGRAMMABLE MECHANISM FOR MULTIPLE FUNCTION FROM A SINGLE SHAFT"; and U.S. Provisional Application Ser. No. 60/849,560 filed on Oct. 5, 2006 entitled "FLEXIBLE ARTICULATED ENDOSCOPIC INSTRUMENT"; the entire disclosure of each being incorporated by reference hereinabove.

From the foregoing and with reference to the various figure drawings, those skilled in the art will appreciate that certain modifications can also be made to the present disclosure without departing from the scope of the same. For example, it is contemplated that the forceps 3010 (and/or the electrosurgical generator used in connection with the forceps 3010) may include a sensor or feedback mechanism (not shown) which automatically selects the appropriate amount of electrosurgical energy to effectively seal the particularly-sized tissue grasped between the jaw members 3110 and 3120. The sensor or feedback mechanism may also measure the impedance across the tissue during sealing and provide an indicator (visual and/or audible) that an effective seal has been created between the jaw members 3110 and 3120. Examples of such sensor systems are described in commonly-owned U.S. patent application Ser. No. 10/427,832 entitled "METHOD AND SYSTEM FOR CONTROLLING OUTPUT OF RF MEDICAL GENERATOR" filed on May 1, 2003 the entire contents of which are hereby incorporated by reference herein.

As mentioned above, at least one jaw member, e.g., 3120, may include a stop member 3150 which limits the movement of the two opposing jaw members 3110 and 3120 relative to one another. In one embodiment, the stop member 3150 extends from the sealing surface 3122 a predetermined distance according to the specific material properties (e.g., compressive strength, thermal expansion, etc.) to yield a consistent and accurate gap distance "G" during sealing. It is envisioned for the gap distance between opposing sealing surfaces 3112 and 3122 during sealing ranges from about 0.001 inches to about 0.006 inches and, more preferably, between about 0.002 and about 0.003 inches. The non-conductive stop members 150 may be molded onto the jaw members 3110 and 3120 (e.g., overmolding, injection molding, etc.), stamped onto the jaw members 3110 and 3120 or deposited (e.g., deposition) onto the jaw members 3110 and 3120. For example, one technique involves thermally spraying a ceramic material onto the surface of the jaw member 3110 and 3120 to form the stop members 3150. Several thermal spraying techniques are contemplated which involve depositing a broad range of heat resistant and insulative materials on various surfaces to create stop members 3150 for controlling the gap distance between electrically conductive surfaces 3112 and 3122.

Hand switch 3800 may include an ergonomically dimensioned toggle plate (not shown) that may conform to the outer shape of housing 3020 (once assembled). It is envisioned that dimensioning the plate in this fashion permits the user to selectively activate the forceps 3010 in a variety of different orientations, i.e., multi-oriented activation. It is also envisioned that a safety switch or circuit (not shown) may be employed such that the switch 3800 cannot fire unless the jaw members 3110 and 3120 are closed and/or unless the jaw members 3110 and 3120 have tissue held therebetween.

In the latter instance, a sensor (not shown) may be employed to determine if tissue is held therebetween. In addition, other sensor mechanisms may be employed which determine pre-surgical, concurrent surgical (i.e., during surgery) and/or post surgical conditions. The sensor mechanisms may also be utilized with a closed-loop feedback system coupled to the electrosurgical generator to regulate the electrosurgical energy based upon one or more pre-surgical, concurrent surgical or post surgical conditions. Above-mentioned U.S. patent application Ser. No. 10/427,832 describes one such feedback system, the entire contents of which being incorporated by reference hereinabove.

As can be appreciated, locating the switch 3800 on the forceps 3010 has many advantages. For example, the switch 3800 reduces the amount of electrical cable in the operating room and eliminates the possibility of activating the wrong instrument during a surgical procedure due to "line-of-sight" activation. Moreover, it is envisioned that the switch 3800 may be decommissioned during activation of the knife 3185. Decommissioning the switch 3800 when the trigger 3072 is actuated eliminates unintentionally activating the forceps 3010 during the cutting process. It is also envisioned that the switch 3800 may be disposed on another part of the forceps 3010, e.g., the movable handle 3040, fixed handle 3050, a side of the housing 3020, etc.

Another envisioned safety mechanism would be to route cable lead 3810 to energize the one jaw member, e.g., jaw member 3110, and the other electrical potential may be conducted through drive sleeve 3130 and transferred to the other jaw member 3120 to establish electrical continuity only upon retraction of the drive sleeve 3130. It is envisioned that this particular envisioned embodiment will provide at least one additional safety feature, i.e., electrical continuity to the jaw members 3110 and 3120 is made only when the jaw members 3110 and 3120 are closed. The drive rod 3032 may also be energized to the second electrical potential and include a similar-type safety mechanism.

In one embodiment, two isolated electrical leads may supply electrical energy to respective jaw members 3110 and 3120. In this instance it may be desirable to provide additional channels within the shaft 3012 and additional channels 3850 within end effector support 3400 which guide the electrical leads from the housing 3020 to the individual jaw members 3110 and 3120. One or more wire crimps or the like may be utilized to hold the electrical leads in place. Alternatively, cables 3901-3904 may be utilized to both articulate the end effector assembly 3100 and to supply electrical energy to the jaw members 3110 and 3120.

In one embodiment, the electrically conductive sealing surfaces 3112 and 3122 of the jaw members 3110 and 3120, respectively, are relatively flat to avoid current concentrations at sharp edges and to avoid arcing between high points. In addition and due to the reaction force of the tissue when engaged, jaw members 3110 and 3120 can be manufactured to resist bending. For example, the jaw members 3110 and 3120 may be tapered along the width thereof which resists bending due to the reaction force of the tissue.

It is envisioned that the outer surface of the end effector assembly 3100 may include a nickel-based material, coating, stamping, metal injection molding which is designed to reduce adhesion between the jaw members 3110 and 3120 with the surrounding tissue during activation and sealing. Moreover, it is also contemplated that the conductive surfaces 3112 and 3122 of the jaw members 3110 and 3120 may be manufactured from one (or a combination of one or more) of the following materials: nickel-chrome, chromium nitride, MedCoat 2000 manufactured by The Electrolizing Corporation of OHIO, inconel 600 and tin-nickel. The tissue conductive surfaces 3112 and 3122 may also be coated with one or more of the above materials to achieve the same result, i.e., a "non-stick surface". As can be appreciated, reducing the amount that the tissue "sticks" during sealing improves the overall efficacy of the instrument.

One particular class of materials disclosed herein has demonstrated superior non-stick properties and, in some instances, superior seal quality. For example, nitride coatings which include, but are not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation. One particularly useful non-stick material in this class is Inconel 600. Bipolar instrumentation having sealing surfaces 3112 and 122 made from or coated with Ni200, Ni201 (~100% Ni) also showed improved non-stick performance over typical bipolar stainless steel electrodes.

Forceps 3010 may be designed such that it is fully or partially disposable depending upon a particular purpose or to achieve a particular result. For example, end effector assembly 100 may be selectively and releasably engageable with the distal end 3016 of the shaft 3012 and/or the proximal end 3014 of shaft 3012 may be selectively and releasably engageable with the housing 3020 and the handle assembly 3030. In either of these two instances, the forceps 3010 would be considered "partially disposable" or "reposable", i.e., a new or different end effector assembly 3100 (or end effector assembly 3100 and shaft 3012) selectively replaces the old end effector assembly 3100 as needed. As can be appreciated, the presently disclosed electrical connections would have to be altered to modify the instrument to a reposable forceps. Moreover, various composite materials may be employed for parts of the end effector assembly 3100 to lessen manufacturing costs.

In yet another embodiment, the entire shaft 3012 (or portions thereof) may be flexible (or substantially flexible) along a length thereof to facilitate negotiation through a tortuous path. The number and size of the flexible joints 3012a and 3012b and end effector assembly 3100 may be altered to meet a particular surgical purpose or to enhance effectiveness of the forceps 3010 for a particular surgical solution.

Although various cables, rods and shafts are employed for the various components herein, it is possible to substitute any one or all of these components with variations thereof depending upon a particular purpose.

In addition, it is also contemplated that one or more electrical motors may be utilized either automatically or manually to articulate the cables 3901-3904, advance the knife rod 3504 or retract the drive rod 3032.

The forceps 3010 is suited for use by either a left or right-handed user and the articulation wheels 3081 and 3091 are particularly situated atop the housing to facilitate usage thereof by either handed user.

Figure 57:
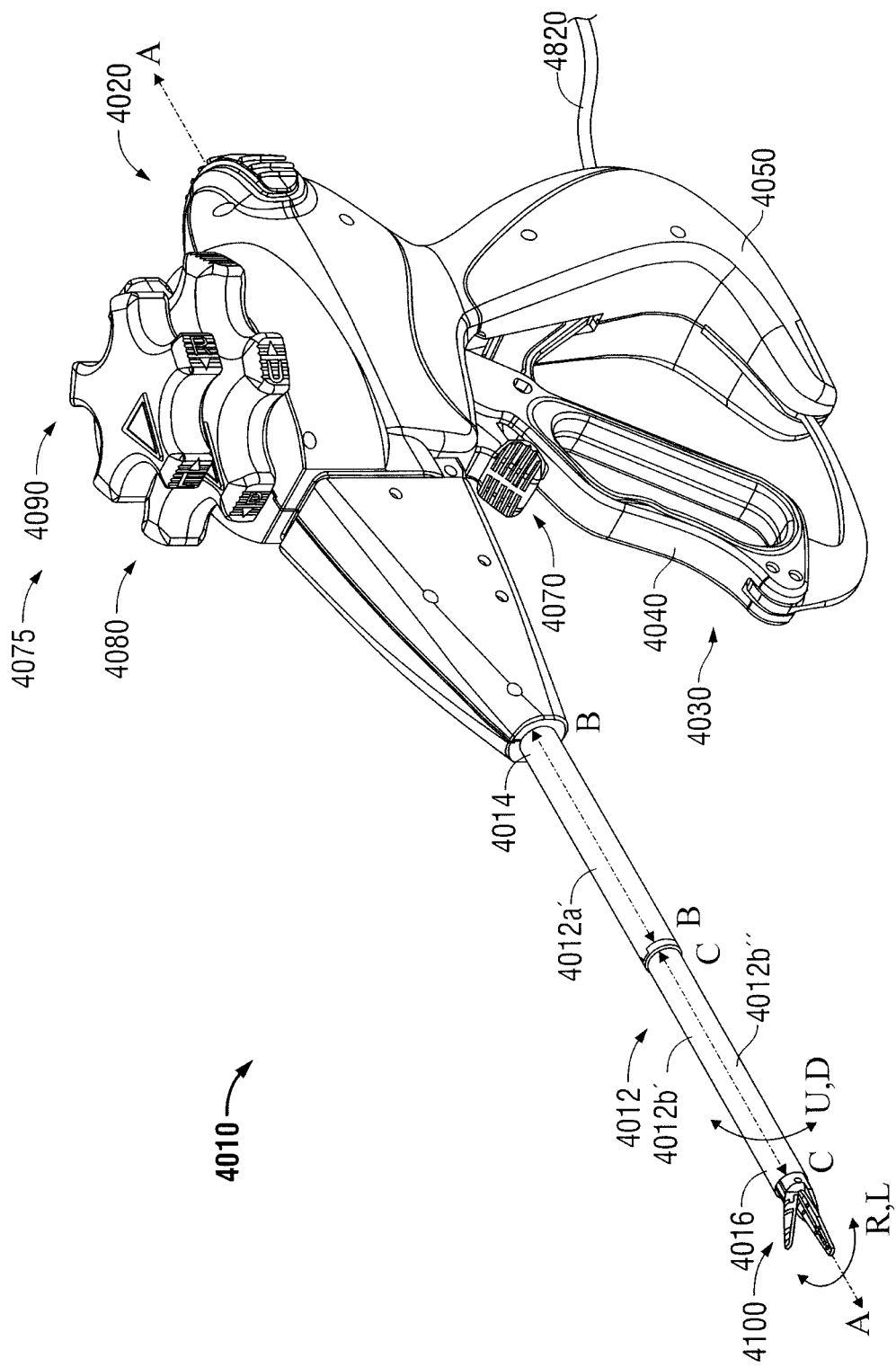
FIG. 57 is a perspective view of an endoscopic forceps depicting a housing, an elongated shaft, articulation assembly and an end effector assembly according to another embodiment of the present disclosure.

Referring now to FIG. 57, another embodiment of an endoscopic vessel sealing forceps is depicted generally as 4010. In the drawings and in the descriptions relating to this embodiment which follow, the term "proximal," as is traditional, will refer to the end of the forceps 4010 which is closer to the user, while the term "distal" will refer to the end which is farther from the user. The forceps 4010 comprises a housing 4020, an end effector assembly 4100 and an elongated shaft 4012 extending therebetween to define a longitudinal axis A-A. A handle assembly 4030, an articulation assembly 4075 composed of two articulation controls 4080 and 4090 and a trigger assembly 4070 are operable to control the end effector assembly 4100 to effectively grasp, seal and divide tubular vessels and vascular tissue. Although the forceps 4010 is configured for use in connection with bipolar surgical procedures, various aspects of the present disclosure may also be employed for monopolar surgical procedures.

Forceps 4010 includes an electrosurgical cable 4820, which connects the forceps 4010 to a source of electrosurgical energy, e.g., a generator (not shown). It is contemplated that generators such as those sold by Covidien-Energy-based Devices may be used as a source of electrosurgical energy, e.g., LIGASURE™ Vessel Sealing Generator and Force Triad™ Generator. Cable 4820 may be internally divided into numerous leads (not shown), which each transmit electrosurgical energy through respective feed paths through the forceps 4010 for connection to the end effector assembly 4100.

Handle assembly 4030 includes a fixed handle 4050 and a movable handle 4040. The fixed handle 4050 is integrally associated with the housing 4020, and the movable handle 4040 is movable relative to fixed handle 4050 to induce relative movement between a pair of jaw members 4110, 4120 of the end effector assembly 4100. The movable handle 4040 is operatively coupled to the end effector assembly 4100 via a drive rod 4032 (see FIG. 58), which extends through the elongated shaft 4012, and reciprocates to induce movement in the jaw members 4110, 4120. Drive rod 4032 may be made of flexible material, such as steel wire. The movable handle 4040 may be approximated with fixed handle 4050 to move the jaw members 4110 and 4120 from an open position wherein the jaw members 4110 and 4120 are disposed in spaced relation relative to one another, to a clamping or closed position wherein the jaw members 4110 and 4120 cooperate to grasp tissue therebetween. Electrosurgical energy may be transmitted through tissue grasped between jaw members 4110, 4120 to effect a tissue seal.

Trigger assembly 4070 is operable to advance a blade 4510 (FIG. 58) through a knife channel, e.g., 4115b defined in the jaw members 4110, 4120 to transect sealed tissue. The trigger assembly 4070 is operatively coupled to the blade 4510 via a knife rod 4504 (FIG. 58), which extends through the elongated shaft 4012. Various aspects of the end effector assembly 4100, the housing 4020, handle assembly 4030, the trigger assembly 4070 and the operation of these mechanisms to electrosurgically treat tissue are discussed in greater detail in commonly owned U.S. Provisional Application No. 61/157, 722, the entire content of which is incorporated by reference herein.

Elongated shaft 4012 defines a distal end 4016 dimensioned to mechanically engage the end effector assembly 4100 and a proximal end 4014, which mechanically engages the housing 4020. The elongated shaft 4012 includes two distinct portions, a proximal portion 4012a' defining a proximal shaft axis B-B and a distal portion 4012b' defining a distal shaft axis C-C.

The proximal portion 4012a' of the shaft 4012 may exhibit various constructions. For example, the proximal portion 4012a' may be formed from a substantially rigid tube, from flexible tubing (e.g., plastic), or the proximal portion 4012a' may be formed as a composite of a flexible tube and a rigidizing element, such as a tube of braided steel, to provide axial (e.g., compressional) and rotational strength. In other embodiments, the proximal portion 4012a' may be constructed from a plastically deformable material. In some embodiments the proximal portion 4012a' exhibits a flexural rigidity that is sufficiently low to permit a surgeon to preshape or reshape the proximal portion 4012a' prior to or during a surgical procedure to accommodate the contours and characteristics of the surgical site. Once shaped, the proximal end portion 12a' may define a non-aligned configuration wherein the proximal shaft axis B-B is substantially out of alignment with the longitudinal axis A-A. The proximal portion 4012a' may also exhibit an axial rigidity that is sufficient to maintain the shape and orientation of the non-aligned configuration during normal surgical use of the instrument 10. In the embodiment described below with reference to FIGS. 64, 66, 68 and 70, the proximal portion 4012a' is maintained in the configuration aligned with the longitudinal axis A-A.

Figure 58:
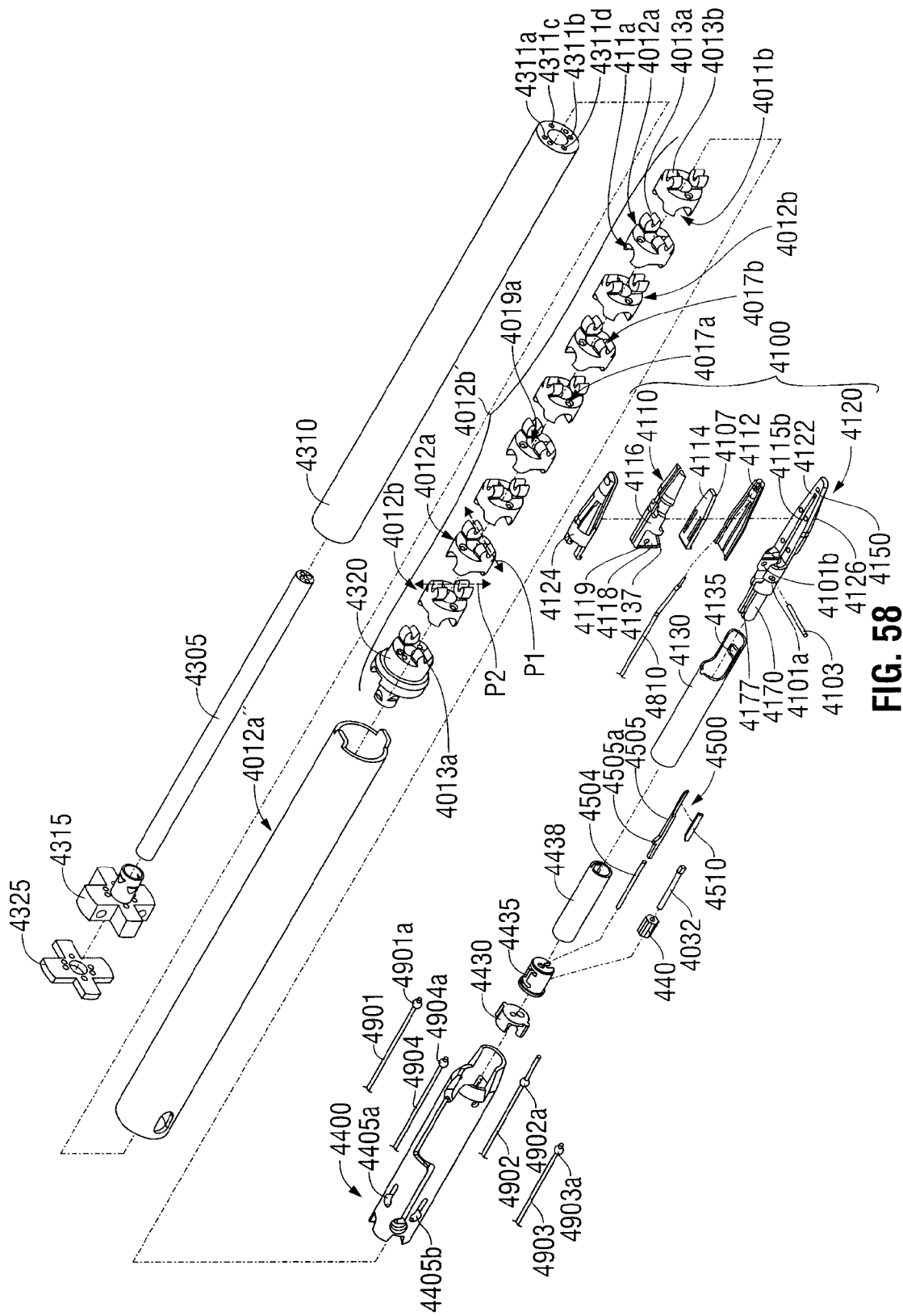
FIG. 58 is an enlarged, exploded perspective view of the end effector and elongated shaft of FIG. 57 depicting a plurality of links forming an articulating portion of the elongated shaft, and a flexible tube forming a flexible portion of the elongated shaft.

The distal portion 4012b' of shaft 4012 includes an exterior casing or insulating material 4012b" disposed over a plurality of joints or links 4012a, 4012b (see FIG. 58). The links 4012a and 4012b are configured to pivot relative to one another to permit the distal portion 4012b' of the shaft 4012 to articulate relative to the proximal shaft axis B-B. In one embodiment, the links 4012a and 4012b are nestingly engaged with one another to permit pivotal motion of the distal portion 4012b' in two orthogonal in response to movement of articulation controls 4080 and 4090.

Articulation assembly 4075 sits atop housing 4020 and is operable via articulation controls 4080 and 4090 to move the end effector assembly 4100 (and the articulating distal portion 4012b' of the shaft 4012) in the direction of arrows "U, D" and "R, L" relative to axis proximal shaft axis B-B as explained in more detail below. Controls 4080 and 4090 may be provided in alternative arrangements such as disposed on the side of housing 4020. Also, controls 4080 and 4090 may be replaced by other mechanisms to articulate the end effector 4100 such as levers, trackballs, joysticks, or the like.

Referring now to FIG. 58, the articulating distal portion 4012b' of shaft 4012 includes a plurality of links 4012a and 4012b. Each link 4012a engages a neighboring link 4012b such that the distal portion 4012b' of the shaft 4012 may articulate the end effector assembly 4100. Links 4012a are similar in construction to links 4012b in that each link 4012a, 4012b exhibits a pair of distal knuckles 4013a, 4013b and pair of opposing proximal clevises 11a, 11b formed therewith. Links 4012a, however, are oriented with a ninety degree) (90°) radial offset with respect to the neighboring link 4012b. Such an alternating orientation of the links 4012a, 4012b facilitates articulation of the end effector 4100 in orthogonal planes. The distal knuckles 4013a of links 4012a define a horizontal pivot axis P1. Thus a distal knuckle 4013a operatively engages a corresponding clevis 4011b of a neighboring link 4012b to facilitate articulation of the end effector 4100 in the direction of arrows "U, D" (FIG. 57). Similarly, the distal knuckles 4013b of links 4012b define a vertical pivot axis P2 such that a distal knuckle 4013b operatively engages a corresponding clevis 4011a of a neighboring link 4012a to facilitate articulation of the end effector 4100 in the direction of arrows "R, L."

Each link 4012a and 4012b includes a central lumen 4019a extending longitudinally therethrough. The central lumen 4019a permits passage of various actuators, e.g., drive rod 4032 and knife rod 4504, and other components through the elongated shaft 4012. Links 4012a, 4012b also define two pairs of opposed lumens 4017a and 4017b formed radially outward from the central lumen 4019a. Each of the lumens 4017a and 4017b on a link 4012a is radially spaced at a 90° from the neighboring lumen 4017a, 4017b such that each lumen 4017a aligns with a lumen 4017b of a neighboring link 4012b. The lumens 4017a and 4017b cooperate to define a longitudinal cavity to permit passage of four steering cables 4901, 4902, 4903 and 4904 through the articulating portion 4012b' of the elongated shaft 4012. A differential tension may be imparted to the four steering cables 4901-4904 to adjust the orientation of the articulating distal portion 4012b' of shaft 4012 as described below with reference to FIGS. 66, 68 and 70.

A link support 4320 includes a pair of distal knuckles 4013a oriented similarly to a link 4012a to interface with a trailing link 4012b. A proximal end of the link support 4320 is fixedly mounted to an outer casing 4012a", which extends over the proximal portion 4012a' of the elongated shaft 4012. The outer casing 4012a" is generally flexible to permit the proximal portion 4012a' to flex and bend freely. An end effector support 4400 includes a pair of clevises 4011b on a proximal end oriented similarly to a link 4012a to receive the distal knuckles 4013b of a leading link 4012b.

The four steering cables 4901-4904 may be substantially elastic and slideably extend through lumens pairs 4017a, and 4017b defined in the links 4012a and 4012b. A distal end of the each of the steering cables 4901-4904 is coupled to the end effector support 4400. More particularly, each steering cable 4901-4904 includes a ball-like mechanical interface at the distal end, namely, interfaces 4901a-4904a. Each interface 4901a-4904a is configured to securely mate within a corresponding recess defined in the end effector support 4400. Interface 4904a engages recess 4405a, interface 4903a engages recess 4405b, and interfaces 4901a and 4902a engage similar recess on the end effector support 4400.

Proximal ends of the steering cables 4901-4904 are operatively coupled to the articulation controls 4080, 4090 as described below with reference to FIGS. 60 and 61. The steering cables 4901-4904 extend through the shaft 4012 through a series of passageways defined therein. More particularly, a cross-shaped cable guide adapter 4315 and guide adapter liner or washer 4325 include bores defined therethrough to initially orient the cables 4901-4904 at 90° degree angles relative to one another for passage into an outer tube 4310. The adapter 4315 also facilitates attachment of the shaft 4012 to the housing 4020. The tube 4310 includes passageways 4311a-4311d defined therein to orient the cables 4901-4904, respectively, for reception into the lumens 4017a, 4017b of links 4012a and 4012b for ultimate connection to the end effector support 4400 as described above.

A central guide tube 4305 is provided to orient the drive rod 4032 and the knife rod 4504 through the shaft 4012 for ultimate connection to jaw member 4110 and a knife assembly 4500. The central guide tube 4305 also guides an electrical lead 4810 for providing electrosurgical energy to the jaw member 4110. The central guide tube 4305 is dimensioned for reception within outer tube 4310, and may extend distally therefrom into the central lumens 4019a defined in the links 4012a and 4012b. One or more steering cables, e.g., 4902, includes a distal portion 4902b that electrically connects to the end effector support 4400 which, in turn, connects to jaw member 4120. A return path (i.e., ground path) may thus be established through tissue captured between jaw members 4110 and 4120 for electrosurgical energy provided through jaw member 4110.

The central extrusion or guide tube 4305 is constructed from a highly flexible and lubricious material and performs several important functions: tube 4305 guides the drive rod 4032, the knife rod 4504 and the electrical lead 4810 from the guide adapter 4315, shaft 4012 and flexible shaft 4012b' to the end effector support 4400 and knife assembly 4500; the tube 4305 provides electrical insulation between component parts; the tube 4305 keeps the lead 4810 and rods 4032 and 4504 separated during relative movement thereof; the tube 4305 minimizes friction and clamping force loss; and tube 4305 keeps the lead 4810 and rods 4032 and 4504 close to the central longitudinal axis to minimize stretching during articulation. The tube 4305 (and internal lumens) may be made from or include materials like polytetrafluoroethene (PTFE), graphite or other lubricating agents to minimize friction and other common losses associated with relative movement of component parts. Alternatively, a coaxial structure (not shown) may be utilized to guide the drive rod 4032 and knife rod 4504.

One or more distal guide plates 430 and an adapter 435 may also be utilized to further align the drive rod 4032 and knife rod 4504 and facilitate actuation of the jaw members 4110 and 4120. More particularly, alignment of the drive rod 4032 facilitates opening and closing the jaw members 4110, 4120. A sleeve 4130 includes an aperture 4135 to engage a flange 4137 of jaw member 4110 such that axial movement of the sleeve 4130 forces jaw member 4110 to rotate around pivot pin 4103 and clamp tissue. Sleeve 4130 connects to adapter 4435 which secures drive rod 4032 therein via a wire crimp 4440. The drive rod 4032 has a flat 4032a at a distal end thereof to reinforce attachment to crimp 4440. By actuating movable handle 4040 (FIG. 57), the drive rod 4032 retracts sleeve 4130 to close jaw member 4110 about tissue. Pulling the sleeve 4130 proximally closes the jaw members 4110 and 4120 about tissue grasped therebetween and pushing the sleeve 130 distally opens the jaw members 4110 and 4120 for grasping purposes. The end effector assembly 4100 is designed as a unilateral assembly, i.e., jaw member 4120 is fixed relative to the shaft 4012 and jaw member 4110 pivots about a pivot pin 103 to grasp tissue.

Also, alignment of knife rod 4504 facilitates longitudinal movement of blade 4510. Knife channel 4115b runs through the center of jaw member 4120 and a similar knife channel (not shown) extends through the jaw member 4110 such that the blade 4510 can cut the tissue grasped between the jaw members 4110 and 4120 when the jaw members 4110 and 4120 are in the closed position.

Jaw member 4110 also includes a jaw housing 4116 which has an insulative substrate or insulator 4114 and an electrically conducive surface 4112. Housing 4116 and insulator 4114 are dimensioned to securely engage the electrically conductive sealing surface 4112. This may be accomplished by stamping, by overmolding, by overmolding a stamped electrically conductive sealing plate and/or by overmolding a metal injection molded seal plate. For example, the electrically conductive sealing plate 4112 may include a series of upwardly extending flanges that are designed to matingly engage the insulator 4114. The insulator 4114 includes a shoe-like interface 4107 disposed at a distal end thereof which is dimensioned to engage the outer periphery of the housing 4116 in a slip-fit manner. The shoe-like interface 4107 may also be overmolded about the outer periphery of the jaw 4110 during a manufacturing step. It is envisioned that lead 4810 terminates within the shoe-like interface 4107 at the point where lead 4810 electrically connects to the seal plate 4112 (not shown). The movable jaw member 4110 also includes a wire channel (not shown) that is designed to guide electrical lead 4810 into electrical continuity with sealing plate 4112.

All of these manufacturing techniques produce jaw member 4110 having an electrically conductive surface 4112 which is substantially surrounded by an insulating substrate 4114 and housing 4116. The insulator 4114, electrically conductive sealing surface 4112 and the outer, jaw housing 4116 are dimensioned to limit and/or reduce many of the known undesirable effects related to tissue sealing, e.g., flashover, thermal spread and stray current dissipation. Alternatively, it is also envisioned that jaw members 4110 and 4120 may be manufactured from a ceramic-like material and the electrically conductive surface(s) 4112 are coated onto the ceramic-like jaw members 4110 and 4120.

Jaw member 4110 also includes a pivot flange 4118 which includes the protrusion 4137. Protrusion 4137 extends from pivot flange 4118 and includes an arcuately-shaped inner surface dimensioned to matingly engage the aperture 4135 of sleeve 4130 upon retraction thereof. Pivot flange 4118 also includes a pin slot 4119 that is dimensioned to engage pivot pin 4103 to allow jaw member 4110 to rotate relative to jaw member 4120 upon retraction of the reciprocating sleeve 4130. Pivot pin 4103 also mounts to the stationary jaw member 4120 through a pair of apertures 4101a and 4101b disposed within a proximal portion of the jaw member 4120.

Jaw member 4120 includes similar elements to jaw member 4110 such as jaw housing 4126 and an electrically conductive sealing surface 4122. Likewise, the electrically conductive surface 4122 and the insulative housing 4126, when assembled, define the longitudinally-oriented channel 4115a for reciprocation of the knife blade 4510. As mentioned above, when the jaw members 4110 and 4120 are closed about tissue, the knife channel 4115*b* permits longitudinal extension of the blade 4510 to sever tissue along the tissue seal.

Jaw member 4120 includes a series of stop members 4150 disposed on the inner facing surfaces of the electrically conductive sealing surface 4122 to facilitate gripping and manipulation of tissue and to define a gap "G" of about 0.001 inches to about 0.006 inches between opposing jaw members 4110 and 4120 during sealing and cutting of tissue. It is envisioned that the series of stop members 4150 may be employed on one or both jaw members 4110 and 4120 depending upon a particular purpose or to achieve a desired result. A detailed discussion of these and other envisioned stop members 4150 as well as various manufacturing and assembling processes for attaching and/or affixing the stop members 4150 to the electrically conductive sealing surfaces 112, 122 are described in U.S. Pat. No. 7,473,253 (Ser. No. 10/471,818) entitled "VESSEL SEALER AND DIVIDER WITH NON-CONDUCTIVE STOP MEMBERS" by Dycus et al. which is hereby incorporated by reference in its entirety herein.

Jaw member 4120 is designed to be fixed to the end of a tube 4438, which is part of the distal articulating portion 4012*b*' of the shaft 4012. Thus, articulation of the distal portion 4012*b*' of the shaft 4012 will articulate the end effector assembly 4100. Jaw member 4120 includes a rear C-shaped cuff 4170 having a slot 4177 defined therein that is dimensioned to receive a slide pin 4171 disposed on an inner periphery of tube 4438. More particularly, slide pin 4171 extends substantially the length tube 4438 to slide into engagement (e.g., friction-fit, glued, welded, etc) within slot 4177. C-shaped cuff 4170 inwardly compresses to assure friction-fit engagement when received within tube 4438. Tube 4438 also includes an inner cavity defined therethrough that reciprocates the knife assembly 4500 upon distal activation thereof. The knife blade 4510 is supported atop a knife support 4505. The knife rod 4504 feeds through adapter 4435 and operably engages a butt end 4505*a* of the knife support 4505. By actuating trigger assembly 4070, the knife rod 4504 is forced distally into the butt end 4505*a* which, in turn, forces the blade 4510 through tissue held between the jaw members 4110 and 4120. The knife rod 4504 may be constructed from steel wire to enhance its axial stiffness of the rod along the length thereof, while simultaneously being flexible along its length.

As mentioned above, the jaw members 4110 and 4120 may be opened, closed and articulated to manipulate tissue until sealing is desired. This enables the user to position and re-position the forceps 4010 (FIG. 57) prior to activation and sealing. The unique feed path of the electrical lead 4810 through the housing, along shaft 4012 and, ultimately, to the jaw member 4110 enables the user to articulate the end effector assembly 4100 in multiple directions without tangling or causing undue strain on electrical lead 4810.

Figure 59:
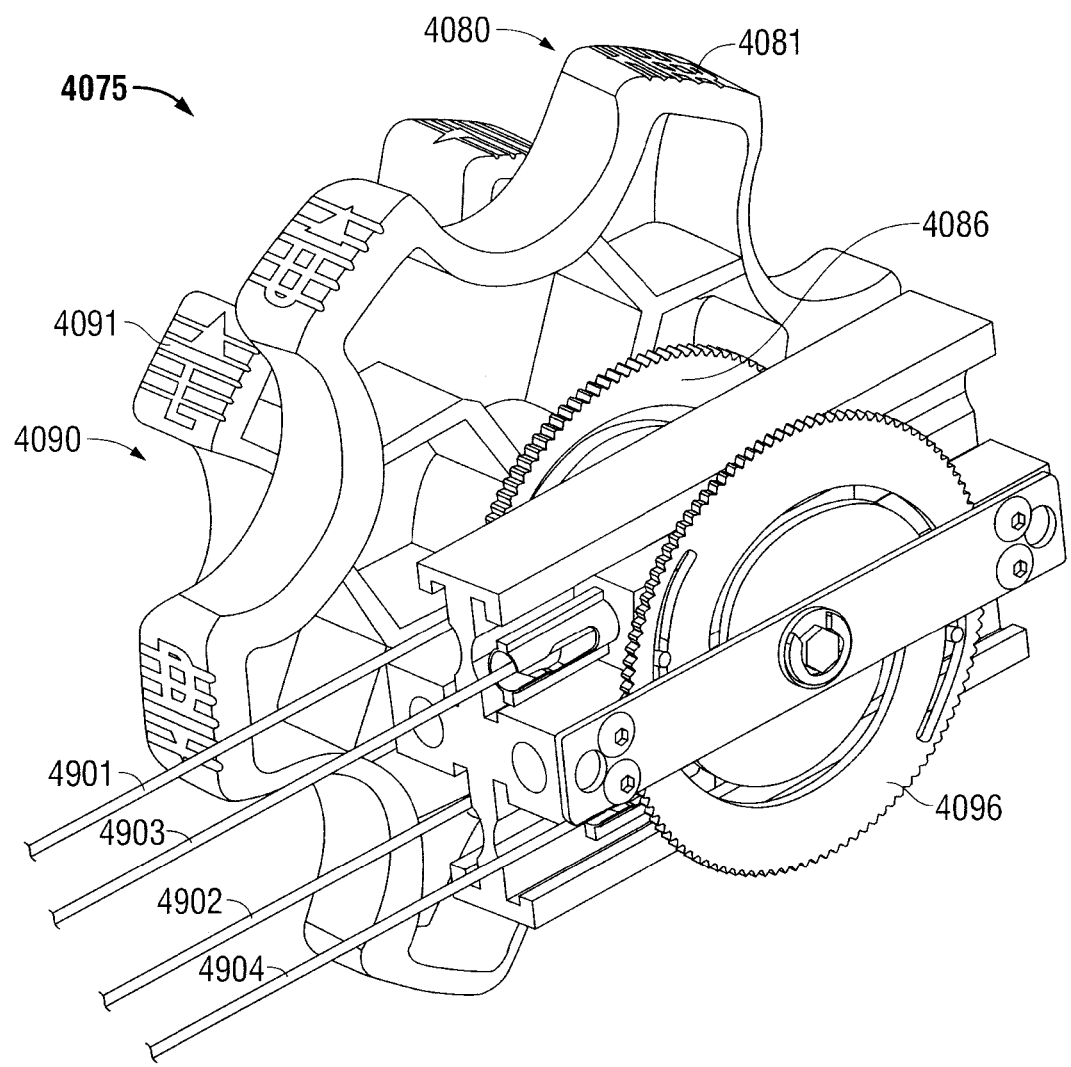
FIG. 59 is an enlarged, perspective view of an underside of the articulation assembly of FIG. 57 depicting a cam wheel for driving a set of sliders.

Referring now to FIG. 59, the articulation assembly 4075 permits selective articulation of the end effector assembly 4100 to facilitate the manipulation and grasping of tissue. More particularly, the two controls 4080 and 4090 include selectively rotatable wheels, 4081 and 4091, respectively, that sit atop the housing 4020 (FIG. 57). Each wheel, e.g., wheel 4081, is independently moveable relative to the other wheel, e.g., 4091, and allows a user to selectively articulate the end effector assembly 4100 in a given plane of articulation relative to the longitudinal axis A-A. For example, rotation of wheel 4091 articulates the end effector assembly 4100 along arrows R, L (or right-to-left articulation, see FIGS. 57 and 68) by rotating cam wheel 4096 to induce a differential tension and a corresponding longitudinal motion in steering cables 4903 and 4904. Similarly, rotation of wheel 4081 articulates the end effector assembly along arrows U, D (or up-and-down articulation, see FIGS. 57 and 70) by rotating cam wheel 4086 to induce a differential tension and a corresponding longitudinal motion in steering cables 4901 and 4902.

Figure 60:
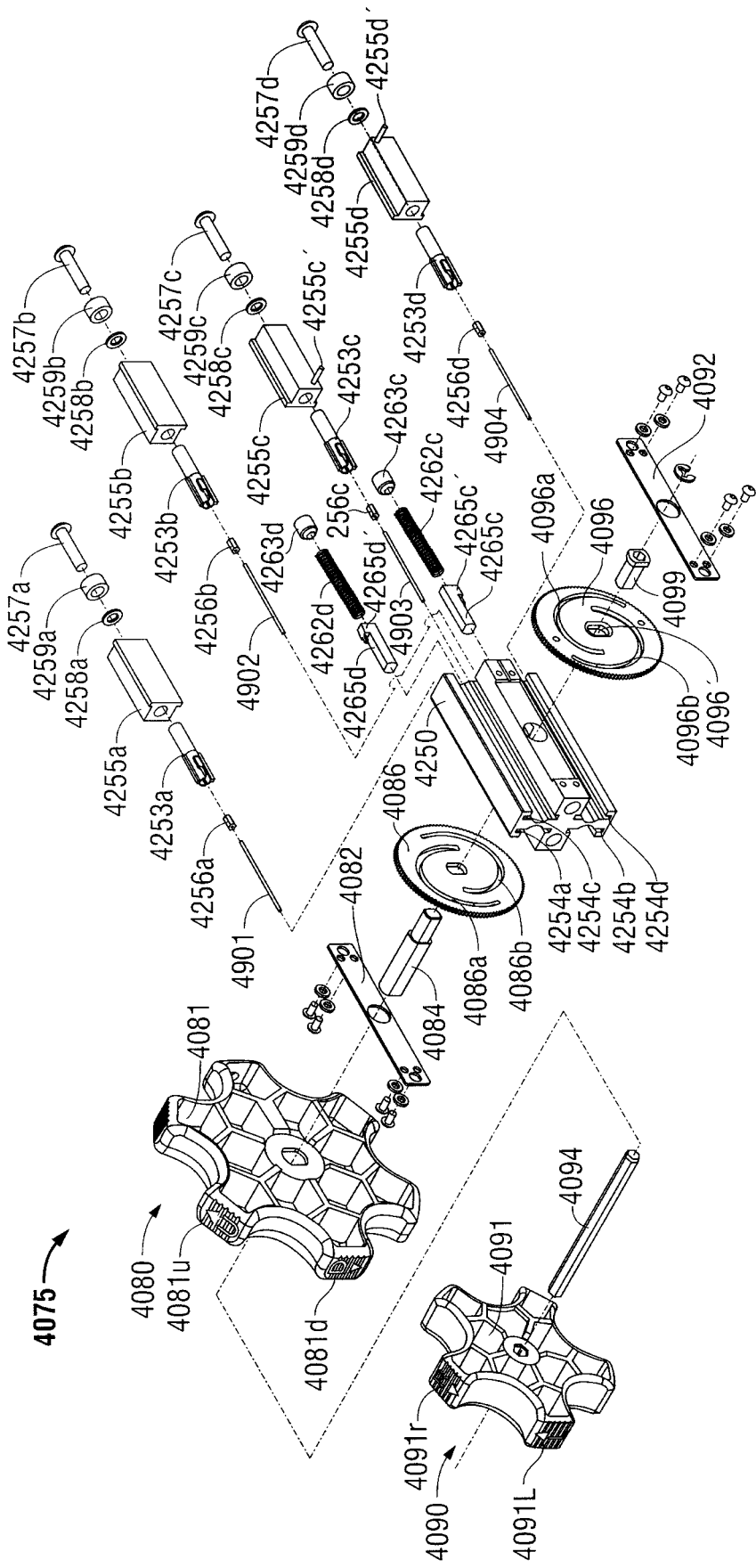
FIG. 60 is an exploded, perspective view of the articulation assembly.

Referring now to FIG. 60, the articulation assembly 4075 includes an articulation block 4250, which mounts longitudinally within the housing 4020 (FIG. 57). Rotatable wheel 4081 is operatively coupled to the articulation block 4250 via an elongated hollow block 4084. The block 4084 is mechanically coupled at one end to the wheel 4081 by a set-screw or a friction-fit, for example, such that rotation of the wheel 4081 rotates the block 4084. An opposite end of the block 4084 interfaces similarly with the cam wheel 4086 such that rotation of the block 4084 effects rotation of the cam wheel 4086 relative to the articulation block 4250. A cover plate 4082 is attached to the articulation block 4250 by bolts or other mechanical connections and prevents the cam wheel 4086 from sliding out of a receiving hole in the articulation block 4250.

Cam wheel 4086, in turn, mounts to the articulation block 4250 such that each of two arcuate cam slots 4086*a* and 4086*b* formed therein couples to a respective slider 4255*a* and 4255*b*. Each slider 4255*a*, 4255*b* includes a pin (not shown) protruding toward the respective cam slot 4086*a* and 4086*b*. The cam slots 4086*a* and 4086*b* are eccentric with respect to the cam wheel 4086, i.e., the cam slots 4086*a* and 4086*b* do not share a center of rotation with the cam wheel 4086. Thus rotation of the cam wheel 4086 induces the sliders 4255*a*, 4255*b* to ride along a respective predefined rail 4254*a* and 4254*b* disposed in the articulation block 4250.

The sliders 4255*a* and 4255*b* each couple to an end of a respective steering cable 4901 and 4902 via a series of crimped sleeves 4256*a*, 4256*b*, coupling shafts 4253*a*, 4253*b*, washers 4258*a*, 4258*b*, elastic compression bushings or springs 4259*a*, 4259*b* and tensioning bolts 4257*a*, 4257*b*. This connection is described in greater detail below with reference to FIG. 61.

Thus, the steering cables 4901 and 4902 are coupled to the wheel 4091 such that rotation of the wheel 4081 in a given direction causes the respective sliders 4255*a* and 4255*b* to slide oppositely relative to one another within rails 4254*a* and 4254*b* to pull or stretch a respective steering cable 4901, 4902. For example, rotation of wheel 4081 in a clockwise direction from the perspective of a user, i.e. in the direction of arrow 4081*d* (DOWN "D"), causes the cam wheel 4086 to rotate clockwise which, in turn, causes the pins protruding from the sliders 4255*a*, 4255*b* to move longitudinally.

As a result thereof, as slider 4255*a* moves distally and slider 4255*b* moves proximally, steering cable 4901 moves distally and steering cable 4902 moves proximally, thus causing end effector assembly 4100 to articulate DOWN "D". When wheel 4081 is rotated counter-clockwise, i.e. in the direction of arrow 4081*u*, (UP "U") the sliders 4255*a* and 4255*b* move in an opposite direction on rails 4254*a* and 4254*b*. The end effector assembly 4100 is affected oppositely, i.e., the end effector assembly 4100 is articulated in an UP "U" direction (See FIG. 70). Rotational movement of wheel 4081 thus moves the end effector assembly 4100 in an UP "U" and DOWN "D" plane relative to the longitudinal axis A-A (See FIG. 57). The cam connection between the sliders 4255*a* and 4255*b* and the cam wheel 4086 offers increased mechanical advantage when a user increases the articulation angle, i.e., the cam connection helps overcome the increasing resistance to articulation as the articulating portion 4012*b*' of shaft 4012 is articulated in a given direction. The cam connection is described in greater detail below with reference to FIGS. 63, 65 and 67.

Rotatable wheel 4091 of articulation control 4090 is coupled to articulation block 4250 in a similar manner. More particularly, wheel 4091 operatively engages one end of a solid spindle 4094 which, in turn, attaches at an opposite end thereof to cam wheel 4096 disposed on an opposite end of the articulation block 4250. Solid spindle 4094 is dimensioned for insertion through hollow block 4084 such that the solid spindle 4094 is rotatable relative to the hollow block 4084. Solid spindle 4094 passes through the hollow block 4084 and engages a locking nut 4099. Locking nut 4099 exhibits an outer profile that permits the locking nut 4099 to seat within a locking recess 4096' engraved within cam wheel 4096. Locking nut 4099 is fixedly coupled to cam wheel 4096 by welding or a similar process such that rotational motion of the solid spindle 4094 is transferred to the cam wheel 4096. Hollow block 4084 exhibits an inner profile such that the solid spindle 4094 has sufficient clearance to rotate therein without causing rotation of the hollow block 4084.

A cover plate 4092 is utilized to secure the cam wheel 4096 to the articulation block 4250. Much like cam wheel 4086, rotation cam wheel 4096 operably couples to a pair of sliders 4255c and 4255d, which are configured to ride in rails 4254c and 4254d defined in the articulation block 4250. More particularly, each cam slot 4096a and 4096b of cam wheel 4096 engages a respective slider 4255c and 4255d. Each slider 4255c, 4255d includes a pin 4255c', 4255d' protruding into the respective cam slot 4096a and 4096b such that rotation of the cam wheel 4096 induces longitudinal motion of the sliders 4255c, 4255d within the respective rails 4254c and 4254d. Thus, rotation of the cam wheel 4096 in a given direction causes the respective sliders 4255c and 4255d to slide oppositely relative to one another within rails 4254c and 4254d. The sliders 4255c and 4255d each couple to an end of a respective steering cable 4903 and 4904 via a series of tensioning bolts 4256c, 4256d, sleeves 4253c, 4253d, washers 4258c, 4258d, elastic compression bushings or springs 4259c, 4259d and tensioning bolts 4257c, 4257d as discussed below with reference to FIG. 61. Thus, the movement of the sliders 4255c and 4255d tends to pull or contract respective steering cables 4903, 4904.

Figure 67:
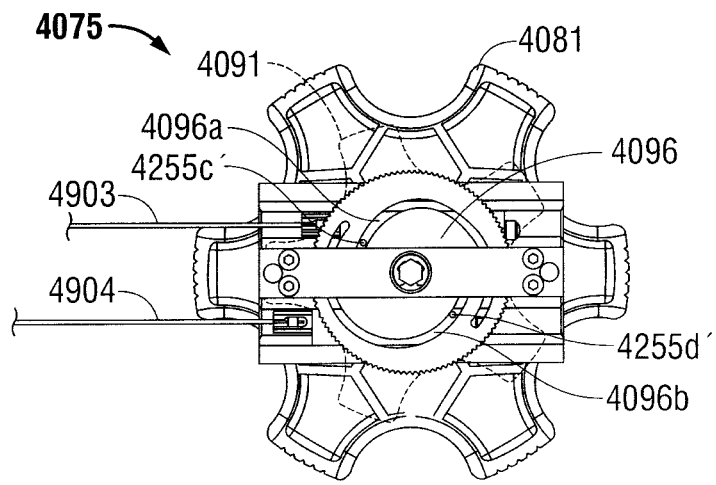
FIG. 67 is a bottom view of the articulation assembly in a configuration corresponding to a LEFT articulated orientation of the articulating portion.

Rotation of wheel 4091 in a clockwise direction from the perspective of a user, i.e., in the direction of arrow 4091R (RIGHT "R"), causes the cam wheel 4096 to rotate clockwise which, in turn, drives the pin 4255c' distally and pin 4255d' proximally (See FIG. 67). As a result thereof, slider 4255c moves distally and slider 4255d moves proximally causing steering cable 4903 to move distally and steering cable 4904 to move proximally thus causing end effector assembly 4100 to articulate to the RIGHT "R" (see FIG. 68). When wheel 4091 is rotated counter-clockwise, i.e. in the direction of arrow 4091L, the sliders 4255c and 4255d move in an opposite direction on rails 4254c and 4254d (see FIG. 69) and end effector assembly 4100 has an opposite effect, i.e., the end effector assembly 4100 is articulated to the LEFT "L" (see FIG. 70). Rotational movement of wheel 4091 moves the end effector assembly 4100 in a RIGHT and LEFT plane relative to the longitudinal axis A-A.

Figure 61:
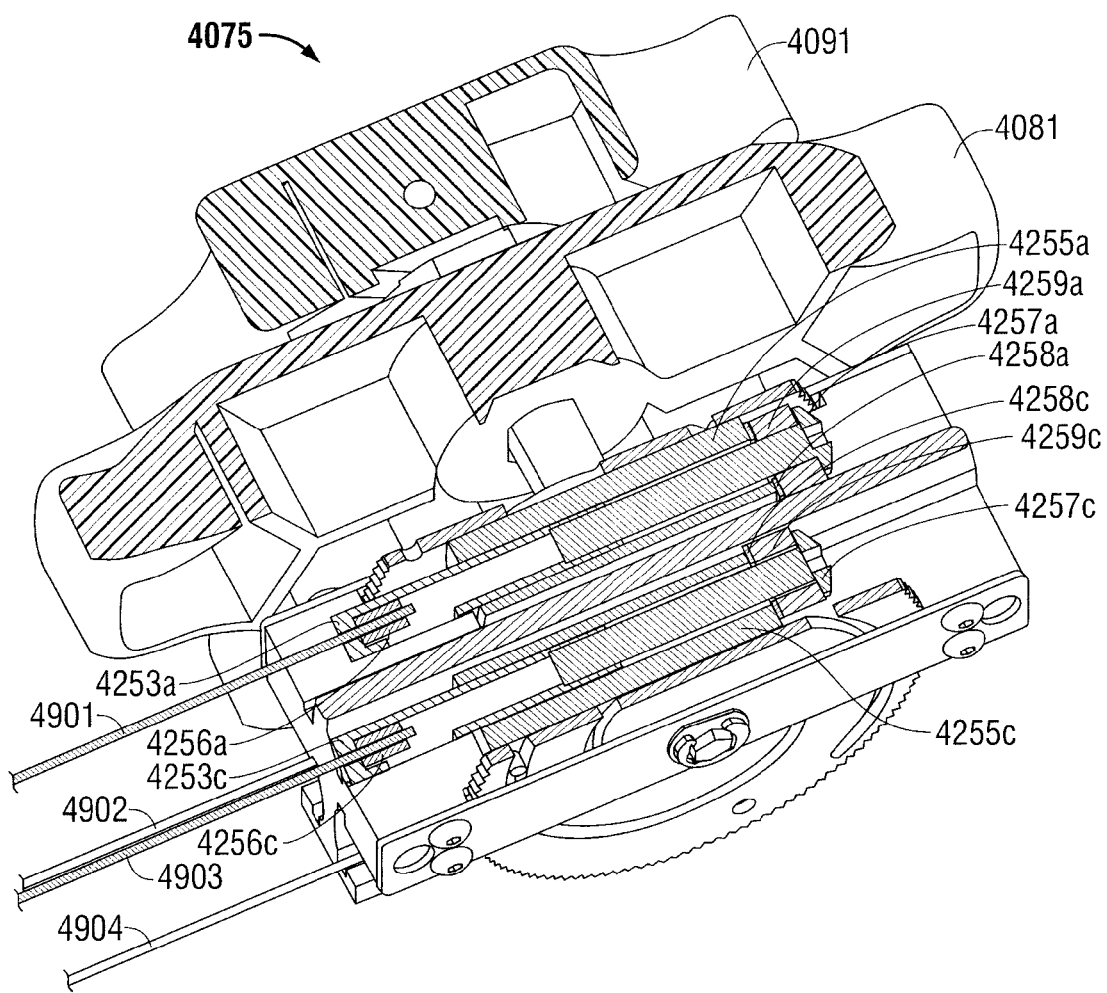
FIG. 61 is a cross-sectional view of the articulation assembly taken through the sliders of FIG. 59.

As depicted in FIG. 61, the sleeves 256a, 256c are crimped securely to an end of a respective steering cable 4901, 4903. The crimped sleeves 4256a, 4256c are disposed within a cavity of a respective coupling shaft 4253a, 4253c and are retained therein. The coupling shafts 4253a, 4253c are coupled to the sliders 44255a, 4255c by tensioning bolts 4257a, 4245c. The tensioning bolts 4257a, 4257c are threaded into the coupling shafts 4253a, 4253c to a depth sufficient to impart an appropriate tension on the steering cables 4901, 4903. The washers 4258a, 4258c and compression bushings 4259a, 4259c are positioned between the head of the tensioning bolts 4257a, 4245c, and the sliders 4255a, 4255c such that the compression bushings 4259a, 4259c may be compressed to resist the tension imparted to the steering cables 4901, 4903. Thus, the general tension in the steering cables 4901, 4903 may be adjusted by adjusting the depth to which the tensioning bolts 4257a, 4245c are threaded into the coupling shafts 4253a, 4253c. Adjusting the tension in the steering cables 4901, 4903 may facilitate accurately defining a home position of the end effector 4100.

Figure 62:
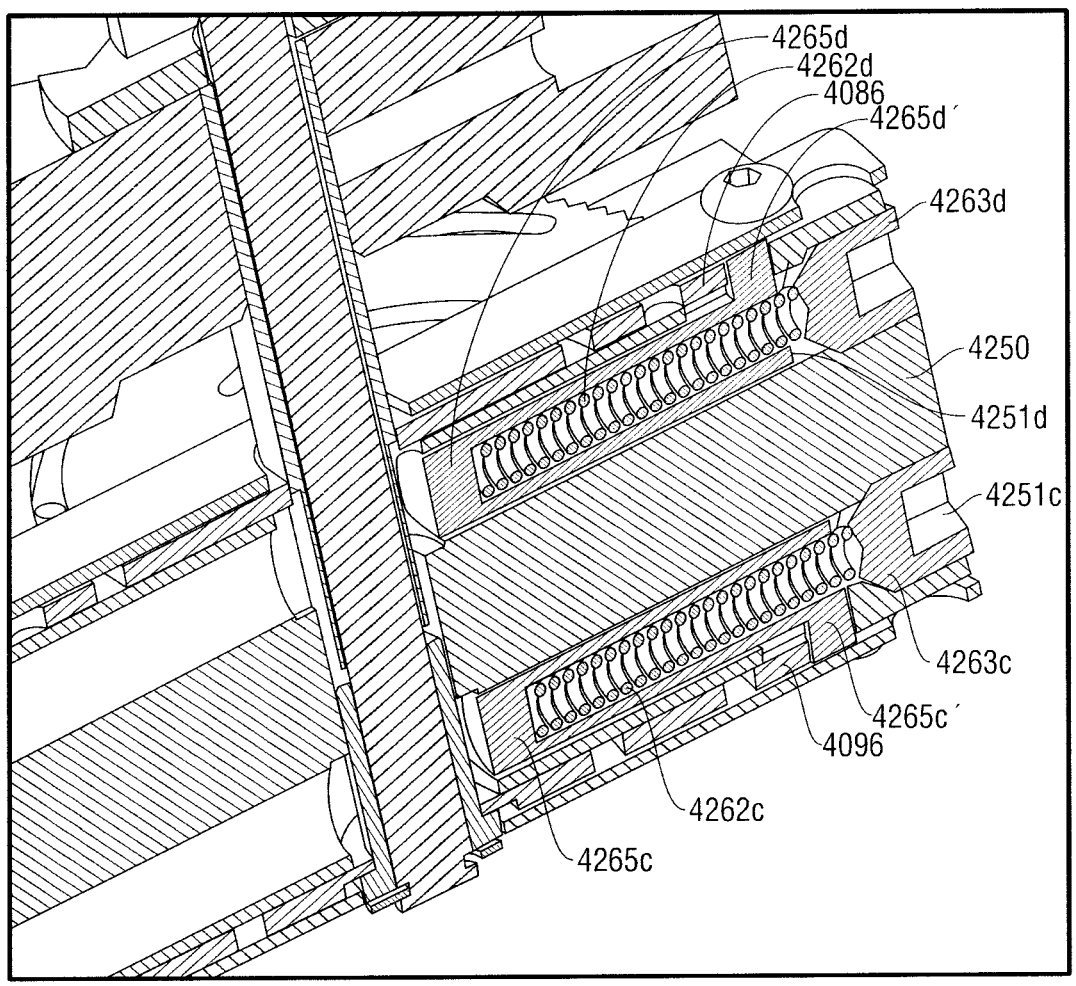
FIG. 62 is a cross-sectional perspective view of the articulation assembly depicting an indexing mechanism for maintaining the articulating portion of the elongated shaft in one of a number of discrete orientations.

Referring now to FIGS. 60 and 62, an indexing mechanism is provided including indexing slides 4265c and 4265d. Each of the slides 4265c and 4265d includes an engagement head 4265c', 4265d' having a tooth for engaging a respective outer circumferential surface of the cam wheels 4086, 4096. The outer circumferential surfaces of the cam wheels 4086, 4096 include discrete teeth disposed thereabout to permit incremental positioning of the cam wheels 4086, 4096, thus facilitating precise positioning of the end effector 4100. The indexing slides 4265c, 4265d are biased toward the cam wheels by springs 4262c, 4262d, which are held in position by threaded caps 4263c, 4263d.

As depicted in FIG. 62, the indexing slides 4265c, 4265d are slidably disposed within elongated bores 4251c and 4251d defined in the articulation block 4250. The springs 4262c, 4262d extend into the indexing slides 4265c, 4265d and bear against interior surfaces thereof to bias the engagement heads 4265c', 4265d' of the indexing slides 4265c, 4265d against the outer circumferential surfaces of the cam wheels 4086, 4096. The threaded caps 4263c, 4263d are threaded into the elongated bores 4251c, 4251d enclosing the indexing slides 4265c, 4265d therein. The caps 4263c, 4263d bear against the springs 4262c, 4262d such that the springs 4262c, 4262d are compressed sufficiently to provide an appropriate engagement force between the indexing slides 4265c, 4265d and the cam wheels 4086, 4096. The engagement force may be adjusted by adjusting the depth to which the caps 4265c, 4265d are threaded.

In use, as a user turns rotatable wheel 4091, for example, the cam wheel 4096 rotates along therewith. The discrete teeth on the outer circumferential surface of the cam wheel 4096 engage the engagement head 4265c' of the indexing slide 4265c and drive the indexing slide 4265c longitudinally against the bias of the spring 4262c. When the cam wheel 4096 is turned to a position such that the engagement head 4265c' engages the cam wheel 4096 between the discreet teeth, the articulating mechanism is driven to a relatively stable configuration by the spring 4262c, thus permitting the user to adjust the articulation of the end effector 4100 in small, but finite increments. Since the diameter of the cam wheel 4096 is relatively large, the resolution of the indexing mechanism may be relatively high, permitting the user to position the end effector 4100 accurately.

As can be appreciated, the articulation assembly 4075 enables a user to selectively articulate the distal end of the forceps 4010 (i.e., the end effector assembly 4100) as needed during surgery providing greater flexibility and enhanced maneuverability to the forceps 4010 especially in tight surgical cavities. By virtue of the unique arrangement of the four (4) spring loaded steering cables 4901-4904, each articulation control 4080 and 4090 provides a positive drive, back and forth motion to the end effector assembly 4100 that allows the end effector assembly 4100 to remain in an articulated configuration under strain or stress as the forceps 4010 is utilized, and/or prevent buckling of the elongated shaft 4012 (FIG. 57) through a range of motion. Due to the gradual slope of the cam slots 4086a, 4086b, 4096a, 4096b relative to the large angular travel of the rotatable wheels 4081, 4091, the articulating assembly 4075 tends to be self locking. This arrangement provides sufficient friction such that no additional lock is needed to maintain the end effector assembly 4100 in an articulated configuration. Various mechanical elements may be utilized to enhance this purpose including the indexing slides 4265c, 4265d and the tensioning/locking mechanisms associated with slides 4265a-4265d. In addition, the flexible shaft 4012 and end effector assembly 4100 may also be manipulated to allow multi-directional articulation through the manipulation of both wheels 4081 and 4091 simultaneously or sequentially thereby providing more maneuverability to the forceps.

Figure 63:
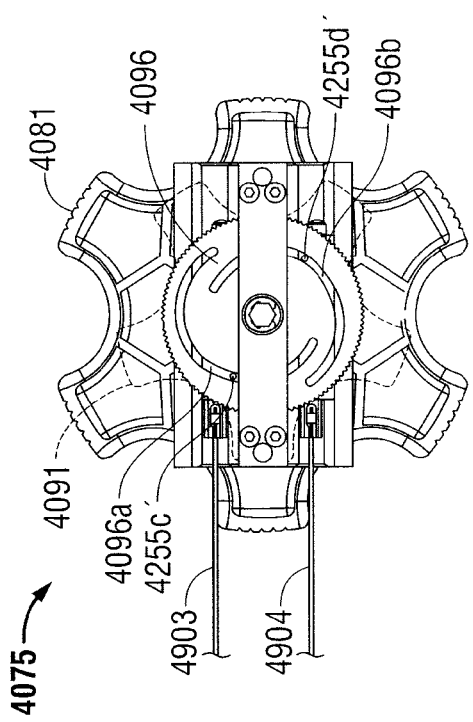
FIG. 63 is a bottom view of the articulation assembly in a "home" configuration for maintaining the articulating portion of the elongated shaft in a non-articulated orientation.
Figure 64:
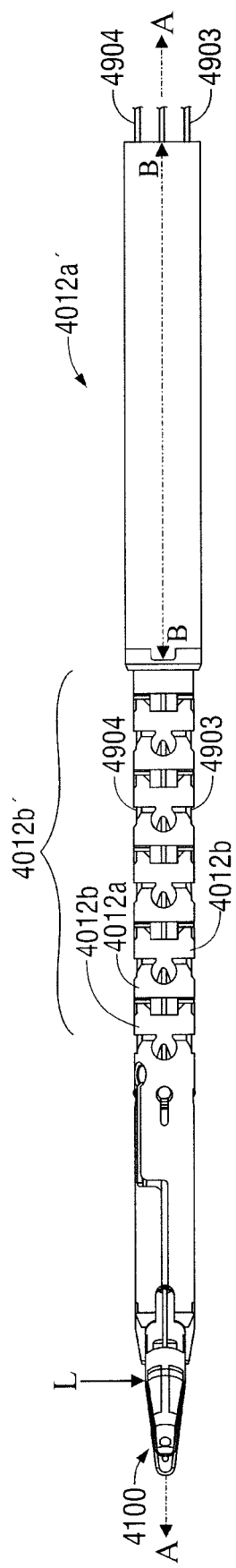
FIG. 64 is an enlarged, top view of the elongated shaft wherein the articulating portion is in the non-articulated orientation corresponding to the "home" configuration of the articulation assembly and the flexible portion is in an aligned configuration.

Referring now to FIGS. 63 and 64, the articulation assembly 4075 may be moved to a "home" position to maintain the articulating portion 4012b' of shaft 4012 in a non-articulated orientation aligned with the proximal shaft axis B-B. In the home position, the proximal portion 4012a' of the elongated shaft 4012 may also be aligned with the longitudinal axis A-A. When the articulation assembly 4075 is moved to a "home" position for the RIGHT and LEFT plane, the pins 4255c' and 4255d' are generally centered in the cam slots 4096a, 4096b. The steering cables 4903 and 4904, are thus disposed centrally along their respective longitudinal range of travel within the elongated shaft 4012. A tension imparted to the steering cables 4903, 4904 by tensioning bolts 4257c and 4257d causes the steering cables 4903, 4904 to draw the end effector support 4400 in a proximal direction and imparts a compressive force on the links 4012a, 4012b. This general tension reduces slack and play in the articulation assembly 4075. The "home" position represents a state of minimum stored energy in the substantially elastic steering cables 4903, 4904 in which the collective stretching is least.

In use, if the end effector assembly 4100 experiences a lateral load "L" the links 4012a and 4012b may resist a tendency to pivot relative to one another due to the general tension in the steering cables 4903, 4904. The links 4012a and 4012b may thus maintain alignment with the proximal shaft axis B-B. If however, the lateral load "L" is sufficient to overcome this tendency, the links 4012a will pivot relative to neighboring links 4012b to cause the end effector assembly 4100 to articulate relative to the proximal shaft axis B-B. The lateral load "L" will cause steering cable 4904 to stretch and move relative to steering cable 4903. The stretching of steering cable 4904 increases the collective tension and stored energy of the steering cables 4903, 4904 as the end effector assembly 4100 articulates. When the load "L" is removed, the links 4012a and 4012b will tend to return to the "home" position where the collective stored energy in the steering cables 4903 4904 is at a minimum. In this regard, the links 4012a and 4012b may be regarded as "self-centering."

Figure 65:
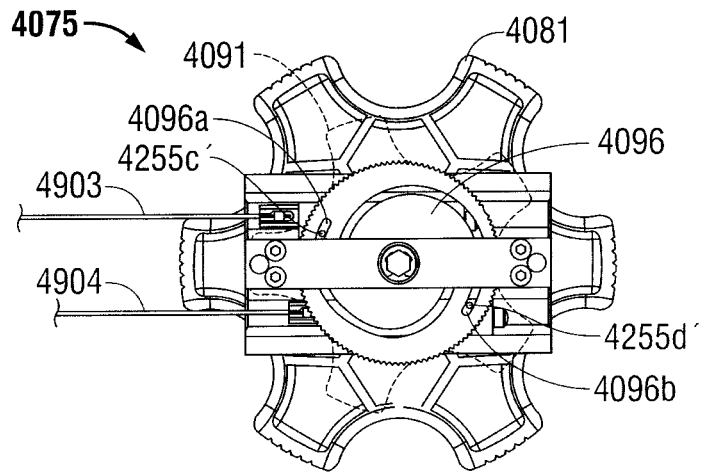
FIG. 65 is a bottom view of the articulation assembly in a configuration corresponding to a RIGHT articulated orientation of the articulating portion.
Figure 66:
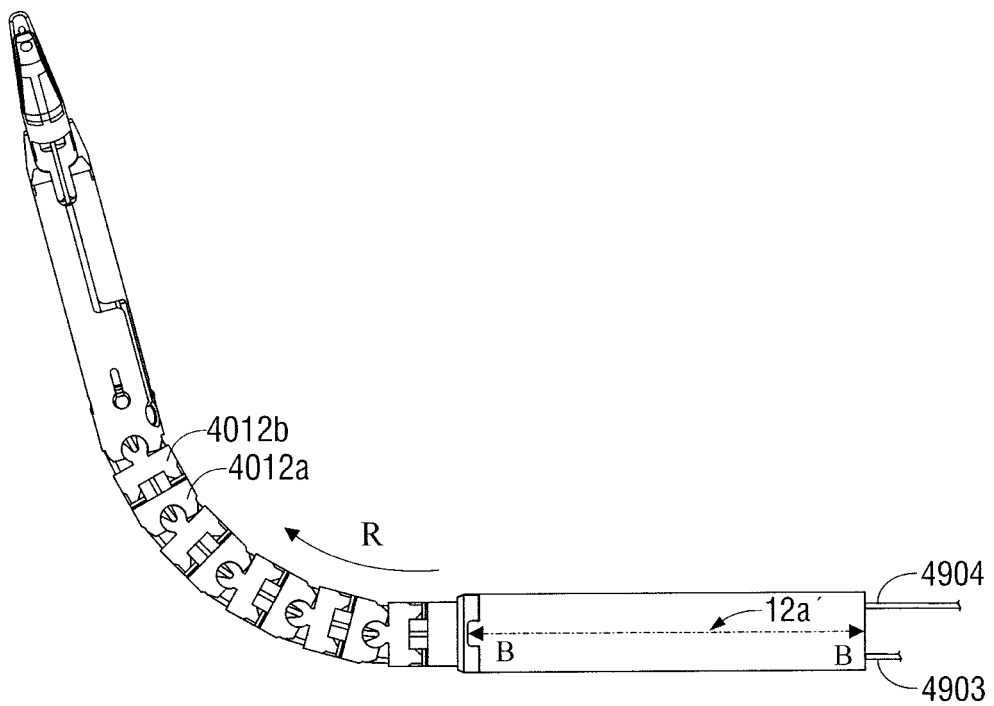
FIG. 66 is a top view of the elongated shaft of FIG. 65, wherein the articulating portion is in the RIGHT articulated orientation.
Figure 68:
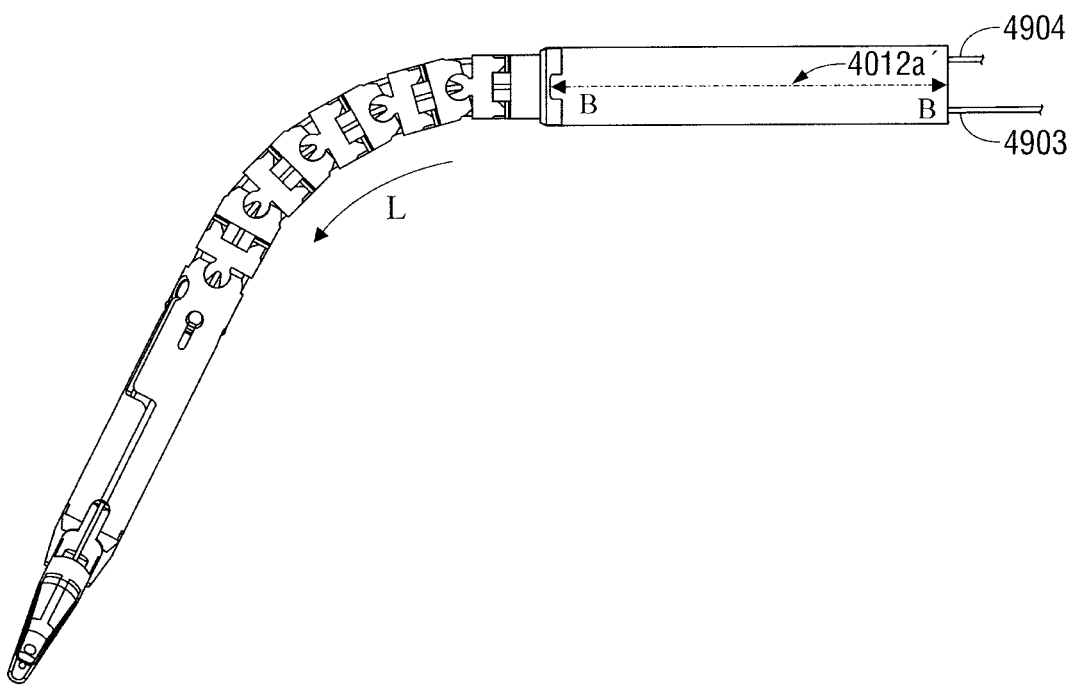
FIG. 68 is an enlarged, top view of the elongated shaft of FIG. 65, wherein the articulating portion is in the LEFT articulated orientation.

Referring now to FIGS. 65 and 66, the steering cables 4903, 4904 permit articulation assembly 4075 to be manipulated to articulate the end effector assembly 4100 in the RIGHT and LEFT plane. As discussed above with reference to FIG. 60, the rotatable wheel 4091 may be turned to move the steering cables 4903 and 4904. Rotation of the rotatable wheel 4091 rotates the cam wheel 4096 such that the cam slots 4096a, 4096b draw pins 4255c' and 4255d' toward a respective end of the cam slots 4096a, 4096b that is disposed radially outward on the cam wheel 4096. Since the steering cables 4903, 4904 are coupled to pins as described above, the steering cable 4903 is moved distally while the steering cable 4904 is drawn proximally. When the steering cable 4904 is retracted proximally as depicted in FIG. 65, the end effector assembly 4100 is articulated in the direction of arrow "R" with respect to the proximal shaft axis B-B as depicted in FIG. 66. The retraction of the steering cable 4904 causes the links 4012a to pivot relative to neighboring links 4012b in the direction of arrow "R." Similarly, rotatable wheel 4091 may be turned to retract steering cable 4903 as depicted in FIG. 67. In this configuration, the cam wheel 4096 is rotated such that the cam slots 4096a, 4096b draw pins 4255c' and 4255d' toward a respective end of the cam slots 4096a, 4096b that is disposed radially inward on the cam wheel 4096. Thus steering cable 4903 is retracted proximally and steering cable 4904 is moved distally and inducing articulation of the end effector 4100 in the direction of arrow "L" as depicted in FIG. 68.

Figure 69:
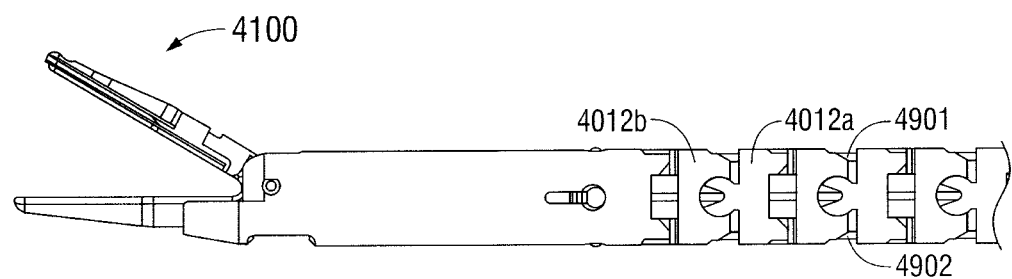
FIG. 69 is an enlarged, side view of a distal end of the elongated shaft, wherein the articulating portion is in the non-articulated orientation.
Figure 70:
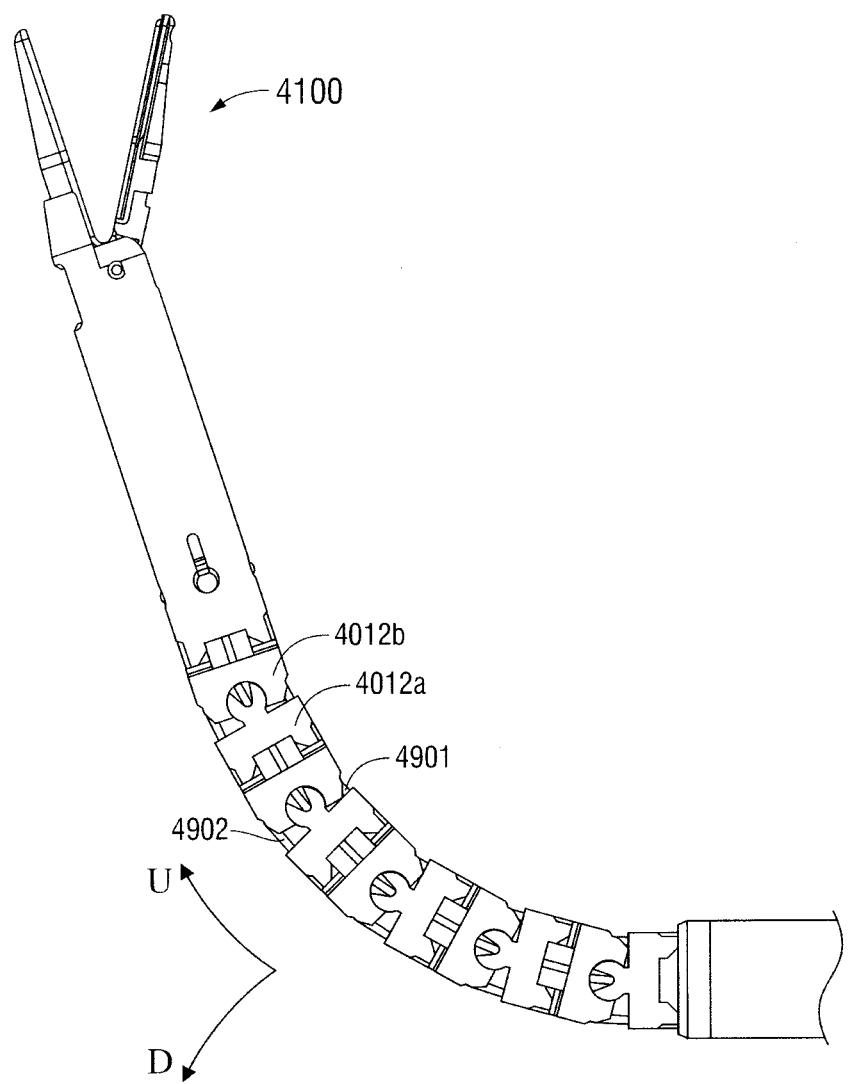
FIG. 70 is an enlarged, side view of the elongated shaft, wherein the articulating portion is in an UP articulated orientation.

Referring now to FIGS. 69 and 70, the radial offset between links 4012a and 4012b permit the end effector assembly 4100 to articulate in an UP and DOWN plane as well. For example, steering cable 4901 may be retracted by turning rotatable wheel 4081 as described above with reference to FIG. 60. The end effector assembly 4100 may thereby be articulated from a "home" position in the UP and DOWN plane as depicted in FIG. 69 to an articulated position in the direction of arrow "U" as depicted in FIG. 70. Similarly, the steering cable 4902 may be retracted to induce articulation of the end effector assembly in the direction of arrow "D".

The shape of the cam slots 4086a, 4086b, 4096a and 4096b is tapered to provide the mechanical advantage to overcome the increasing resistance to articulation as the articulating portion 4012b' of shaft 4012 is articulated in a given direction. The slope of the cam slots 4086a, 4086b, 96a and 96b decreases toward the extremities of the cam slots 4086a, 4086b, 4096a and 4096b. The cam slots 4086a, 4086b, 4096a, 4096b impart a decreasing longitudinal motion to the sliders 4255a-4255d for a given radial displacement of the cam members 4086, 4096 as the end effector 4100 is articulated further from the home position. Thus, a user must turn the wheels 4081, 4091 further, but with a reduced force as compared to a mechanism having non-tapered cam slots.

The forceps 4010 is suited for use by either a left or right-handed user and the articulation wheels 4081 and 4091 are particularly situated atop the housing 4020 (FIG. 57) to facilitate usage thereof by either handed user. In another embodiment of a forceps (not shown), the entire shaft 4012 (or portions thereof) may be flexible (or substantially flexible) along a length thereof to facilitate negotiation through a tortuous path. The number and size of the links 4012a and 4012b and end effector assembly 4100 may be altered to meet a particular surgical purpose or to enhance effectiveness of the forceps 4010 for a particular surgical solution.

In addition, it is also contemplated that one or more electrical motors may be utilized either automatically or manually to move the steering cables 4901-4904, advance the knife rod 4504 or retract the drive rod 4032. Although various cables, rods and shafts are employed for the various components herein, it is possible to substitute any one or all of these components with variations thereof depending upon a particular purpose.

While several embodiments of the disclosure have been depicted in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An endoscopic forceps, comprising:
   a housing;
   a shaft extending from the housing and defining a longitudinal axis, the shaft including a flexible portion;
   an end effector supported at a distal end of the shaft, the end effector including a pair of jaw members, the jaw members being adapted to connect to a source of electrosurgical energy, at least one jaw member being moveable relative to the other;
   a drive assembly disposed within the housing, the drive assembly operable to move the movable jaw member relative to the other jaw member from a first position wherein the movable jaw member is disposed in spaced relation relative to the other jaw member to a second position wherein the movable jaw member is closer to the other jaw member for manipulating tissue;
   a movable handle supported on the housing, the movable handle in mechanical cooperation with the drive assembly such that the movable handle is rotatable about a pivot to move the jaw members between the first and second positions;
   an articulation assembly including at least one steering cable operably coupled to the flexible portion of the shaft such that movement of the articulation assembly induces the flexible portion of the shaft to articulate relative to the longitudinal axis, said articulation assembly including at least one articulating wheel disposed atop the housing that operably couples to the at least one steering cable such that articulation of the at least one articulation wheel moves the at least one steering cable to articulate the flexible portion of the shaft relative to the longitudinal axis;
   wherein the articulation assembly includes at least one slider coupled to the at least one steering cable, and wherein the at least one slider cooperates with the at least one articulating wheel to move the at least one steering cable longitudinally in response to rotational movement of the at least one articulating wheel;
   wherein the at least one articulating wheel is operably coupled to the at least one slider by a spindle, the spindle configured to rotate along with the at least one articulating wheel; and
   wherein the spindle is operably coupled to the at least one slider by a cam member configured to rotate along with the spindle, and wherein the cam member includes an eccentric arcuate surface thereon having a center dissimilar from a center of rotation of the cam member, and wherein the at least one slider is operatively coupled to the eccentric arcuate surface such that rotation of the cam member induces longitudinal motion of the slider.

2. The endoscopic forceps according to claim 1, wherein the articulation assembly includes a plurality of steering cables that are movable to articulate the flexible portion of the shaft in multiple planes relative to the longitudinal axis.

3. The endoscopic forceps according to claim 1, wherein the spindle operably couples to an indexing wheel that allows the articulating wheel to move in discreet increments thereby permitting discreet articulation of the flexible portion of the shaft.

4. The endoscopic forceps according to claim 2, wherein the articulation assembly includes two articulating wheels that are operably coupled to the plurality of steering cables to move the flexible portion of the shaft, a first articulating wheel configured to move the flexible portion of the shaft substantially along a first plane and a second articulating wheel configured to move the flexible portion of the shaft substantially along a second plane.

5. The endoscopic forceps according to claim 4, wherein movement of each of the two articulating wheels is independent of movement of the other such that movement of the articulating wheels sequentially or simultaneously induces a corresponding sequential or simultaneous motion of the flexible portion of the shaft in the first and second planes.

6. The endoscopic forceps according to claim 1, wherein the flexible portion of the shaft includes a plurality of joints that are nestingly arranged to facilitate articulation of the flexible portion of the shaft relative to the longitudinal axis.

7. The endoscopic forceps according to claim 6, wherein each joint of the plurality of joints includes at least one distal knuckle and at least one proximal clevis that nestingly engage one another to form the flexible portion of the shaft.

8. The endoscopic forceps according to claim 7, wherein each joint of the plurality of joints includes a pair of opposing distal knuckles and a pair of opposing proximal clevises, said pair of opposing distal knuckles and said pair of opposing proximal clevises being offset ninety degrees) (90°) relative to one another.

9. The endoscopic forceps according to claim 6, wherein a portion of the shaft disposed proximally of the plurality of joints is substantially flexible along a length thereof to facilitate negotiation along a tortuous path.

10. The endoscopic forceps according to claim 1, wherein said at least one steering cable is adapted to provide a return path to the electrosurgical energy source.

11. The endoscopic forceps according to claim 1, wherein the drive assembly includes a drive rod extending at least partially through the flexible portion of the shaft, the drive rod operably coupled to the movable jaw member such that longitudinal reciprocation of the drive rod induces movement of the movable jaw member between the first and second positions.

12. The endoscopic forceps according to claim 11, wherein the drive assembly includes a four bar mechanical linkage operably coupled to the drive rod to induce reciprocation of the drive rod, and wherein the four bar mechanical linkage is operable from the housing.

13. The endoscopic forceps according to claim 11, wherein the drive rod is substantially flexible.

14. An endoscopic surgical instrument comprising:
   an end effector including a pair of jaw members, at least one jaw member of the pair of jaw members being movable relative to the other to move the end effector between an open configuration wherein the jaw members are substantially spaced for receiving tissue and a closed configuration wherein the jaw members are closer together for contacting the tissue;
   a handle being manually movable to selectively induce motion in the end effector between the open configuration and the closed configuration;
   an elongated shaft defining a longitudinal axis and including distal and proximal ends, the distal end coupled to the end effector and the proximal end coupled to the handle, the elongated shaft including an articulating portion movable between an aligned configuration and an articulated configuration with respect to the longitudinal axis,
   an articulation assembly operable to move the articulating portion of the elongated shaft between the aligned configuration and articulated configuration, the articulation assembly comprising:
- a first actuator positioned on the instrument for manipulation by an operator during a surgical procedure;
- a first cam member coupled to the first actuator such that the first actuator is operable to rotate the first cam member about a center of rotation, the first cam member including an eccentric arcuate surface thereon having a center dissimilar from the center of rotation of the cam member; and
- a first pair of cables coupled to the arcuate surface of the first cam member such that rotation of the cam member induces differential longitudinal motion in the cables, the first pair of cables coupled to the distal end of the elongated shaft such that the differential longitudinal motion in the first pair of cables moves the articulating portion of the elongated shaft between the aligned configuration and the articulated configuration in a first plane of articulation.

15. The instrument according to claim 14, wherein the articulation assembly includes a second actuator positioned on the instrument for manipulation by an operator during a surgical procedure, the second actuator operable to induce motion of the articulating portion of the elongated shaft between the aligned configuration and the articulated configuration in a second plane of articulation.

16. The instrument according to claim 15, wherein the second actuator is operable to rotate a second cam member about a center of rotation, and wherein the second cam member is coupled to a second pair of cables being coupled to the distal end of the elongated shaft.

17. The instrument according to claim 14, wherein the first actuator comprises a rotatable wheel and wherein the first cam member comprises a cam wheel, the cam wheel being coupled to the rotatable wheel such that a given angular displacement of the rotatable wheel induces an equivalent angular displacement of the cam wheel.

18. The instrument according to claim 17, wherein the arcuate surface includes a cam slot defined in the cam wheel, the cam slot extending between a radially inward position and a radially outward position on the cam wheel.

19. The instrument according to claim 18, wherein the cam slot is tapered such that a given angular displacement of the cam wheel induces greater differential longitudinal motion in the first pair of cables when the cam wheel is closer to a home position wherein the articulating portion is in the aligned configuration than when the cam wheel is further from the home position.

20. The instrument according to claim 14, further comprising an indexing mechanism for maintaining the articulation assembly in a plurality of relatively stable configurations to facilitate orienting the end effector in one of a plurality of discrete orientations.

21. The instrument according to claim 20, wherein the indexing mechanism includes an indexing slide for engaging a plurality of teeth disposed on an outer circumferential surface of the first cam member.

22. The instrument according to claim 15, wherein the articulating portion includes a plurality of links arranged sequentially such that each of the links may pivot relative to a neighboring link to move the articulating portion between the aligned and articulated configurations.

23. The instrument according to claim 22, wherein a first pivoting axis defined by one of the links is radially offset from a second pivoting axis defined by another of the plurality of links by about 90° to define the second plane of articulation such that the second plane of articulation is substantially orthogonal to the first plane of articulation.

24. An endoscopic forceps, comprising:
- a housing;
- a shaft extending from the housing and defining a longitudinal axis, the shaft including a flexible portion;
- an end effector supported at a distal end of the shaft, the end effector including a pair of jaw members, the jaw members being adapted to connect to a source of electrosurgical energy, at least one jaw member being moveable relative to the other;
- a drive assembly disposed within the housing, the drive assembly operable to move the movable jaw member relative to the other jaw member from a first position wherein the movable jaw member is disposed in spaced relation relative to the other jaw member to a second position wherein the movable jaw member is closer to the other jaw member for manipulating tissue;
- a movable handle supported on the housing, the movable handle in mechanical cooperation with the drive assembly such that the movable handle is rotatable about a pivot to move the jaw members between the first and second positions;
- an articulation assembly including at least one steering cable operably coupled to the flexible portion of the shaft such that movement of the articulation assembly induces the flexible portion of the shaft to articulate relative to the longitudinal axis, said articulation assembly including at least one articulating wheel disposed atop the housing that operably couples to the at least one steering cable such that articulation of the at least one articulation wheel moves the at least one steering cable to articulate the flexible portion of the shaft relative to the longitudinal axis;
- wherein the flexible portion of the shaft includes a plurality of joints that are nestingly arranged to facilitate articulation of the flexible portion of the shaft relative to the longitudinal axis;
- wherein each joint of the plurality of joints includes at least one distal knuckle and at least one proximal clevis that nestingly engage one another to form the flexible portion of the shaft; and
- wherein each joint of the plurality of joints includes a pair of opposing distal knuckles and a pair of opposing proximal clevises, said pair of opposing distal knuckles and said pair of opposing proximal clevises being offset ninety degrees (90°) relative to one another.

* * * * *